United States Patent
Jeon et al.

(10) Patent No.: US 10,566,566 B2
(45) Date of Patent: Feb. 18, 2020

(54) ORGANOMETALLIC COMPOUND, ORGANIC LIGHT-EMITTING DEVICE INCLUDING THE ORGANOMETALLIC COMPOUND, AND DIAGNOSIS COMPOSITION INCLUDING THE ORGANOMETALLIC COMPOUND

(71) Applicant: SAMSUNG ELECTRONICS CO., LTD., Suwon-si, Gyeonggi-do (KR)

(72) Inventors: Aram Jeon, Suwon-si (KR); Chul Baik, Suwon-si (KR); Jungin Lee, Hwaseong-si (KR); Hwayoung Cho, Hwaseong-si (KR); Seokhwan Hong, Seoul (KR); Kyuyoung Hwang, Anyang-si (KR); Ohyun Kwon, Seoul (KR); Yoonhyun Kwak, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 365 days.

(21) Appl. No.: 15/487,820

(22) Filed: Apr. 14, 2017

(65) Prior Publication Data
US 2018/0090707 A1    Mar. 29, 2018

(30) Foreign Application Priority Data
Sep. 27, 2016    (KR) .................. 10-2016-0124238

(51) Int. Cl.
*H01L 51/50* (2006.01)
*H01L 51/52* (2006.01)
(Continued)

(52) U.S. Cl.
CPC ...... *H01L 51/5203* (2013.01); *C07F 15/0086* (2013.01); *C09K 11/025* (2013.01);
(Continued)

(58) Field of Classification Search
None
See application file for complete search history.

(56) References Cited

U.S. PATENT DOCUMENTS 7,442,797 B2    10/2008    Itoh et al.
7,939,669 B2    5/2011    Suh et al.
(Continued)

FOREIGN PATENT DOCUMENTS

| JP | 2010-135689 A | 6/2010 |
| WO | 2005-042444 A2 | 5/2005 |
| WO | 2007-078182 A1 | 7/2007 |

*Primary Examiner* — Gregory D Clark
(74) *Attorney, Agent, or Firm* — Cantor Colburn LLP

(57) ABSTRACT

An organometallic compound represented by Formula 1:

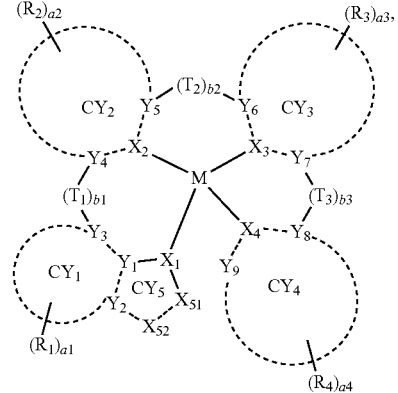

Formula 1 wherein, in Formula 1, groups and variables are the same as described in the specification.

20 Claims, 1 Drawing Sheet

(51) Int. Cl.
*C07F 15/00* (2006.01)
*C09K 11/02* (2006.01)
*C09K 11/06* (2006.01)
*H01L 51/00* (2006.01)

(52) U.S. Cl.
CPC .......... *C09K 11/06* (2013.01); *H01L 51/0072* (2013.01); *H01L 51/0087* (2013.01); *H01L 51/0094* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *C09K 2211/185* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

2013/0274473 A1 10/2013 Che et al.
2015/0194616 A1* 7/2015 Li .................... H01L 51/0087
                                                          546/4

* cited by examiner

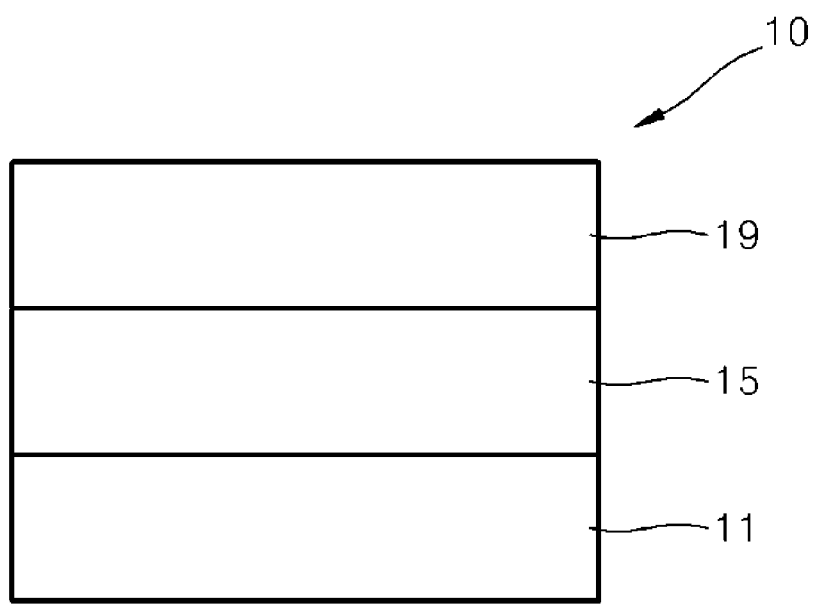

ORGANOMETALLIC COMPOUND, ORGANIC LIGHT-EMITTING DEVICE INCLUDING THE ORGANOMETALLIC COMPOUND, AND DIAGNOSIS COMPOSITION INCLUDING THE ORGANOMETALLIC COMPOUND

CROSS-REFERENCE TO RELATED APPLICATION

This application claims priority to Korean Patent Application No. 10-2016-0124238, filed on Sep. 27, 2016, in the Korean Intellectual Property Office, and all the benefits accruing therefrom under 35 U.S.C. § 119, the content of which is incorporated herein in its entirety by reference.

BACKGROUND

1. Field

One or more embodiments relate to an organometallic compound, an organic light-emitting device including the organometallic compound, and a diagnosis composition including the organometallic compound.

2. Description of the Related Art

Organic light-emitting devices (OLEDs) are self-emission devices that produce full-color images, and also have improved characteristics in terms of viewing angles, response time, luminance, driving voltage, and response speed.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transition from an excited state to a ground state, thereby generating light.

Meanwhile, luminescent compounds may be used to monitor, sense, or detect a biological material such as a cell protein. Examples of such luminescent compounds include a phosphorescent luminescent compound.

Various types of organic light emitting devices are known. However, there still remains a need in OLEDs having low driving voltage, high efficiency, high brightness, and long lifespan.

SUMMARY

One or more embodiments include a novel organometallic compound, an organic light-emitting device including the novel organometallic compound, and a diagnosis composition including the novel organometallic compound.

Additional aspects will be set forth in part in the description which follows and, in part, will be apparent from the description, or may be learned by practice of the presented embodiments.

According to one or more embodiments, an organometallic compound is represented by Formula 1:

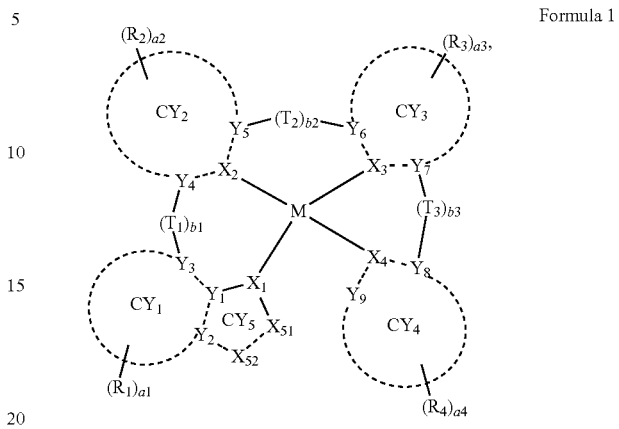

Formula 1 wherein, in Formula 1,

M may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), $X_1$ may be N and a bond between $X_1$ and M may be a covalent bond, $X_2$ to $X_4$ may each independently be N or C, at least one of $X_2$ to $X_4$ may be C, one bond selected from a bond between $X_2$ and M, a bond between $X_3$ and M, and a bond between $X_4$ and M may be a covalent bond, and the remaining two bonds may each be a coordinate bond, $Y_1$ to $Y_9$ may each independently be C or N, a bond between $Y_1$ and $Y_2$, a bond between $Y_1$ and $Y_3$, a bond between $X_2$ and $Y_4$, a bond between $X_2$ and $Y_5$, a bond between $X_3$ and $Y_6$, a bond between $X_3$ and $Y_7$, a bond between $X_4$ and $Y_8$, a bond between $X_4$ and $Y_9$, a bond between $Y_2$ and $X_{52}$, and a bond between $X_{51}$ and $X_{52}$ may each independently be a single bond or a double bond, $CY_1$ to $CY_5$ may each independently be selected from a $C_5$-$C_{30}$ carbocyclic group and a $C_1$-$C_{30}$ heterocyclic group, a cyclometallated ring formed by $CY_5$, $CY_1$, $CY_2$, and M may be a 6-membered ring, a 7-membered ring, or an 8-membered ring, $T_1$ to $T_3$ may each independently be selected from *—O—*', *—S—*', *—C($R_5$)($R_6$)—', *—C($R_5$)=*', *=($R_5$)—*', *—C($R_5$)=C($R_6$)—*', *—C(=O)—*', *—C(=S)—*', *—C≡C—*', *—N($R_5$)—*', *—Si($R_5$)($R_6$)—*', and *—P($R_5$)($R_6$)—', $R_5$ and $R_6$ may optionally be linked via a first linking group to form a substituted or unsubstituted $C_5$-$C_{30}$ carbocyclic group or a substituted or unsubstituted $C_1$-$C_{30}$ heterocyclic group, b1 to b3 may each independently be 0, 1, 2, or 3, wherein when b1 is zero, *-$(T_1)_{b1}$-*' may be a single bond, when b2 is zero, *-$(T_2)_{b2}$-*' may be a single bond, and when b3 is zero, *-$(T_3)_{b3}$-*' may be a single bond, $X_{51}$ may be selected from O, S, N, N($R_{51}$), C($R_{51}$), C($R_{51}$)($R_{52}$), Si($R_{51}$)($R_{52}$), and C(=O), $X_{52}$ may be selected from O, S, N, N($R_{53}$), C($R_{53}$), C($R_{53}$)($R_{54}$), Si($R_{53}$)($R_{54}$), and C(=O), $R_{51}$ and $R_{52}$ may optionally be linked via a second linking group to form a substituted or unsubstituted $C_5$-$C_{30}$ carbocyclic group or a substituted or unsubstituted $C_1$-$C_{30}$ heterocyclic group, $R_{53}$ and $R_{54}$ may optionally be linked via a third linking group to form a substituted or unsubstituted $C_5$-$C_{30}$ carbocyclic group or a substituted or unsubstituted $C_1$-$C_{30}$ heterocyclic group, $R_{51}$ and $R_{53}$ may optionally be linked via a fourth linking group to form a substituted or unsubstituted $C_5$-$C_{30}$ carbocyclic group or a substituted or unsubstituted $C_1$-$C_{30}$ heterocyclic group, $R_1$ to $R_6$ and $R_{51}$ to $R_{54}$ may each independently be selected from hydrogen, deuterium, —F, —Cl, —Br, —I, —SF$_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —P(=O)(Q$_8$)(Q$_9$), a1 to a4 may each independently be 0, 1, 2, 3, 4, or 5, two of groups $R_1$ in the number of a1 may optionally be linked to form a substituted or unsubstituted $C_5$-$C_{30}$ carbocyclic group or a substituted or unsubstituted $C_1$-$C_{30}$ heterocyclic group, two of groups $R_2$ in the number of a2 may optionally be linked to form a substituted or unsubstituted $C_5$-$C_{30}$ carbocyclic group or a substituted or unsubstituted $C_1$-$C_{30}$ heterocyclic group, two of groups $R_3$ in the number of a3 may optionally be linked to form a substituted or unsubstituted $C_5$-$C_{30}$ carbocyclic group or a substituted or unsubstituted $C_1$-$C_{30}$ heterocyclic group, two of groups $R_4$ in the number of a4 may optionally be linked to form a substituted or unsubstituted $C_5$-$C_{30}$ carbocyclic group or a substituted or unsubstituted $C_1$-$C_{30}$ heterocyclic group, two or more neighboring groups selected from $R_1$ to $R_4$ may optionally be linked to form a substituted or unsubstituted $C_5$-$C_{30}$ carbocyclic group or a substituted or unsubstituted $C_1$-$C_{30}$ heterocyclic group,

* and *' each indicate a binding site to a neighboring atom, and at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{11}$)(Q$_{12}$), —Si(Q$_{13}$)(Q$_{14}$)(Q$_{15}$), —B(Q$_{16}$)(Q$_{17}$), and —P(=O)(Q$_{18}$)(Q$_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), and —P(=O)(Q$_{28}$)(Q$_{29}$); and —N(Q$_{31}$)(Q$_{32}$), —Si(Q$_{33}$)(Q$_{34}$)(Q$_{35}$), —B(Q$_{36}$)(Q$_{37}$), and —P(=O)(Q$_{38}$)(Q$_{39}$), wherein Q$_1$ to Q$_9$, Q$_{11}$ to Q$_{19}$, Q$_{21}$ to Q$_{29}$, and Q$_{31}$ to Q$_{39}$ may each independently be selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to one or more embodiments, an organic light-emitting device includes:

a first electrode;

a second electrode; and an organic layer disposed between the first electrode and the second electrode, wherein the organic layer includes an emission layer and at least one organometallic compound.

The organometallic compound may act as a dopant in the emission layer.

According to one or more embodiments, a diagnosis composition includes at least one organometallic compound represented by Formula 1.

BRIEF DESCRIPTION OF THE DRAWING

These and/or other aspects will become apparent and more readily appreciated from the following description of the embodiments, taken in conjunction with FIG. 1, which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment may be represented by Formula 1 below:

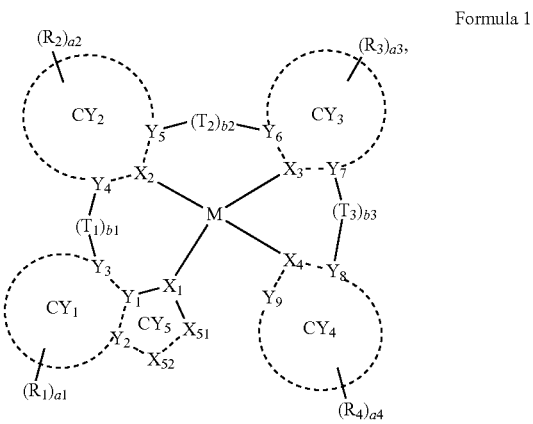

Formula 1 wherein M in Formula 1 may be beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au).

In one or more embodiments, M in Formula 1 may be platinum (Pt), but embodiments of the present disclosure are not limited thereto.

The organometallic compound represented by Formula 1 may be a neutral compound which does not consist of an ion pair of a cation and an anion.

$X_1$ in Formula 1 may be N and a bond between $X_1$ and M may be a covalent bond.

$X_2$ to $X_4$ may each independently be N or C, one of $X_2$ to $X_4$ may be C, one bond selected from a bond between $X_2$ and M, a bond between $X_3$ and M, and a bond between $X_4$ and M may be a covalent bond, and the remaining two bonds may each be a coordinate bond.

In one or more embodiments, in Formula 1, $X_2$ may be C, $X_3$ and $X_4$ may be N, a bond between $X_2$ and M may be a covalent bond, and a bond $X_3$ and M and a bond between $X_4$ and M may be a coordinate bond;

$X_3$ may be C, $X_2$ and $X_4$ may be N, a bond between $X_3$ and M may be a covalent bond, and a bond between $X_2$ and M and a bond between $X_4$ and M may be a coordinate bond; or $X_4$ may be C, $X_2$ and $X_3$ may be N, a bond between $X_4$ and M may be a covalent bond, and a bond between $X_2$ and M and a bond between $X_3$ and M may be a coordinate bond, but embodiments of the present disclosure are not limited thereto.

In Formula 1, $Y_1$ to $Y_9$ may each independently be C or N, and a bond between $Y_1$ and $Y_2$, a bond between $Y_1$ and $Y_3$, a bond between $X_2$ and $Y_4$, a bond between $X_2$ and $Y_5$, a bond between $X_3$ and $Y_6$, a bond between $X_3$ and $Y_7$, a bond between $X_4$ and $Y_8$, a bond between $X_4$ and $Y_9$, a bond between $Y_2$ and $X_{52}$, and a bond between $X_{51}$ and $X_{52}$ may each independently be a single bond or a double bond.

In one or more embodiments, $Y_1$ to $Y_9$ in Formula 1 may be C, but embodiments of the present disclosure are not limited thereto.

$CY_1$ to $CY_5$ in Formula 1 may each independently be selected from a $C_5$-$C_{30}$ carbocyclic group and a $C_1$-$C_{30}$ heterocyclic group.

In one or more embodiments, in Formula 1, $CY_1$, $CY_2$, and $CY_4$ may each independently be a 6-membered cyclic group, $CY_3$ may be selected from a 6-membered cyclic group, a fluorene group, a carbazole group, a dibenzofuran group, a dibenzothiophene group, a dibenzosilole group, an azafluorene group, an azacarbazole group, an azadibenzofuran group, an azadibenzothiophene group, and an azadibenzosilole group, and $CY_5$ may be a 5-membered ring.

In one or more embodiments, $CY_1$ to $CY_4$ in Formula 1 may each independently be selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an iso-oxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group.

In one or more embodiments, $CY_1$ to $CY_4$ in Formula 1 may each independently be selected from a benzene group, a naphthalene group, a fluorene group, a carbazole group, a dibenzofuran group, a dibenzothiophene group, a dibenzosilole group, an azafluorene group, an azacarbazole group, an azadibenzofuran group, an azadibenzothiophene group, an azadibenzosilole group, a 1,2,3,4-tetrahydronaphthalene group, a pyridine group, a pyrimidine group, a quinoline group, an isoquinoline group, a quinoxaline group, a quinazoline group, a 5,6,7,8-tetrahydroisoquinoline group, and a 5,6,7,8-tetrahydroquinoline group.

In one or more embodiments, in Formula 1, $CY_1$ and $CY_3$ may each independently be selected from a benzene group, a naphthalene group, a fluorene group, a carbazole group, a dibenzofuran group, a dibenzothiophene group, a dibenzosilole group, an azafluorene group, an azacarbazole group, an azadibenzofuran group, an azadibenzothiophene group, an azadibenzosilole group, and a 1,2,3,4-tetrahydronaphthalene group, and $CY_2$ and $CY_4$ may each independently be selected from a pyridine group, a pyrimidine group, a quinoline group, an isoquinoline group, a quinoxaline group, a quinazoline group, a 5,6,7,8-tetrahydroisoquinoline group, and a 5,6,7,8-tetrahydroquinoline group, but embodiments of the present disclosure are not limited thereto.

A cyclometallated ring formed by $CY_5$, $CY_1$, $CY_2$, and M in Formula 1 may be a 6-membered ring, a 7-membered ring, or an 8-membered ring.

In one or more embodiments, a cyclometallated ring formed by $CY_5$, $CY_1$, $CY_2$, and M in Formula 1 may be a 6-membered ring, but embodiments of the present disclosure are not limited thereto.

$T_1$ to $T_3$ in Formula 1 may each independently be selected from *—O—*', *—S—*', *—C($R_5$)($R_6$)—*', *—C($R_5$)=*', *=C($R_5$)—*', *—C($R_5$)=C($R_6$)—*', *—C(=O)—*', *—C(=S)—*', *—C≡C—*', *—N($R_5$)—*', *—Si($R_5$)($R_6$)—*', and *—P($R_5$)($R_6$)—*'. $R_5$ and $R_6$ are the same as described below. * and *' each indicate a binding site to a neighboring atom.

$R_5$ and $R_6$ may optionally be linked via a first linking group to form a substituted or unsubstituted $C_5$-$C_{30}$ carbocyclic group or a substituted or unsubstituted $C_1$-$C_{30}$ heterocyclic group.

In one or more embodiments, $T_1$ to $T_3$ in Formula 1 may each independently be selected from *—O—*', *—S—*', *—C($R_5$)($R_6$)—*', *—N($R_5$)—*', *—Si($R_5$)($R_6$)—*', and *—P($R_5$)($R_6$)—*'.

In one or more embodiments, $T_1$ to $T_3$ may each independently be selected from *—C($R_5$)($R_6$)—*', *—Si($R_5$)($R_6$)—*', and *—P($R_5$)($R_6$)—*'.

$R_5$ and $R_6$ may be linked via a first linking group, the first linking group may be selected from a single bond, *—O—*', *—S—*', *—C($R_9$)($R_{10}$)—*', *—C($R_9$)=*', *=C($R_9$)—*', *—C($R_9$)=C($R_{10}$)—*', *—C(=O)—*', *—C(=S)—*', *—C≡C—*', *—N($R_9$)—*', *—Si($R_9$)($R_{10}$)—*', and *—P($R_9$)($R_{10}$)—*', and $R_9$ and $R_{10}$ are the same as described above in connection with $R_5$, and * and *' each indicate a binding site to a neighboring atom, but embodiments of the present disclosure are not limited thereto.

In one or more embodiments, $T_1$ to $T_3$ in Formula 1 may each be *—N($R_5$)—*', but embodiments of the present disclosure are not limited thereto.

b1, b2, and b3 in Formula 1 respectively indicate the number of groups $T_1$, the number of groups $T_2$, and the number of groups $T_3$ and may each independently be 0, 1, 2, or 3. When b1 is zero, *-$(T_1)_{b1}$-*' may be a single bond, when b2 is zero, *-$(T_2)_{b2}$-' may be a single bond, and when b3 is zero, *-$(T_3)_{b3}$-*' may be a single bond.

For example, b1 to b3 may each independently be 0 or 1.

In one or more embodiments, the sum of b1, b2, and b3 in Formula 1 may be one or more. That is, at least one of *-$(T_1)_{b1}$-', *-$(T_2)_{b2}$-*', and *-$(T_3)_{b3}$-*' in Formula 1 may not be a single bond.

In one or more embodiments, the sum of b1, b2, and b3 in Formula 1 may be one or two. For example, the sum of b1, b2, and b3 in Formula 1 may be one, but embodiments of the present disclosure are not limited thereto.

In one or more embodiments, in Formula 1, b1 may be one, and b2 and b3 may each be zero;

b2 may be one, and b1 and b3 may each be zero; or b3 may be one, and b1 and b2 may each be zero, but embodiments of the present disclosure are not limited thereto.

$X_{51}$ in Formula 1 may be selected from O, S, N, $N(R_{51})$, $C(R_{51})$, $C(R_{51})(R_{52})$, $Si(R_{51})(R_{52})$, and $C(=O)$, and $X_{52}$ may be selected from O, S, N, $N(R_{53})$, $C(R_{53})$, $C(R_{53})(R_{54})$, $Si(R_{53})(R_{54})$, and $C(=O)$. $R_{51}$ to $R_{54}$ are the same as described above.

$R_{51}$ and $R_{52}$ may optionally be linked via a second linking group to form a substituted or unsubstituted $C_5$-$C_{30}$ carbocyclic group or a substituted or unsubstituted $C_1$-$C_{30}$ heterocyclic group, $R_{53}$ and $R_{54}$ may optionally be linked via a third linking group to form a substituted or unsubstituted $C_5$-$C_{30}$ carbocyclic group or a substituted or unsubstituted $C_1$-$C_{30}$ heterocyclic group, and $R_{51}$ and $R_{53}$ may optionally be linked via a fourth linking group to form a substituted or unsubstituted $C_5$-$C_{30}$ carbocyclic group or a substituted or unsubstituted $C_1$-$C_{30}$ heterocyclic group.

The first linking group, the second linking group, the third linking group, and the fourth linking group may each independently be selected from a single bond, *—O—*', *—S—*', *—$C(R_9)(R_{10})$—*', *—$C(R_9)$=*', *—$C(R_9)$—*', *—$C(R_9)$=$C(R_{10})$—*', *—$C(=O)$—*', *—$C(=S)$—*', *—C≡C—*', *—$N(R_9)$—*', *—$Si(R_9)(R_{10})$—', and *—$P(R_9)(R_{10})$—*', wherein $R_9$ and $R_{10}$ are the same as described above.

$CY_5$ in Formula 1 may be a 5-membered ring including $X_{51}$ and $X_{52}$.

In one or more embodiments, a bond between $X_{51}$ and $X_{52}$ in Formula 1 may be a double bond.

In one or more embodiments, $X_{51}$ in Formula 1 may be selected from N, $N(R_{51})$, and $C(R_{51})$, and $X_{52}$ may be selected from N, $N(R_{53})$, and $C(R_{53})$, but embodiments of the present disclosure are not limited thereto.

In one or more embodiments, in Formula 1, $X_{51}$ may be N and $X_{52}$ may be $C(R_{53})$;

$X_{51}$ may be $C(R_{51})$ and $X_{52}$ may be N; or $X_{51}$ may be $C(R_{51})$ and $X_{52}$ may be $C(R_{53})$, but embodiments of the present disclosure are not limited thereto.

$R_1$ to $R_6$ and $R_{51}$ to $R_{54}$ in Formula 1 may each independently be selected from hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$. $Q_1$ to $Q_9$ are the same as described above.

For example, $R_1$ to $R_6$ and $R_{51}$ to $R_{54}$ in Formula 1 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl (adamantyl) group, a norbornanyl (norbornyl) group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_8$)($Q_7$), and —P(=O)($Q_8$)($Q_9$), wherein $Q_1$ to $Q_9$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In one or more embodiments, $R_1$ to $R_6$ and $R_{51}$ to $R_{54}$ in Formula 1 may each independently be selected from:

hydrogen, deuterium, —F, a cyano group, a nitro group, —SF$_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a quinolinyl group, an isoquinolinyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a quinolinyl group, an isoquinolinyl group, a carbazolyl group, a dibenzofuranyl group, and a dibenzothiophenyl group, each substituted with at least one selected from deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ may each independently be selected from:

—CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

In one or more embodiments, $R_1$ to $R_6$ and $R_{51}$ to $R_{54}$ in Formula 1 may each independently be selected from hydrogen, deuterium, —F, a cyano group, a nitro group, —SF$_5$, —CH₃, —CD₃, —CD₂H, —CDH₂, —CF₃, —CF₂H, —CFH₂, groups represented by Formulae 9-1 to 9-19, groups represented by Formulae 10-1 to 10-48, and —Si(Q₃)(Q₄)(Q₅), but embodiments of the present disclosure are not limited thereto:
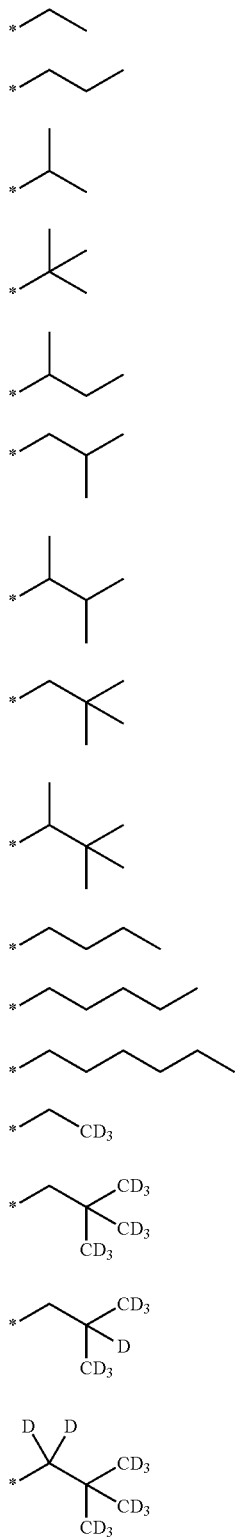
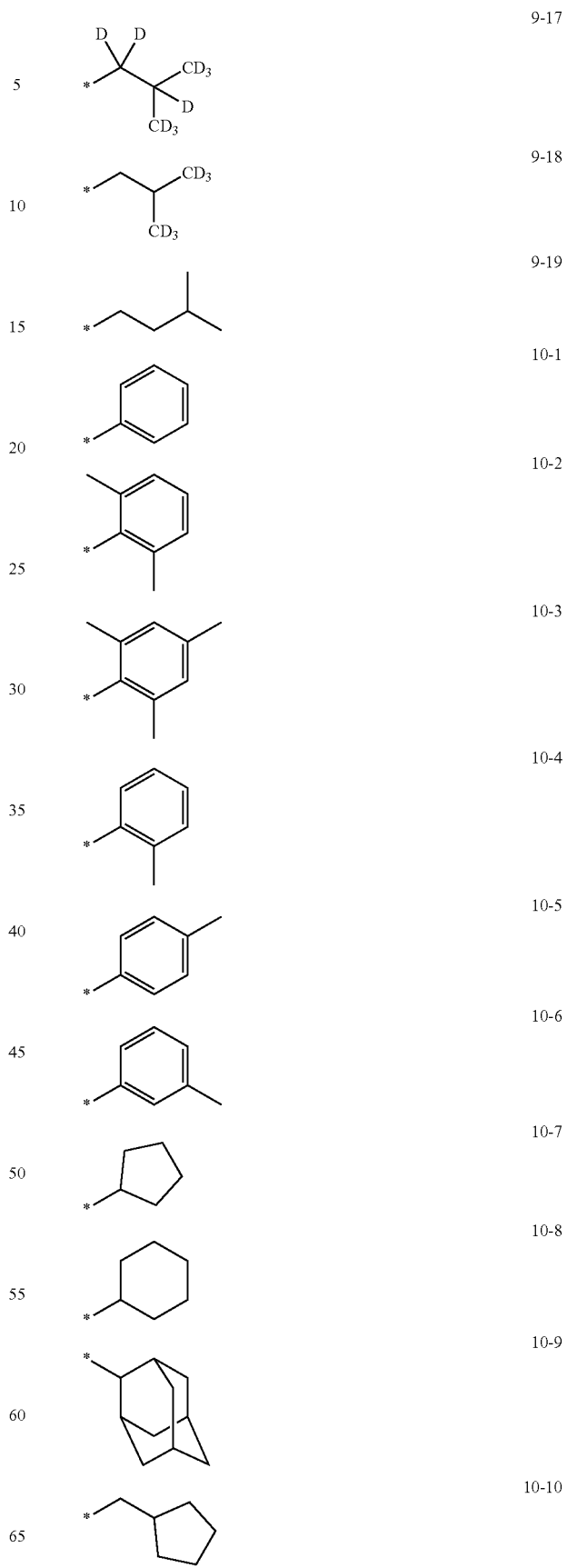

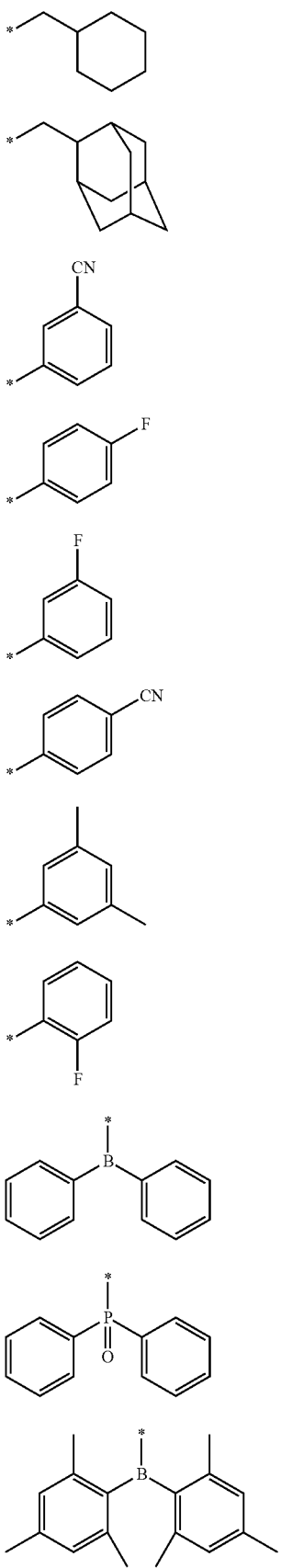
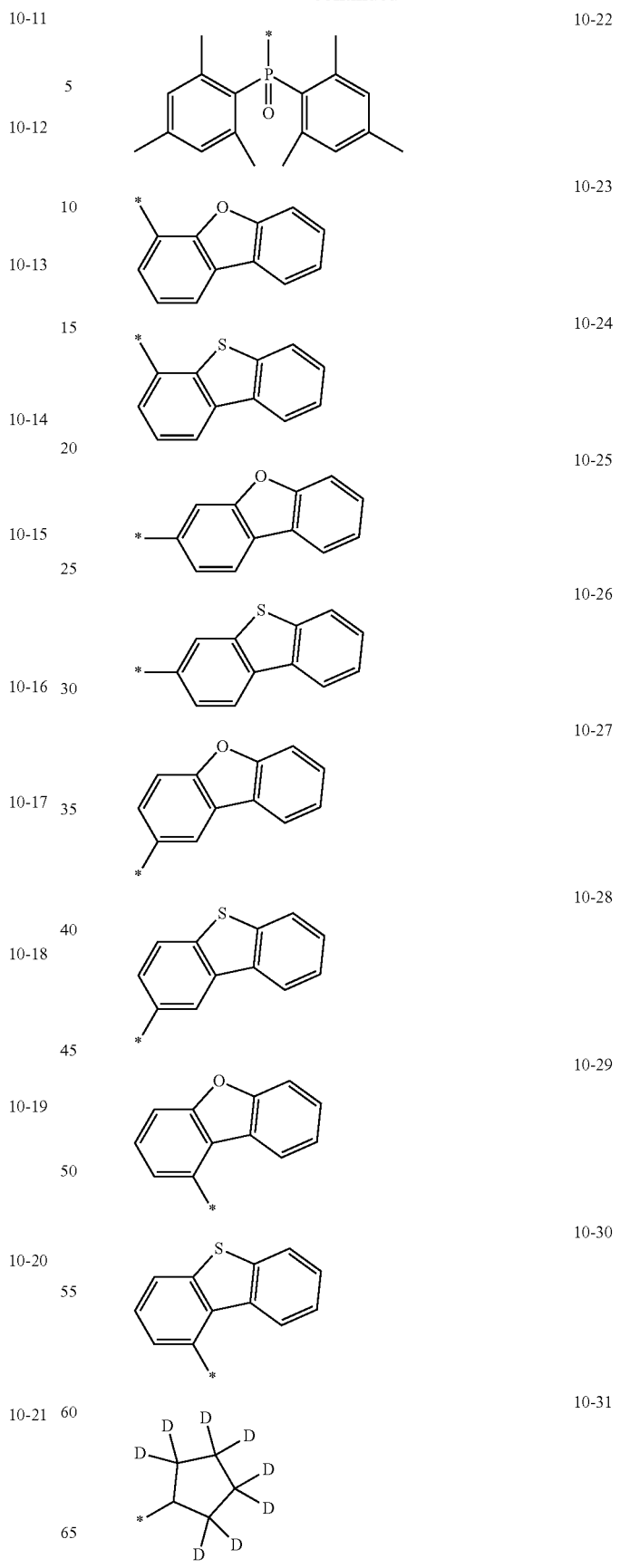

-continued
10-32 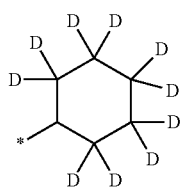
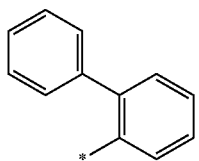  10-33
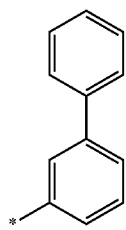  10-34
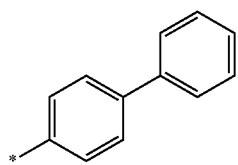  10-35
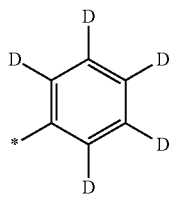  10-36
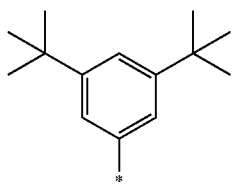  10-37
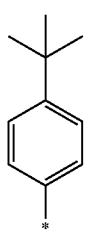  10-38
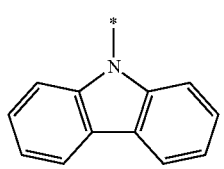  10-39
-continued
10-40 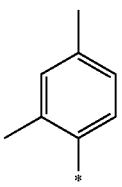
10-41 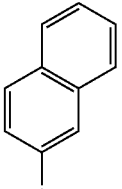
10-42 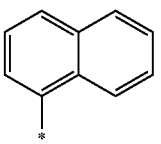
10-43 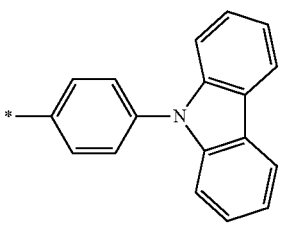
10-44 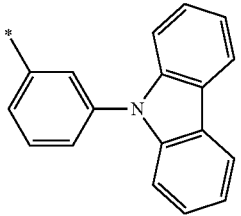
10-45 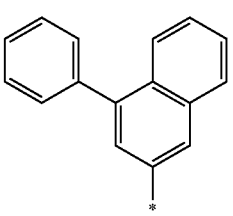
10-46 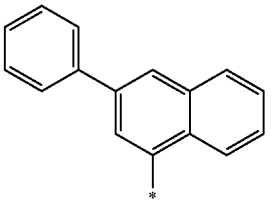
10-47 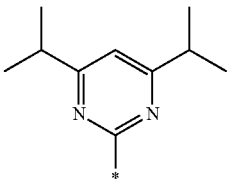

-continued

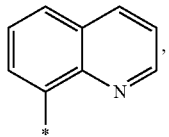

10-48 wherein * in Formulae 9-1 to 9-19 and 10-1 to 10-48 indicates a binding site to a neighboring atom. $Q_3$ to $Q_5$ are the same as described above.

a1, a2, a3, and a4 in Formula 1 respectively indicate the number of groups $R_1$, the number of groups $R_2$, the number of groups $R_3$, and the number of groups $R_4$, and may each independently be 0, 1, 2, 3, 4, or 5. When a1 is two or more, two or more groups $R_1$ may be identical to or different from each other, when a2 is two or more, two or more groups $R_2$ may be identical to or different from each other, when a3 is two or more, two or more groups $R_3$ may be identical to or different from each other, and when a4 is two or more, two or more groups $R_4$ may be identical to or different from each other, but embodiments of the present disclosure are not limited thereto.

Two of groups $R_1$ in the number of a1 in Formula 1 may optionally be linked to form a substituted or unsubstituted $C_5$-$C_{30}$ carbocyclic group or a substituted or unsubstituted $C_1$-$C_{30}$ heterocyclic group, two of groups $R_2$ in the number of a2 may optionally be linked to form a substituted or unsubstituted $C_5$-$C_{30}$ carbocyclic group or a substituted or unsubstituted $C_1$-$C_{30}$ heterocyclic group, two of groups $R_3$ in the number of a3 may optionally be linked to form a substituted or unsubstituted $C_5$-$C_{30}$ carbocyclic group or a substituted or unsubstituted $C_1$-$C_{30}$ heterocyclic group, two of groups $R_4$ in the number of a4 may optionally be linked to form a substituted or unsubstituted $C_5$-$C_{30}$ carbocyclic group or a substituted or unsubstituted $C_1$-$C_{30}$ heterocyclic group, and two or more neighboring groups selected from $R_1$ to $R_4$ may optionally be selected from a substituted or unsubstituted $C_5$-$C_{30}$ carbocyclic group or a substituted or unsubstituted $C_1$-$C_{30}$ heterocyclic group.

For example, a substituted or unsubstituted $C_5$-$C_{30}$ carbocyclic group or a substituted or unsubstituted $C_1$-$C_{30}$ heterocyclic group, which may be formed by optionally linking two of groups $R_1$ in the number of a1, two of groups $R_2$ in the number of a2, two of groups $R_3$ in the number of a3, two of groups $R_4$ in the number of a4, or two or more neighboring groups selected from $R_1$ to $R_4$ in Formula 1, may be selected from:

a pentadiene group, a cyclohexane group, an adamantane group, a bicyclo[2.2.1]heptane group, a benzene group, a furan group, a pyridine group, a pyrimidine group, a pyrazine group, a pyridazine group, a pyrrole group, a naphthalene group, an anthracene group, a tetracene group, a phenanthrene group, a dihydronaphthalene group, a phenalene group, a benzothiophene group, a benzofuran group, an indene group, and an indole group; and a pentadiene group, a cyclohexane group, an adamantane group, a bicyclo[2.2.1]heptane group, a benzene group, a furan group, a pyridine group, a pyrimidine group, a pyrazine group, a pyridazine group, a pyrrole group, a naphthalene group, an anthracene group, a tetracene group, a phenanthrene group, a dihydronaphthalene group, a phenalene group, a benzothiophene group, a benzofuran group, an indene group, and an indole group, each substituted with at least one $R_{1a}$, but embodiments of the present disclosure are not limited thereto.

$R_{1a}$ is the same as described above in connection with $R_1$.

"An azabenzothiophene, an azabenzofuran, an azaindene, an azaindole, an azabenzosilole, an azadibenzothiophene, an azadibenzofuran, an azafluorene, an azacarbazole, and an azadibenzosilole" as described herein may mean hetero rings that respectively have the same backbones as "a benzothiophene, a benzofuran, an indene, an indole, an azabenzosilole, a dibenzothiophene, a dibenzofuran, a fluorene, a carbazole, and a dibenzosilole", in which at least one carbon atom forming a ring thereof is substituted with nitrogen.

In one or more embodiments, a moiety represented by in

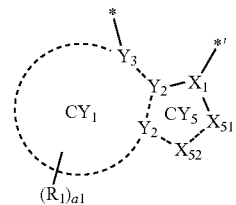

Formula 1 may be a group represented by Formula CY1-1:

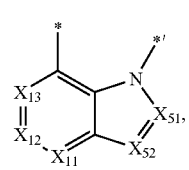

CY1-1 wherein, in Formula CY1-1,
$X_{51}$ and $X_{52}$ are the same as described above,
$X_{11}$ may be N or $C(R_{11})$, $X_{12}$ may be N or $C(R_{12})$, and $X_{13}$ may N or $C(R_{13})$,
$R_{11}$ to $R_{13}$ are each independently the same as described above in connection with $R_1$, and
* and *' each indicate a binding site to a neighboring atom.

For example, in Formula CY1-1, $X_{11}$ may be $C(R_{11})$, $X_{12}$ may be $C(R_{12})$, and $X_{13}$ may be $C(R_{13})$, but embodiments of the present disclosure are not limited thereto.

In one or more embodiments, a moiety represented by

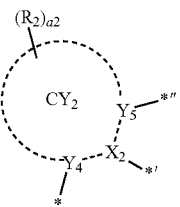

in Formula 1 may be selected from groups represented by Formulae CY2-1 to CY2-6:

CY2-1

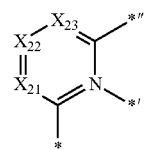

-continued

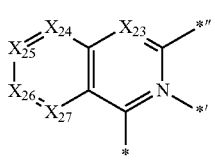
CY2-2

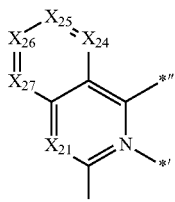
CY2-3

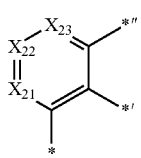
CY2-4

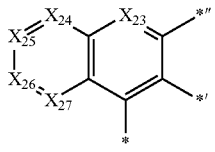
CY2-5

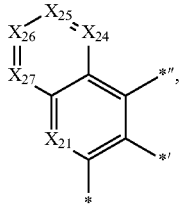
CY2-6 wherein, in Formulae CY2-1 to CY2-6, $X_{21}$ may be N or $C(R_{21})$, $X_{22}$ may be N or $C(R_{22})$, $X_{23}$ may be N or $C(R_{23})$, $X_{24}$ may be N or $C(R_{24})$, $X_{25}$ may be N or $C(R_{25})$, $X_{26}$ may be N or $C(R_{26})$, and $X_{27}$ may be N or $C(R_{27})$, $R_{21}$ to $R_{27}$ are each independently the same as described above in connection with $R_2$, and \*, \*', and \*" each indicate a binding site to a neighboring atom.

For example, in Formulae CY2-1 to CY2-6, $X_{21}$ may be $C(R_{21})$, $X_{22}$ may be $C(R_{22})$, $X_{23}$ may be $C(R_{23})$, $X_{24}$ may be $C(R_{24})$, $X_{25}$ may be $C(R_{25})$, $X_{26}$ may be $C(R_{26})$, and $X_{27}$ may be $C(R_{27})$, but embodiments of the present disclosure are not limited thereto.

In one or more embodiments, a moiety represented by

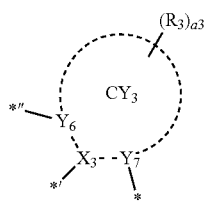

in Formula 1 may be selected from groups represented by Formulae CY3-1 to CY3-22:

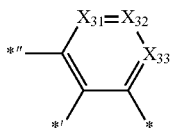
CY3-1

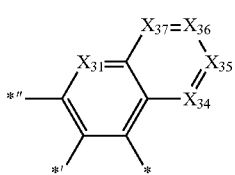
CY3-2

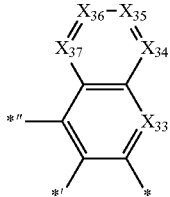
CY3-3

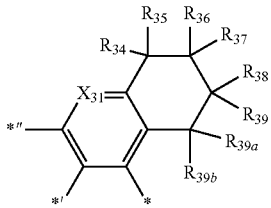
CY3-4

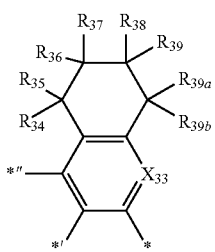
CY3-5

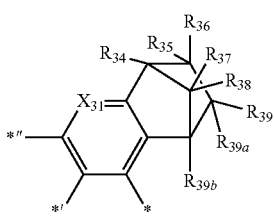
CY3-6

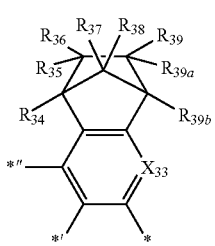
CY3-7

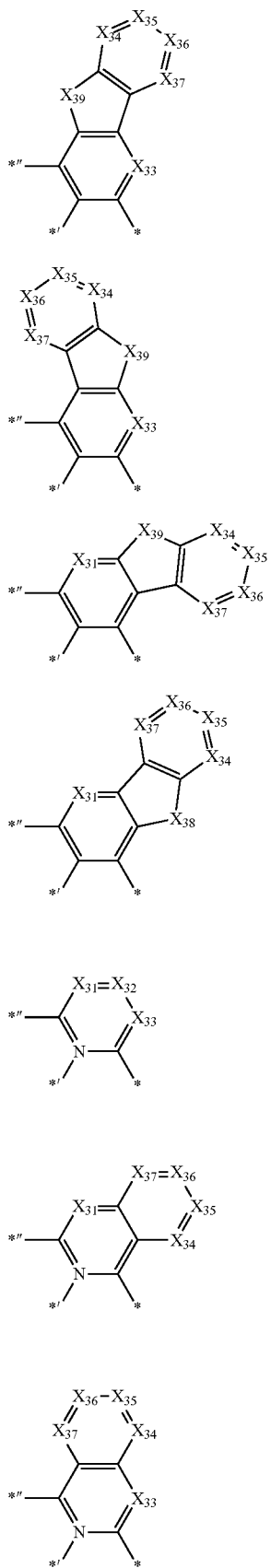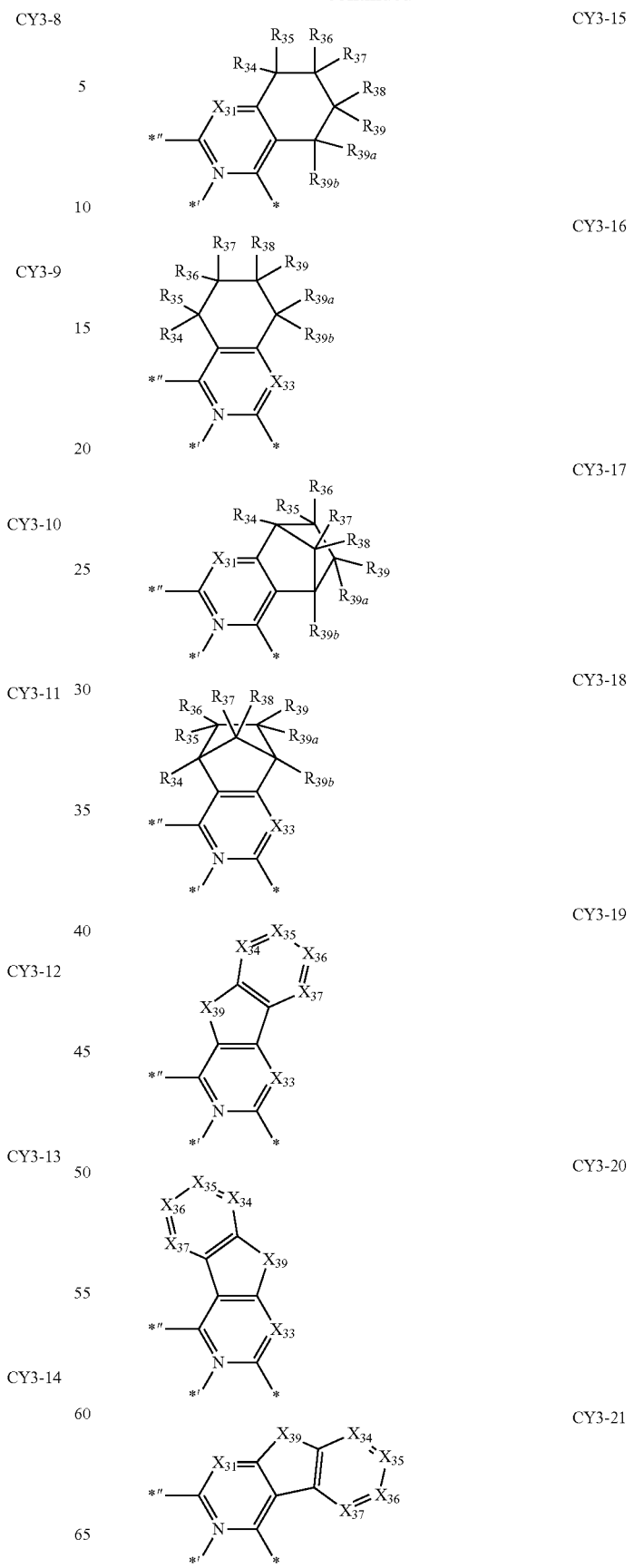

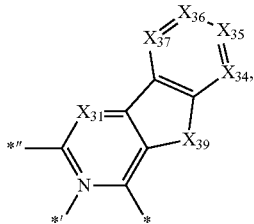

CY3-22

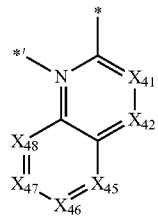

CY4-4 wherein, in Formulae CY3-1 to CY3-22, $X_{31}$ may be N or $C(R_{31})$, $X_{32}$ may be N or $C(R_{32})$, $X_{33}$ may be N or $C(R_{33})$, $X_{34}$ may be N or $C(R_{34})$, $X_{35}$ may be N or $C(R_{35})$, $X_{36}$ may be N or $C(R_{36})$, and $X_{37}$ may be N or $C(R_{37})$, $X_{39}$ may be $C(R_{39a})(R_{39b})$ $N(R_{39})$, O, S, or $Si(R_{39a})(R_{39b})$, $R_{31}$ to $R_{39}$, $R_{39a}$, and $R_{33b}$ are each independently the same as described above in connection with $R_3$, and \*, \*', and \*'' each indicate a binding site to a neighboring atom.

For example, in Formulae CY3-1 to CY3-22, $X_{31}$ may be $C(R_{31})$, $X_{32}$ may be $C(R_{32})$, $X_{33}$ may be $C(R_{33})$, $X_{34}$ may be $C(R_{34})$, $X_{35}$ may be $C(R_{35})$, $X_{36}$ may be $C(R_{36})$, and $X_{37}$ may be $C(R_{37})$, but embodiments of the present disclosure are not limited thereto.

In one or more embodiments, a moiety represented by

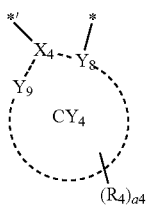

in Formula 1 may be selected from groups represented by Formulae CY4-1 to CY4-8:

CY4-1

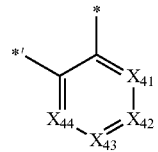

CY4-5

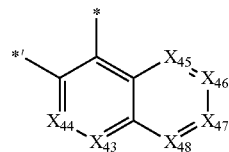

CY4-6

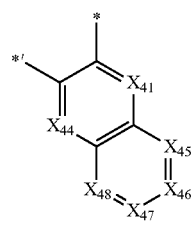

CY4-2

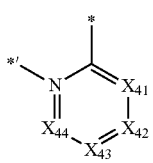

CY4-7

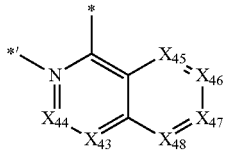

CY4-3

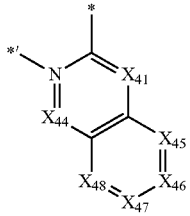

CY4-8

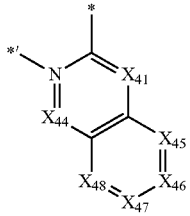

wherein, in Formulae CY4-1 to CY4-8, $X_{41}$ may be N or $C(R_{41})$, $X_{42}$ may be N or $C(R_{42})$, $X_{43}$ may be N or $C(R_{43})$, $X_{44}$ may be N or $C(R_{44})$, $X_{45}$ may be N or $C(R_{45})$, $X_{46}$ may be N or $C(R_{46})$, $X_{47}$ may be N or $C(R_{47})$, and $X_{48}$ may be N or $C(R_{48})$, $R_{41}$ to $R_{48}$ are each independently the same as described above in connection with $R_4$, and \* and \*' each indicate a binding site to a neighboring atom.

For example, in Formulae CY4-1 to CY4-8, $X_{41}$ may be $C(R_{41})$, $X_{42}$ may be $C(R_{42})$, $X_{43}$ may be $C(R_{43})$, $X_{44}$ may be $C(R_{44})$, $X_{45}$ may be $C(R_{45})$, $X_{46}$ may be $C(R_{46})$, $X_{47}$ may be $C(R_{47})$, and $X_{48}$ may be $C(R_{48})$, but embodiments of the present disclosure are not limited thereto.

For example, in Formula 1,
a moiety represented by

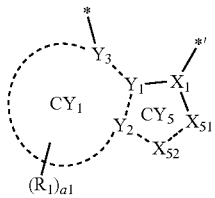

may be a group represented by Formula CY1-1,
a moiety represented by

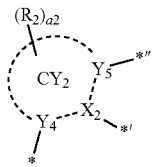

may be a group represented by Formula CY2-1,
a moiety represented by

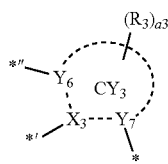

may be selected from groups represented by Formulae CY3-1 and CY3-8 to CY3-11, and
a moiety represented by

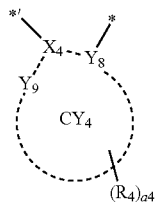

may be a group represented by Formula CY4-1, but embodiments of the present disclosure are not limited thereto.

In one or more embodiments, the organometallic compound may be represented by Formula 1-1:

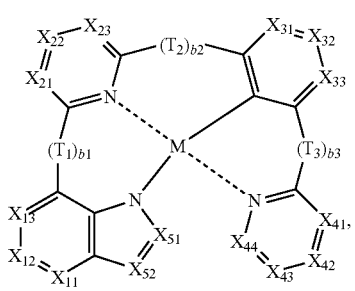

Formula 1-1 wherein, in Formula 1-1,
M, $T_1$ to $T_3$, b1 to b3, $X_{51}$, and $X_{52}$ are the same as described above,
$X_{11}$ may be N or $C(R_{11})$, $X_{12}$ may be N or $C(R_{12})$, $X_{13}$ may be N or $C(R_{13})$, $X_{21}$ may be N or $C(R_{21})$, $X_{22}$ may be N or $C(R_{22})$, $X_{23}$ may be N or $C(R_{23})$, $X_{31}$ may be N or $C(R_{31})$, $X_{32}$ may be N or $C(R_{32})$, $X_{33}$ may be N or $C(R_{33})$, $X_{41}$ may be N or $C(R_{41})$, $X_{42}$ may be N or $C(R_{42})$, $X_{43}$ may be N or $C(R_{43})$, and $X_{44}$ may be N or $C(R_{44})$,
$R_{11}$ to $R_{13}$ are each independently the same as described above in connection with $R_1$, and two of $R_{11}$ to $R_{13}$ may optionally be linked to form a substituted or unsubstituted $C_5$-$C_{30}$ carbocyclic group or a substituted or unsubstituted $C_1$-$C_{30}$ heterocyclic group,
$R_{21}$ to $R_{23}$ are each independently the same as described above in connection with $R_2$, and two of $R_{21}$ to $R_{23}$ may optionally be linked to form a substituted or unsubstituted $C_5$-$C_{30}$ carbocyclic group or a substituted or unsubstituted $C_1$-$C_{30}$ heterocyclic group,
$R_{31}$ to $R_{33}$ are each independently the same as described above in connection with $R_3$, and two of $R_{31}$ to $R_{33}$ may optionally be linked to form a substituted or unsubstituted $C_5$-$C_{30}$ carbocyclic group or a substituted or unsubstituted $C_1$-$C_{30}$ heterocyclic group,
$R_{41}$ to $R_{44}$ are each independently the same as described above in connection with $R_4$, and two of $R_{41}$ to $R_{44}$ may optionally be linked to form a substituted or unsubstituted $C_5$-$C_{30}$ carbocyclic group or a substituted or unsubstituted $C_1$-$C_{30}$ heterocyclic group, and
two of $R_{11}$ to $R_{13}$, $R_{21}$ to $R_{23}$, $R_{31}$ to $R_{33}$, and $R_{41}$ to $R_{44}$ may optionally be linked to form a substituted or unsubstituted $C_5$-$C_{30}$ carbocyclic group or a substituted or unsubstituted $C_1$-$C_{30}$ heterocyclic group.

For example, in Formula 1-1,
$X_{11}$ may be $C(R_{11})$, $X_{12}$ may be $C(R_{12})$, $X_{13}$ may be $C(R_{13})$, $X_{21}$ may be $C(R_{21})$, $X_{22}$ may be $C(R_{22})$, $X_{23}$ may be $C(R_{23})$, $X_{31}$ may be $C(R_{31})$, $X_{32}$ may be $C(R_{32})$, $X_{33}$ may be $C(R_{33})$, $X_{41}$ may be $C(R_{41})$, $X_{42}$ may be $C(R_{42})$, $X_{43}$ may be $C(R_{43})$, and $X_{44}$ may be $C(R_{44})$, and
$R_{11}$ to $R_{13}$, $R_{21}$ to $R_{23}$, $R_{31}$ to $R_{33}$, and $R_{41}$ to $R_{44}$ may each independently be selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-48, and —$Si(Q_3)(Q_4)(Q_5)$, but embodiments of the present disclosure are not limited thereto.

For example, a substituted or unsubstituted $C_5$-$C_{30}$ carbocyclic group or a substituted or unsubstituted $C_1$-$C_{30}$ heterocyclic group, which may be formed by optionally linking two of $R_{11}$ to $R_{13}$, two of $R_{21}$ to $R_{23}$, two of $R_{31}$ to $R_{33}$, two of $R_{41}$ to $R_{44}$, or two of $R_{11}$ to $R_{13}$, $R_{21}$ to $R_{23}$, $R_{31}$ to $R_{33}$, and $R_{41}$ to $R_{44}$ in Formula 1-1, may be selected from:
a pentadiene group, a cyclohexane group, an adamantane group, a bicyclo[2.2.1]heptane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, and an indole group; and
a pentadiene group, a cyclohexane group, an adamantane group, a bicyclo[2.2.1]heptane group, a benzene group, a pyridine group, a pyrimidine group, a pyrazine group, a pyridazine group, a naphthalene group, an anthracene group, a tetracene group, a phenanthrene group, a dihydronaphthalene group, a phenalene group, a benzothiophene group, a benzofuran group, an indene group, and an indole group, each substituted with at least one $R_{1a}$, but embodiments of the present disclosure are not limited thereto.

$R_{1a}$ is the same as described above in connection with $R_1$.

In one or more embodiments, the organometallic compound may be represented by Formula 1-1A:

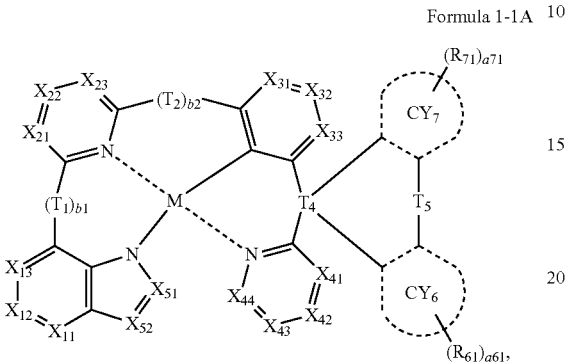

Formula 1-1A wherein, in Formula 1-1A,

M, $T_1$, $T_2$, b1, b2, $X_{51}$, and $X_{52}$ are the same as described above, $X_{11}$ may be N or $C(R_{11})$, $X_{12}$ may be N or $C(R_{12})$, $X_{13}$ may be N or $C(R_{13})$, $X_{21}$ may be N or $C(R_{21})$, $X_{22}$ may be N or $C(R_{22})$, $X_{23}$ may be N or $C(R_{23})$, $X_{31}$ may be N or $C(R_{31})$, $X_{32}$ may be N or $C(R_{32})$, $X_{33}$ may be N or $C(R_{33})$, $X_{41}$ may be N or $C(R_{41})$, $X_{42}$ may be N or $C(R_{42})$, $X_{43}$ may be N or $C(R_{43})$, and $X_{44}$ may be N or $C(R_{44})$, $R_{11}$ to $R_{13}$ are each independently the same as described above in connection with $R_1$, and two of $R_{11}$ to $R_{13}$ may optionally be linked to form a substituted or unsubstituted $C_5$-$C_{30}$ carbocyclic group or a substituted or unsubstituted $C_1$-$C_{30}$ heterocyclic group, $R_{21}$ to $R_{23}$ are each independently the same as described above in connection with $R_2$, and two of $R_{21}$ to $R_{23}$ may optionally be linked to form a substituted or unsubstituted $C_5$-$C_{30}$ carbocyclic group or a substituted or unsubstituted $C_1$-$C_{30}$ heterocyclic group, $R_{31}$ to $R_{33}$ are each independently the same as described above in connection with $R_3$, and two of $R_{31}$ to $R_{33}$ may optionally be linked to form a substituted or unsubstituted $C_5$-$C_{30}$ carbocyclic group or a substituted or unsubstituted $C_1$-$C_{30}$ heterocyclic group, $R_{41}$ to $R_{44}$ are each independently the same as described above in connection with $R_4$, and two of $R_{41}$ to $R_{44}$ may optionally be linked to form a substituted or unsubstituted $C_5$-$C_{30}$ carbocyclic group or a substituted or unsubstituted $C_1$-$C_{30}$ heterocyclic group, two of $R_{11}$ to $R_{13}$, $R_{21}$ to $R_{23}$, $R_{31}$ to $R_{33}$, and $R_{41}$ to $R_{44}$ may optionally be linked to form a substituted or unsubstituted $C_5$-$C_{30}$ carbocyclic group or a substituted or unsubstituted $C_1$-$C_{30}$ heterocyclic group, $R_{61}$ and $R_{71}$ are each independently the same as described above in connection with $R_1$, a61 and a71 may each independently be 0, 1, 2, or 3, $T_4$ may be C, Si, or P, $T_5$ may be a single bond, *—O—*', *—S—*', *—C($R_7$)($R_8$)—*', *—C($R_7$)=*', *=C($R_8$)—*', *—C($R_7$)=C($R_8$)—*', *—C(=O)—*', *—C(=S)—*', *—C≡C—*', *—N($R_7$)—*', *—Si($R_7$)($R_8$)—*', and *—P($R_7$)($R_8$)—*', $R_7$ and $R_8$ are the same as described above in connection with $R_5$, and

* and *' each indicate a binding site to a neighboring atom.

The organometallic compound may be represented by one of Formulae 1(1) to 1(20):

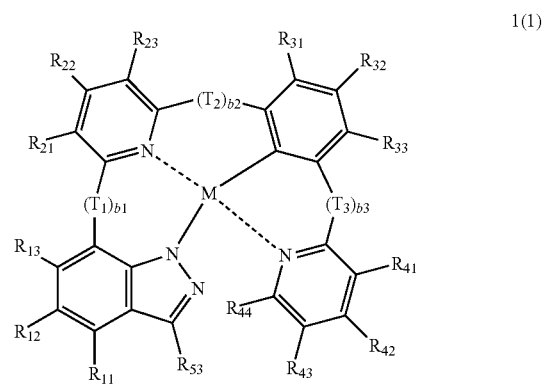

1(1)

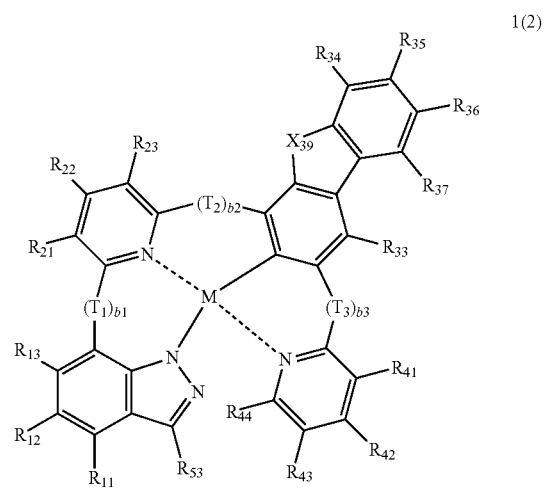

1(2)

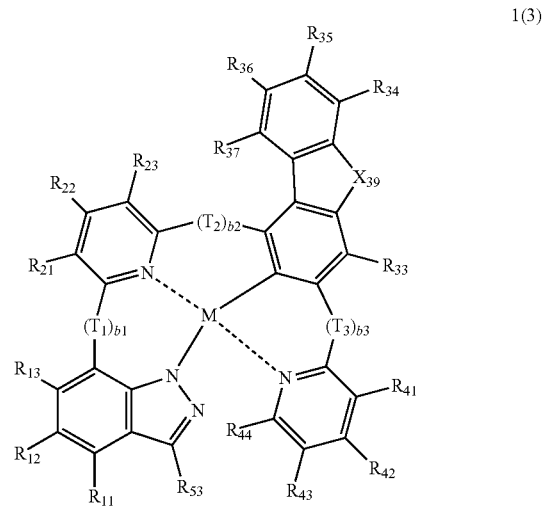

1(3)

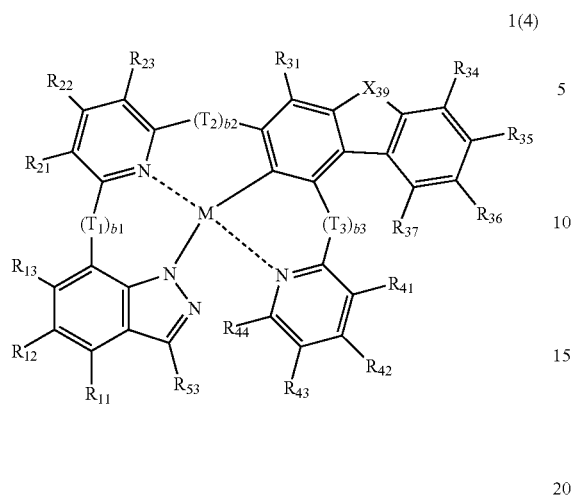
1(4)
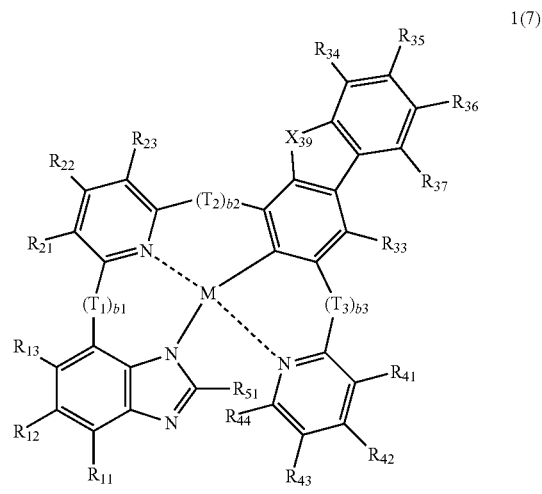
1(7)
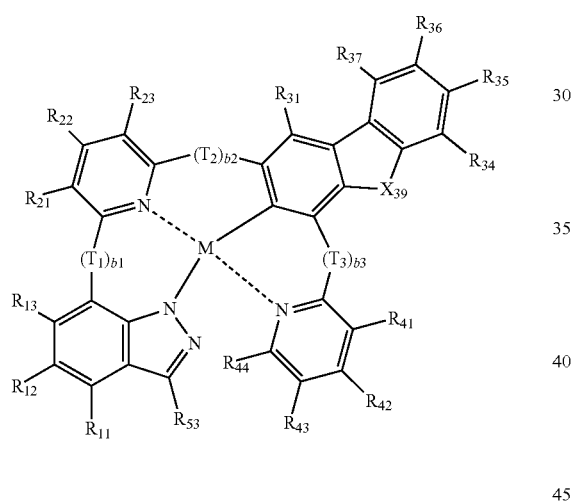
1(5)
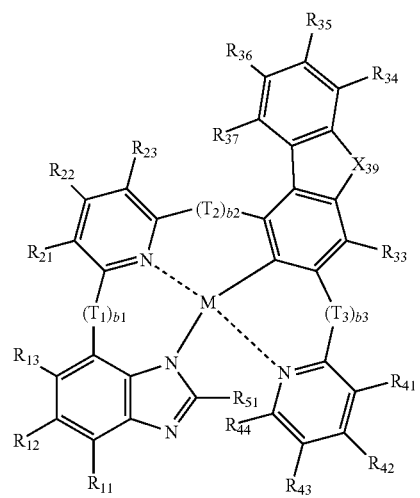
1(8)
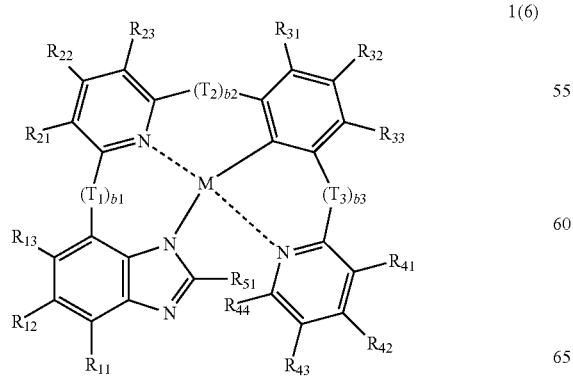
1(6)
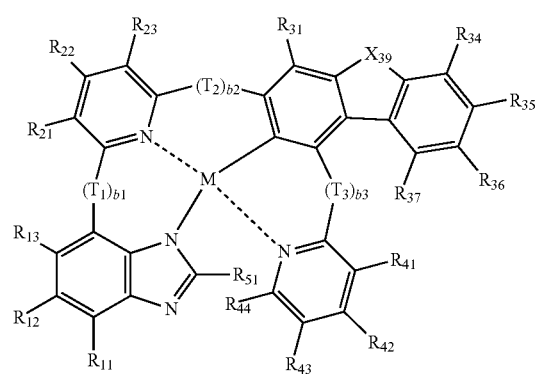
1(9)

1(10) 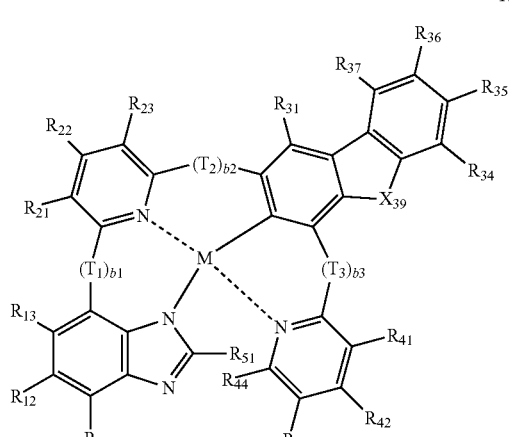
1(11) 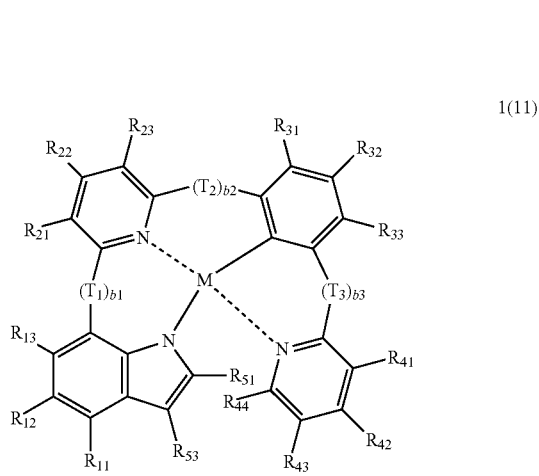
1(12) 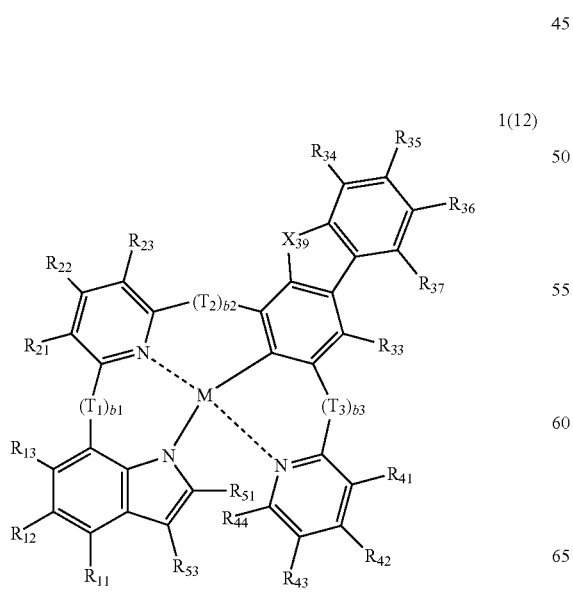
1(13) 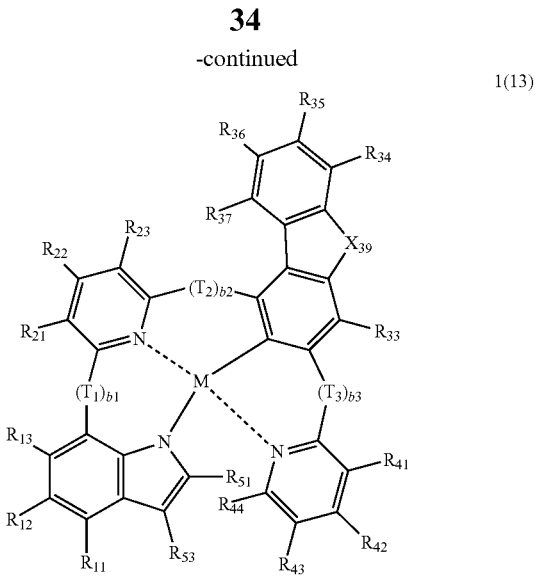
1(14) 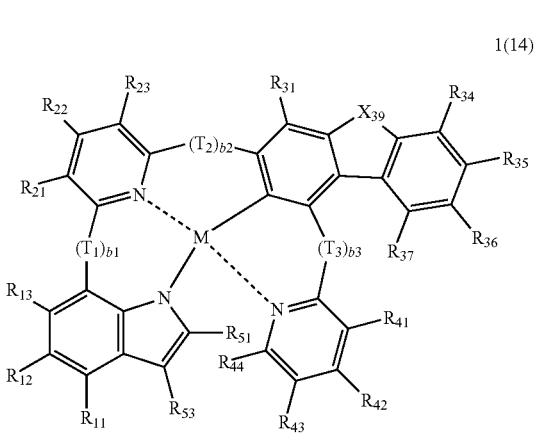
1(15) 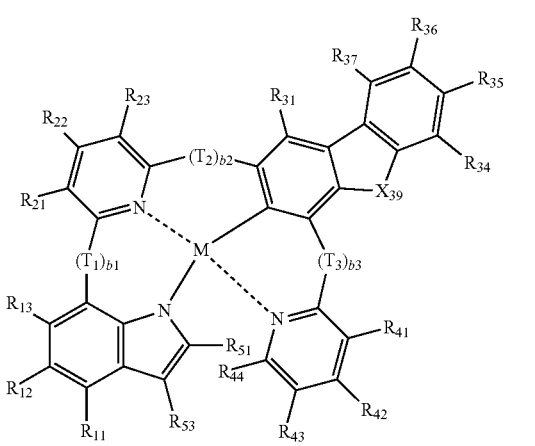

1(16)
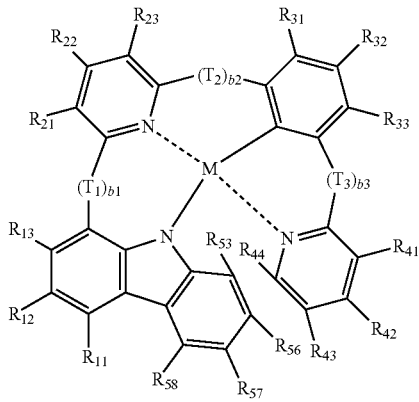

1(17)
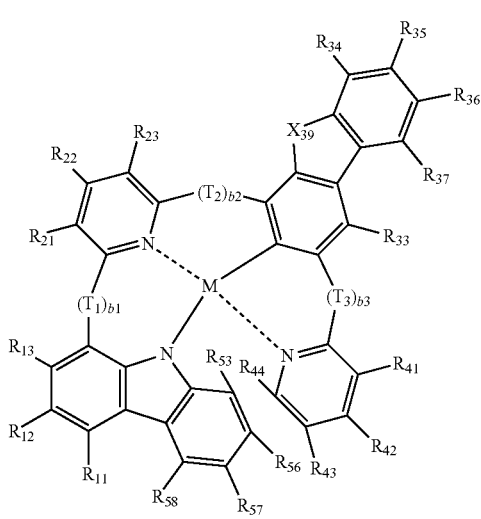

1(18)
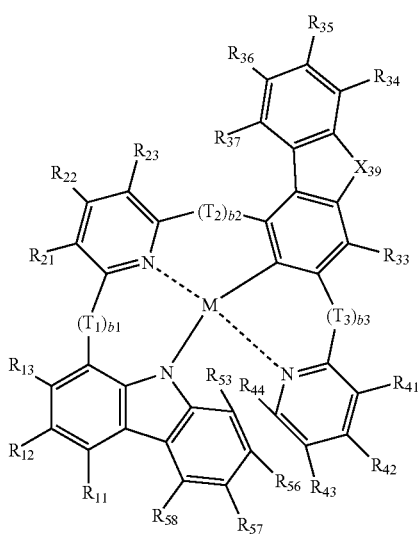

1(19)
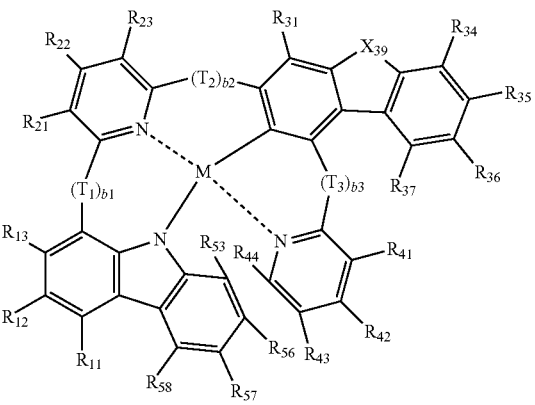

1(20)
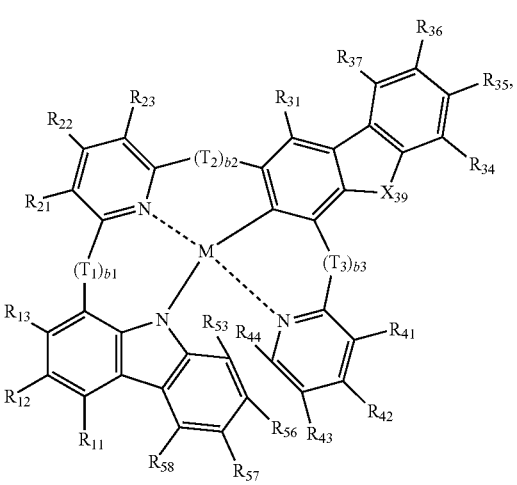

wherein, in Formulae 1(1) to 1(20),

M, $T_1$ to $T_3$, and b1 to b3 are the same as described above, $X_{39}$ may be $C(R_{39a})(R_{39b})$, $N(R_{39})$, O, S, or $Si(R_{39a})(R_{39b})$, $R_{11}$ to $R_{13}$ are each independently the same as described above in connection with $R_1$, $R_{21}$ to $R_{23}$ are each independently the same as described above in connection with $R_2$, $R_{31}$ to $R_{37}$, $R_{39}$, $R_{39a}$, and $R_{39b}$ are each independently the same as described above in connection with $R_3$, and $R_{41}$ to $R_{44}$ may be understood by referring to the description provided herein in connection with $R_4$.

In one or more embodiments, the organometallic compound may be one of Compounds 1 to 132:
1
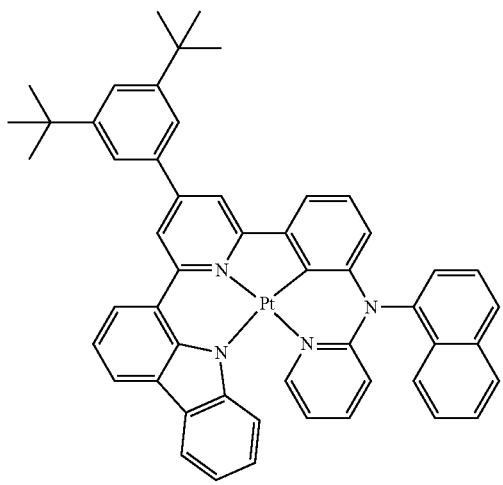
2
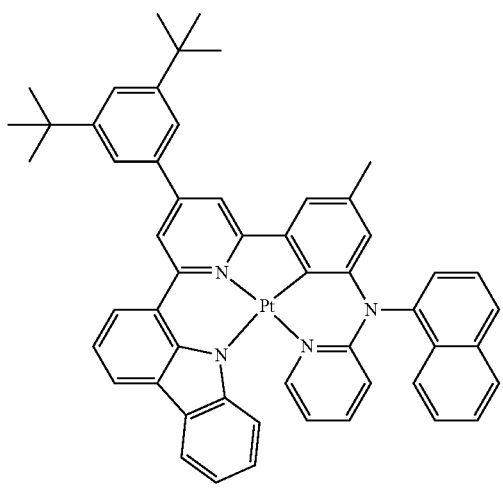
3
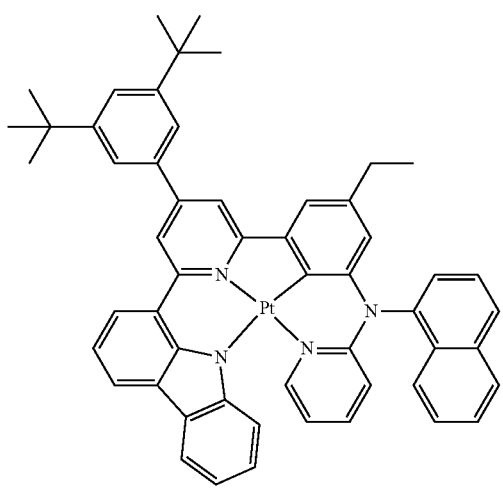
4
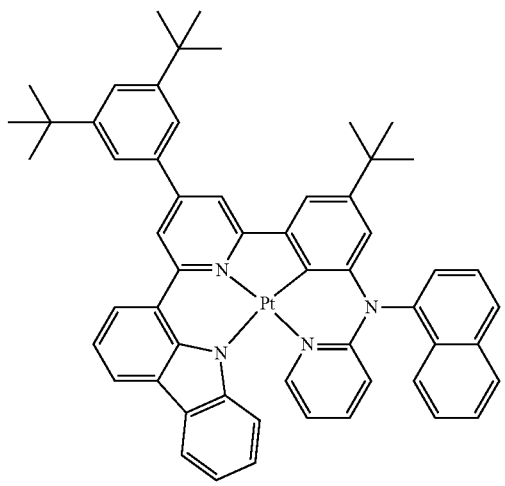
5
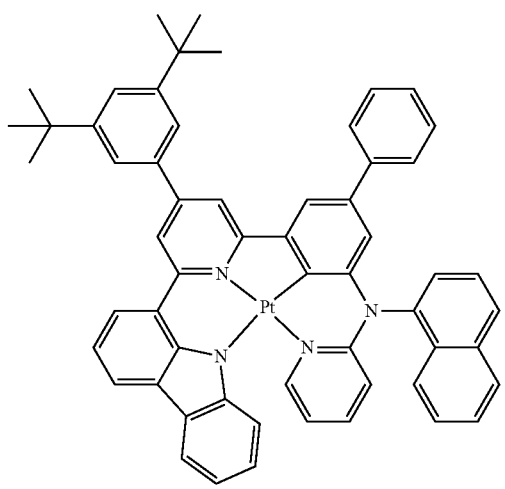
6
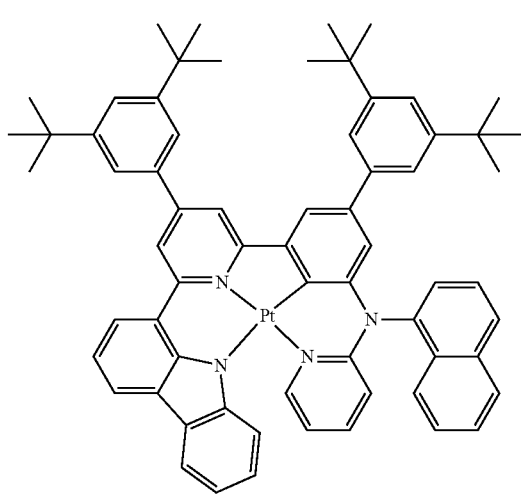

7
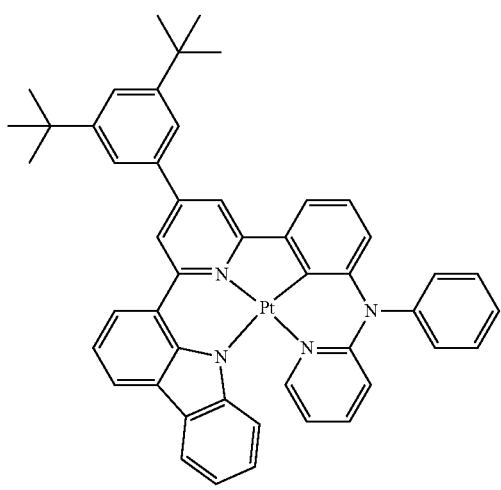
10
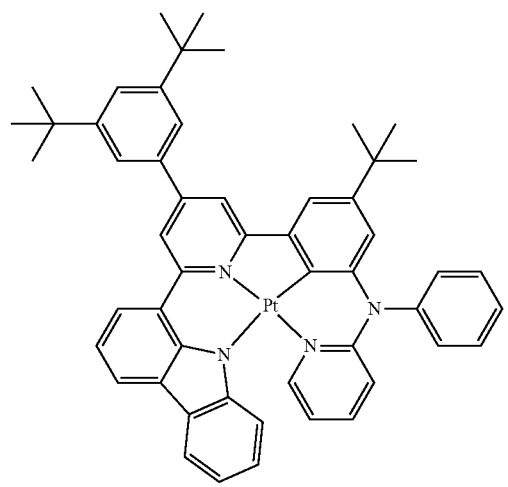
8
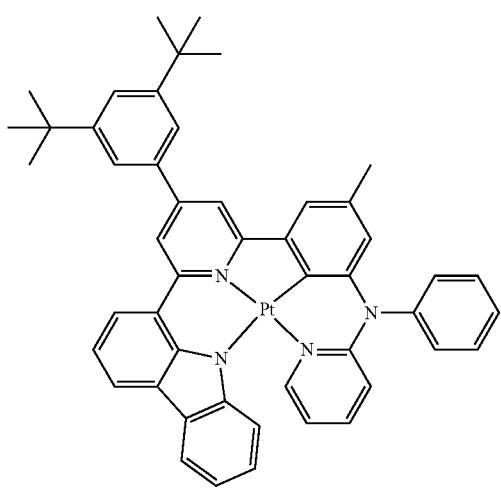
11
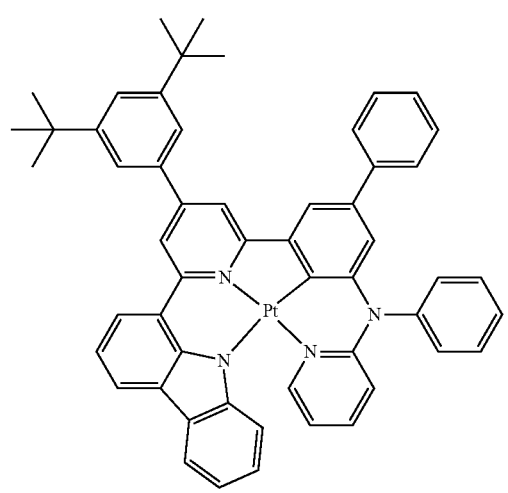
9
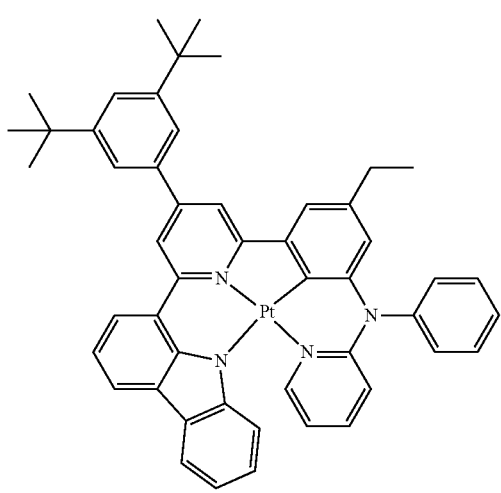
12
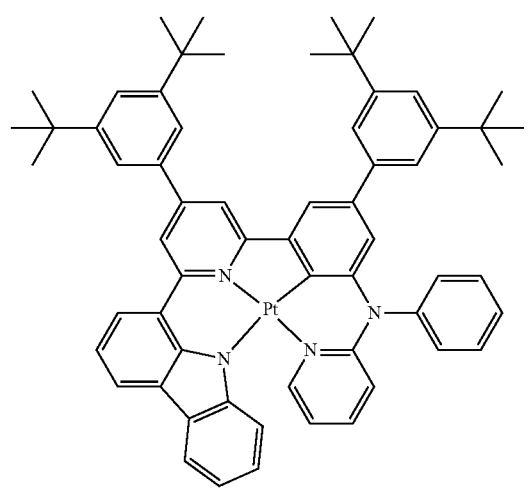

13
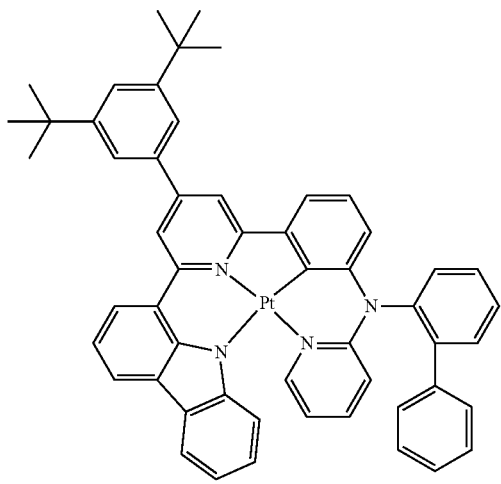
14
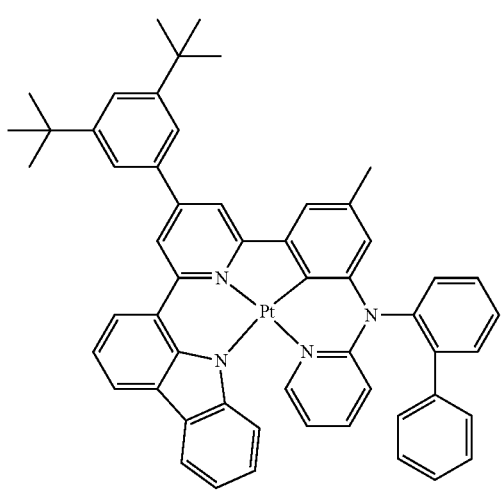
15
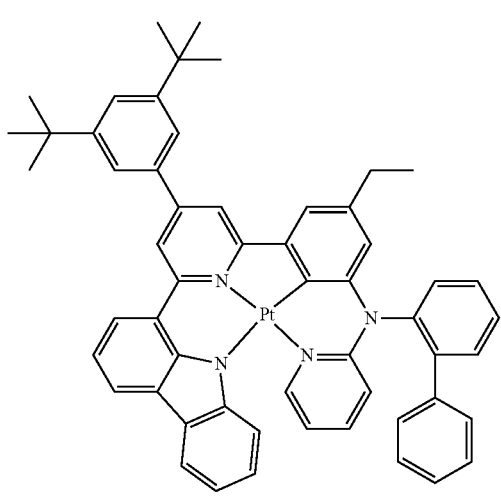
16
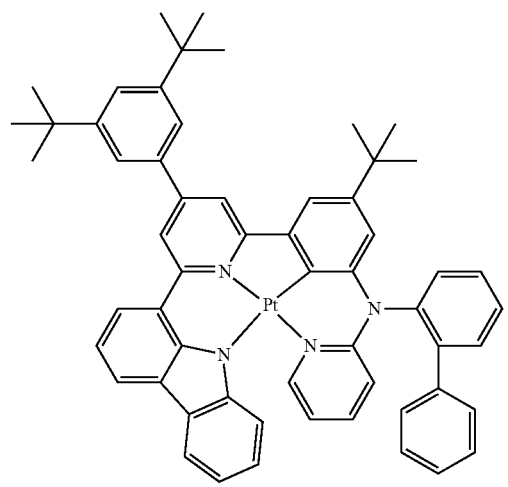
17
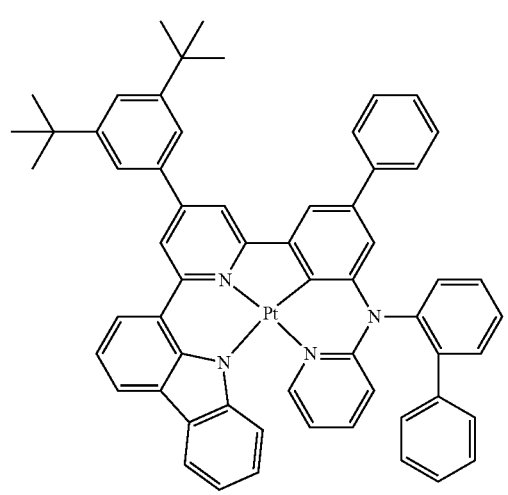
18
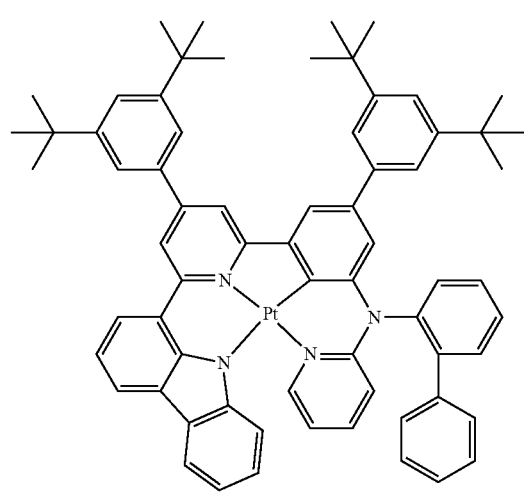

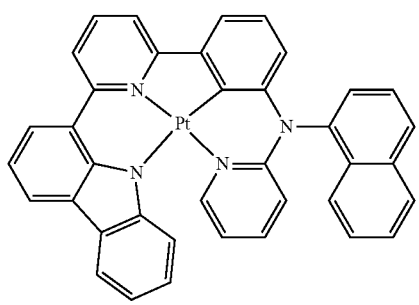
19
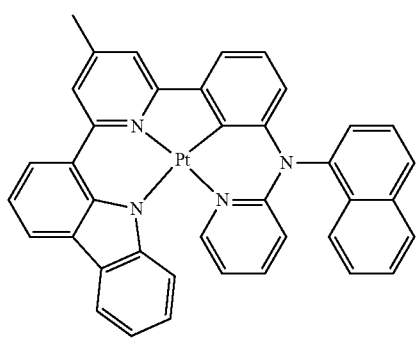
20
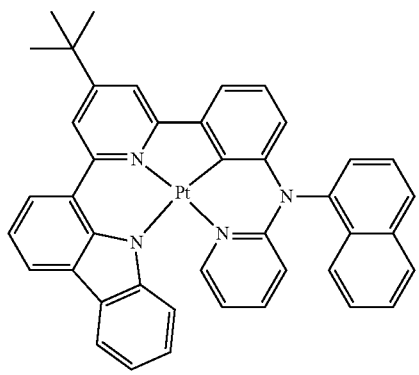
21
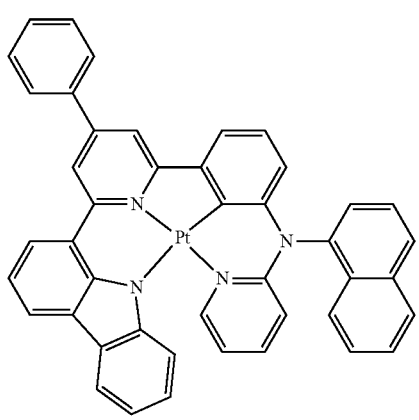
22
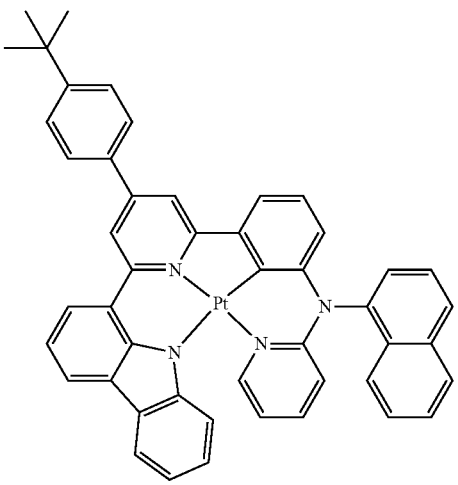
23
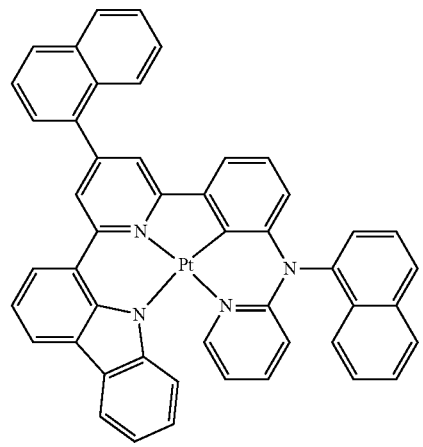
24
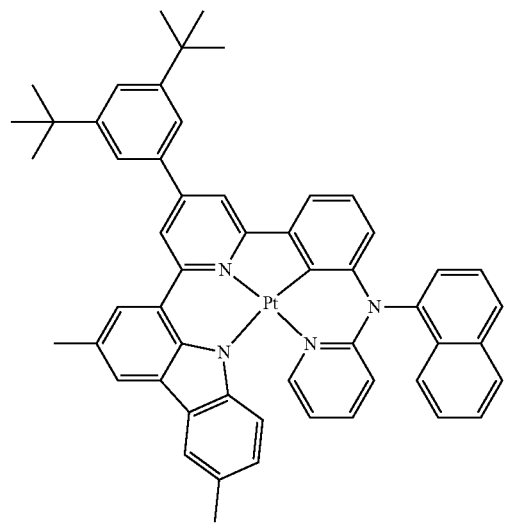
25

26
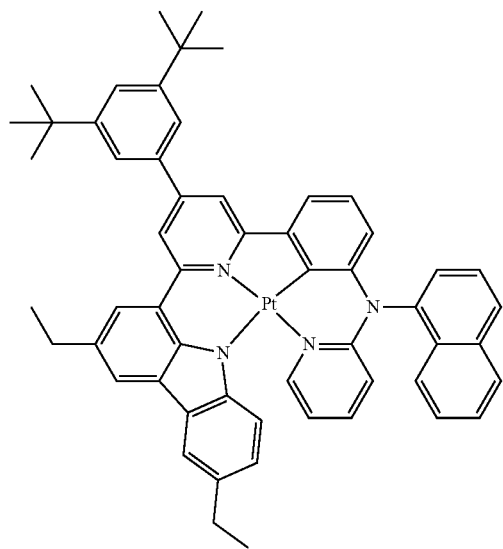
27
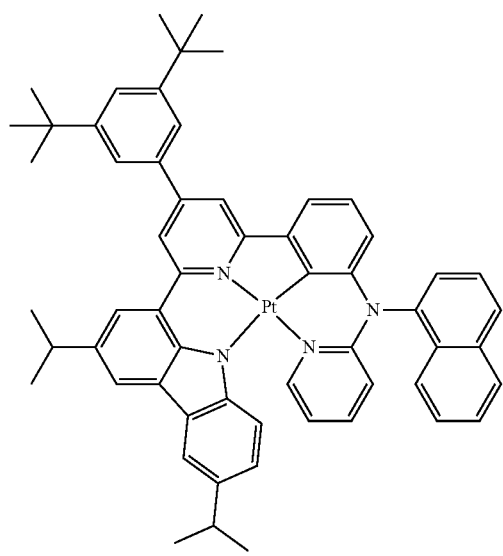
28
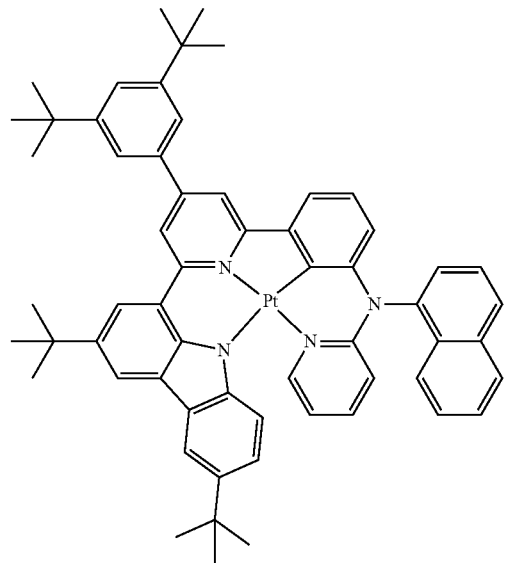
29
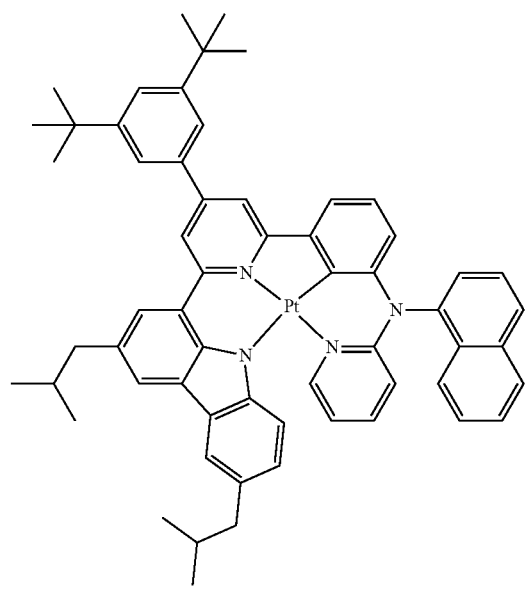

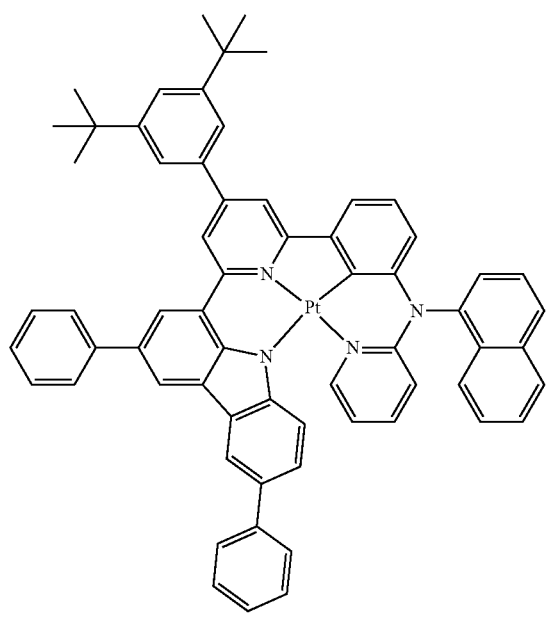
30
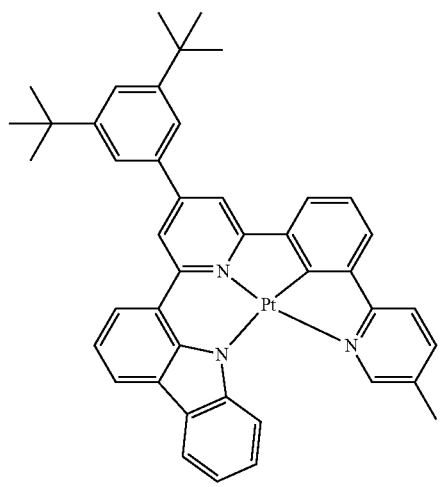
33
31
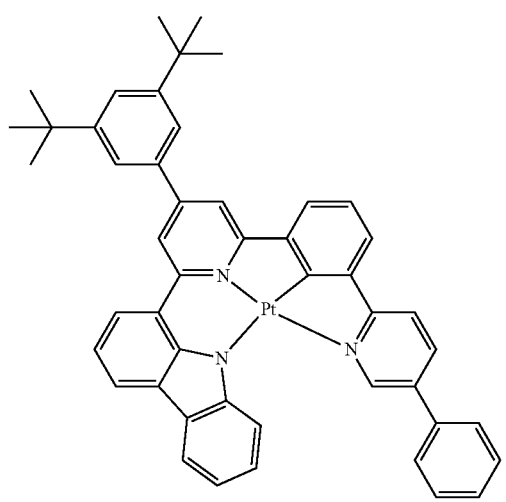
34
32
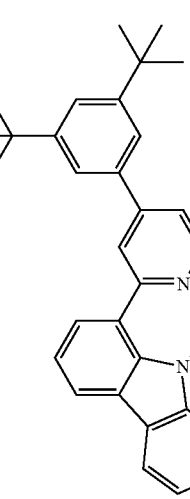
35

36
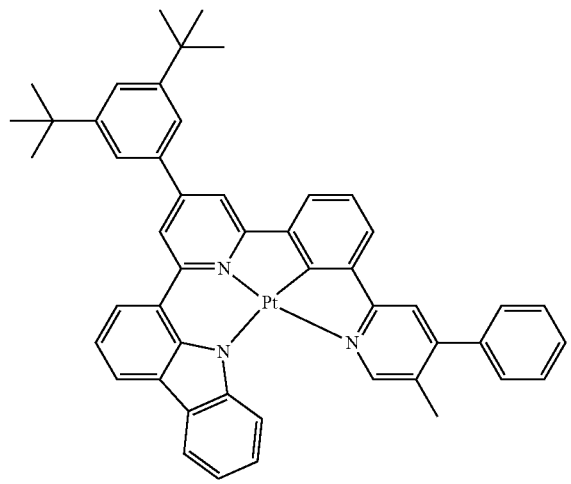
37
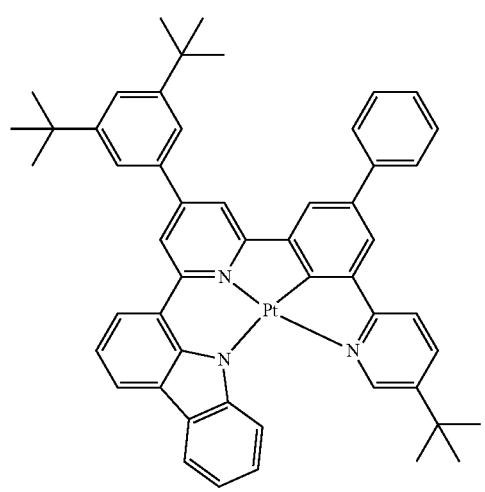
38
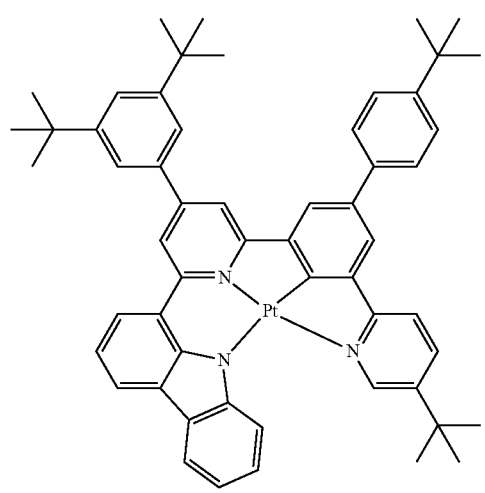
39
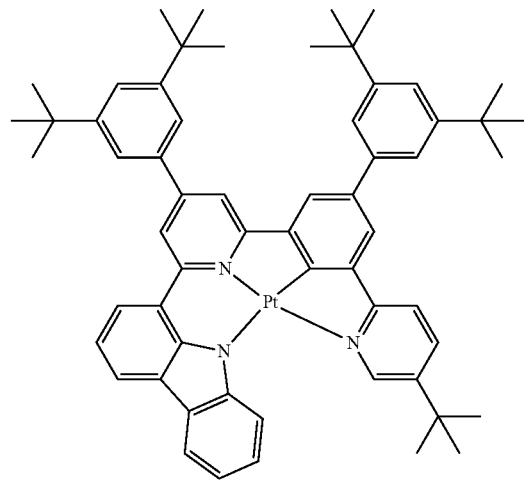
40
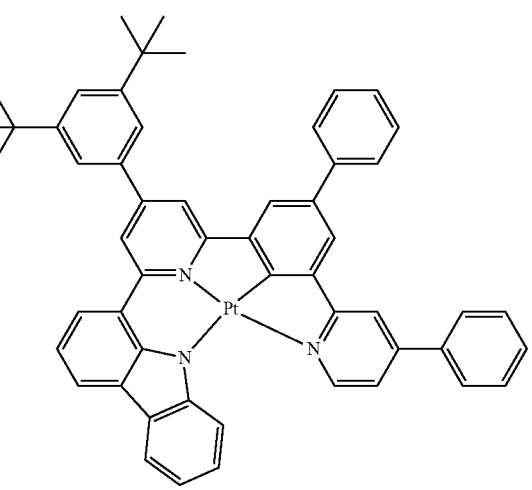
41
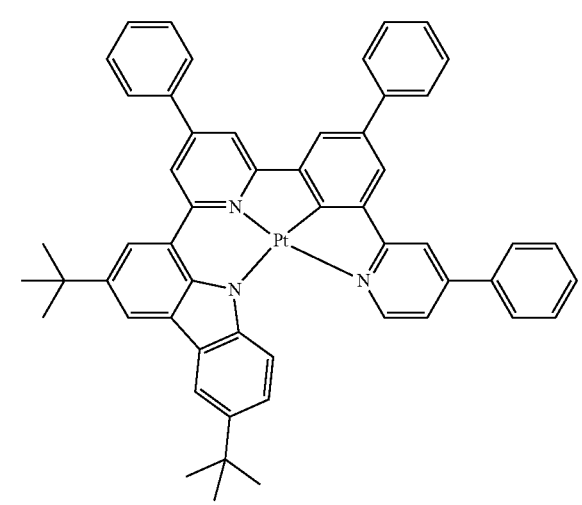

42
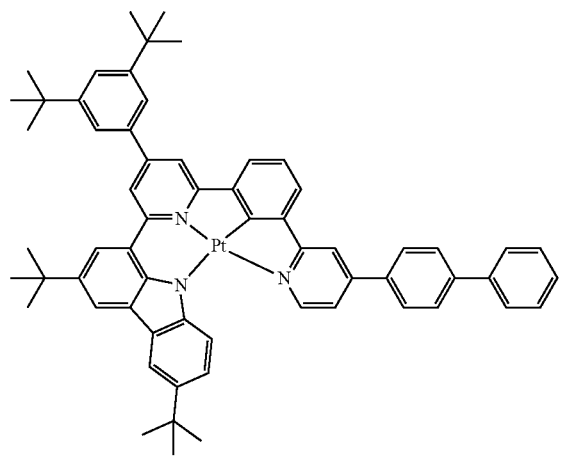
43
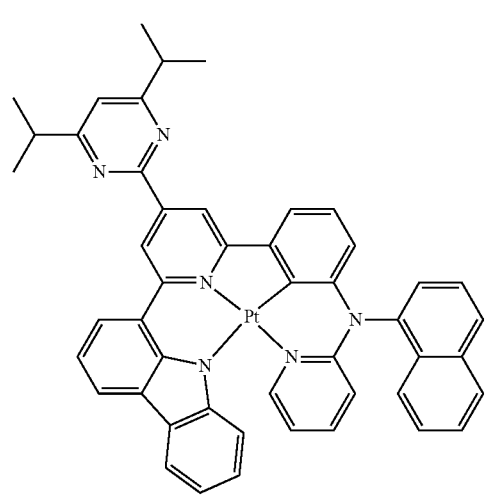
44
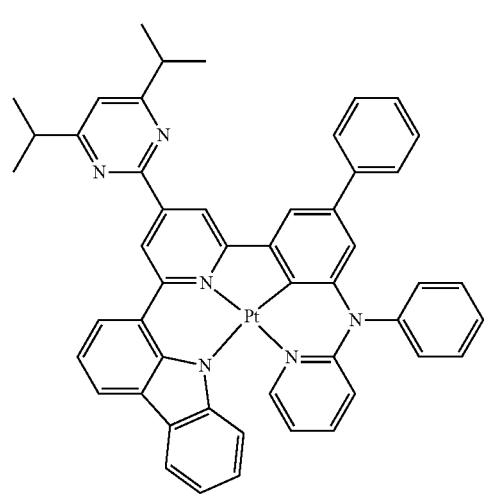
45
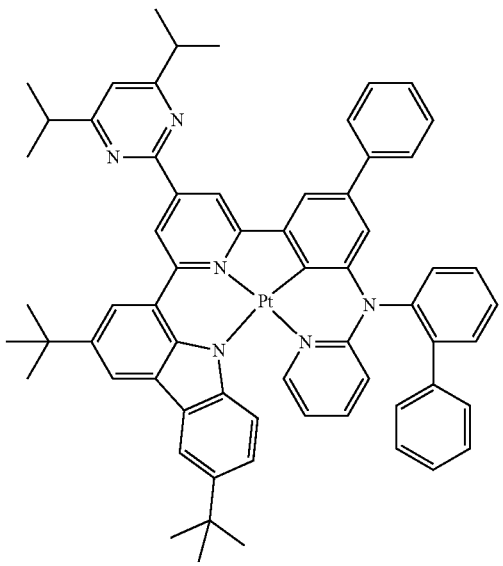
46
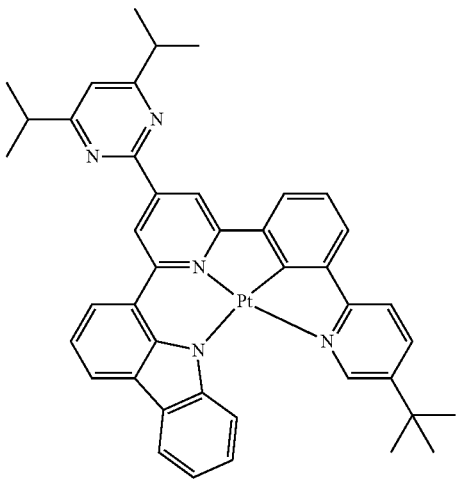
47
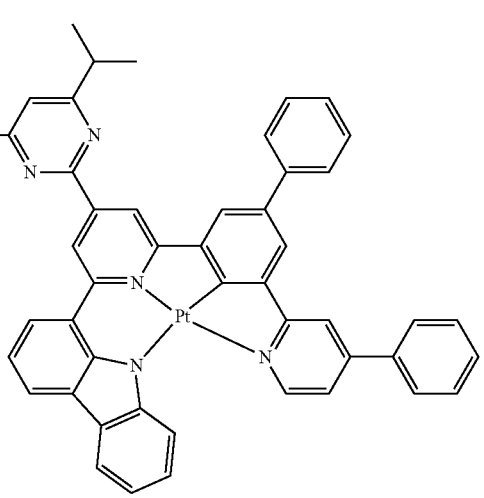

48
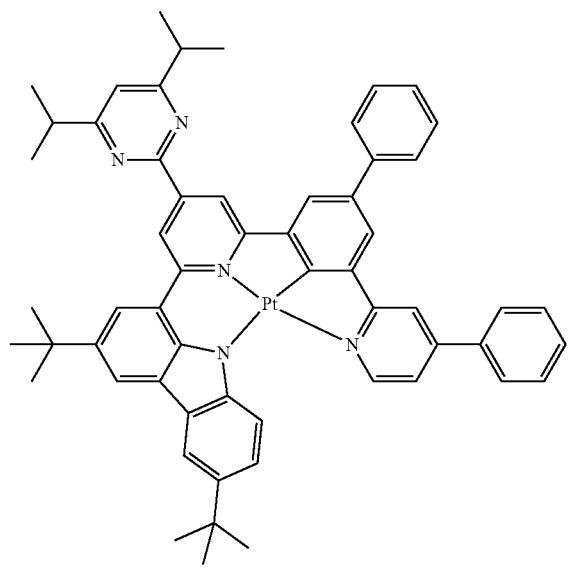
49
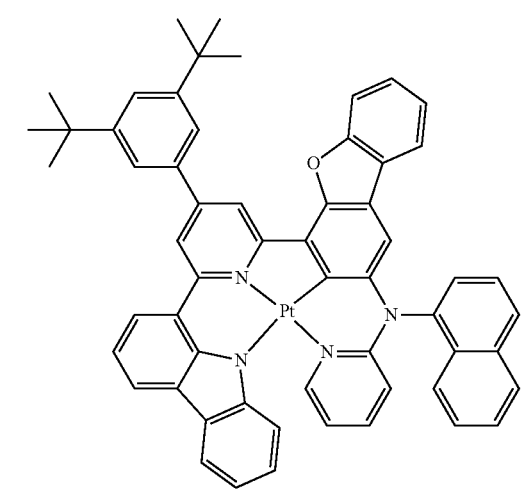
50
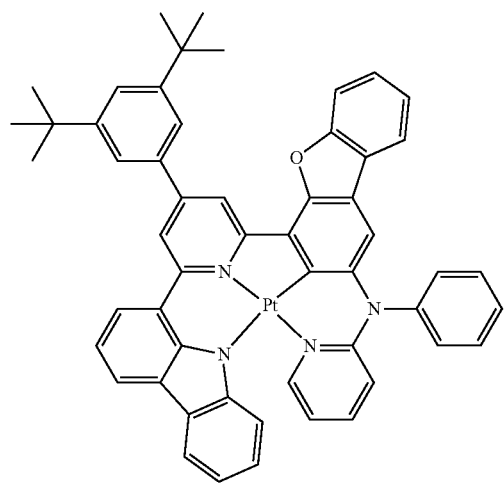
51
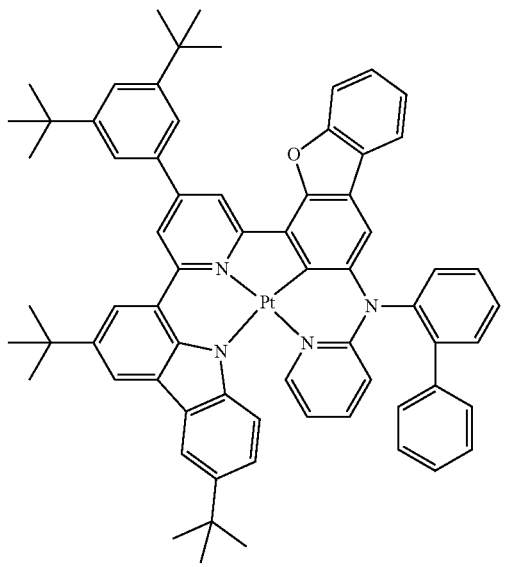
52
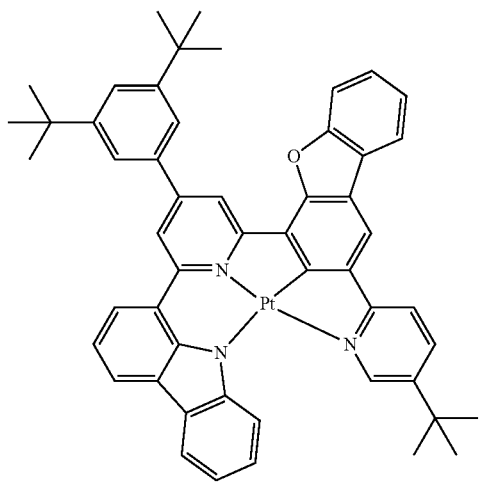
53
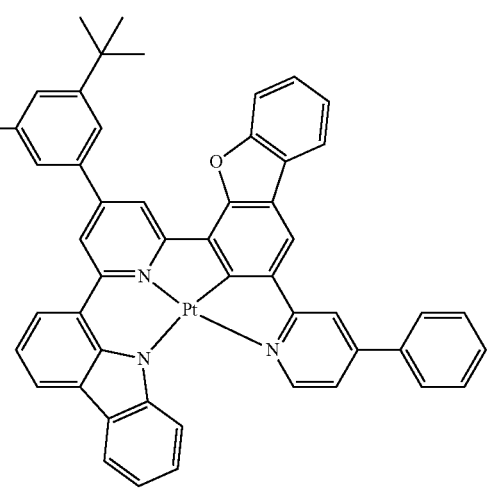

54
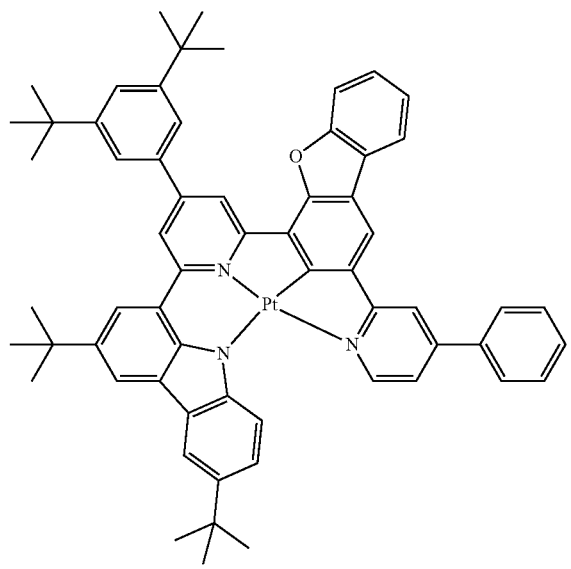
55
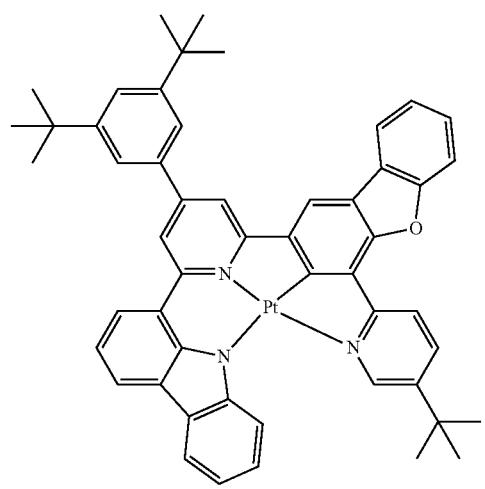
56
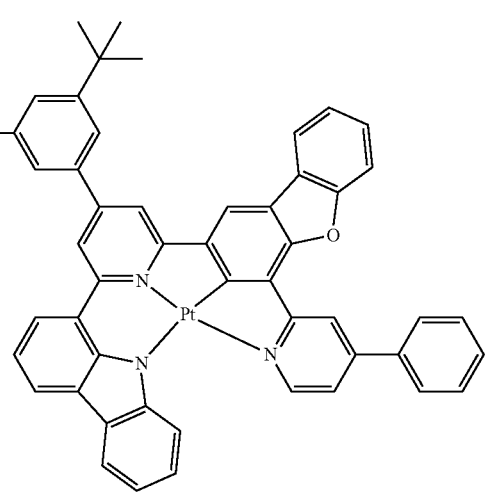
57
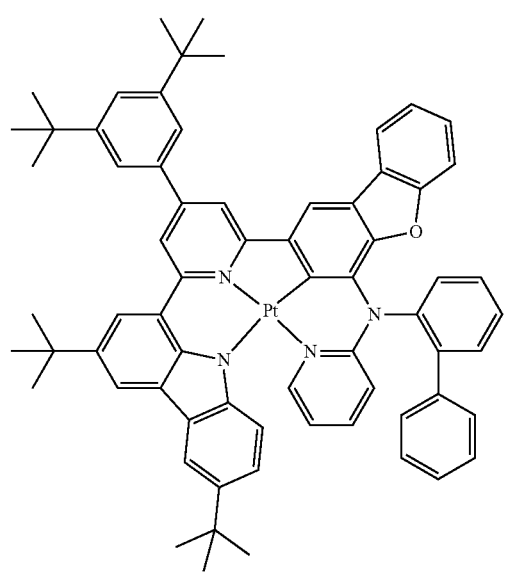
58
59

60
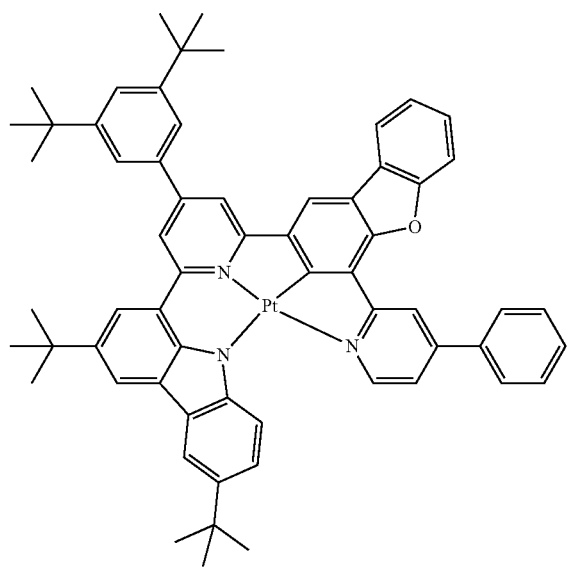
63
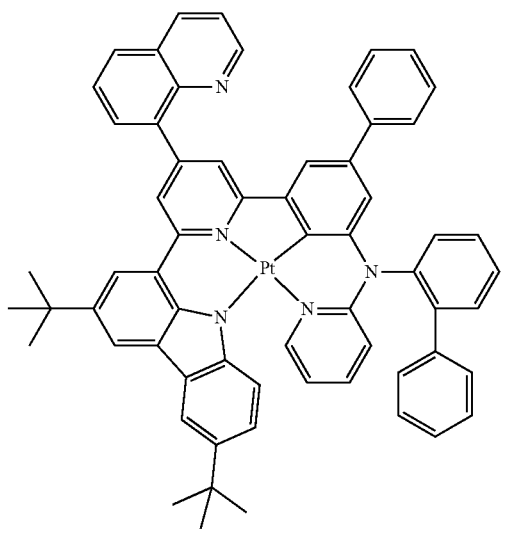
61
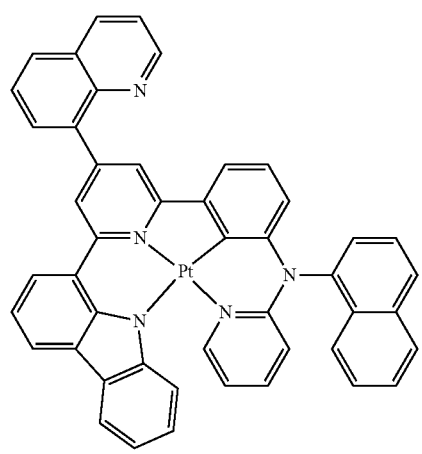
64
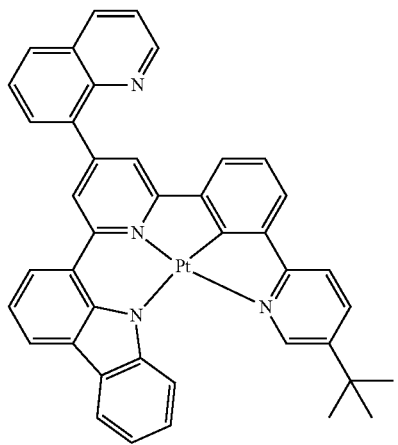
62
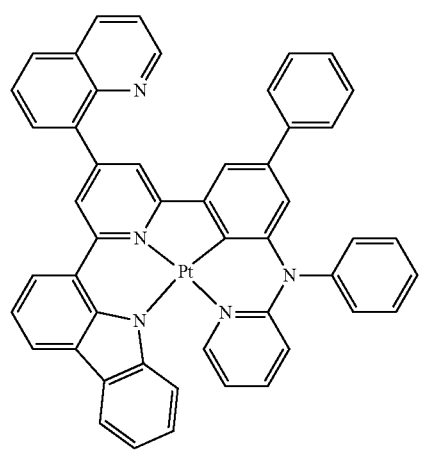
65
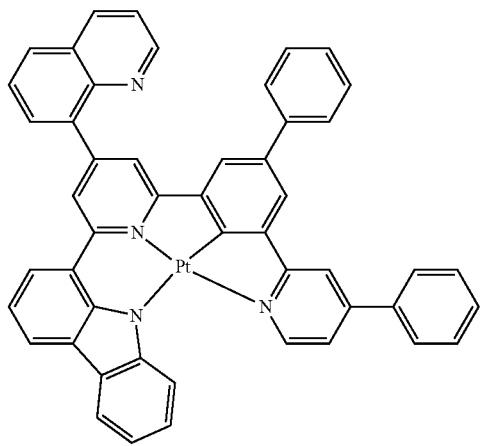

66
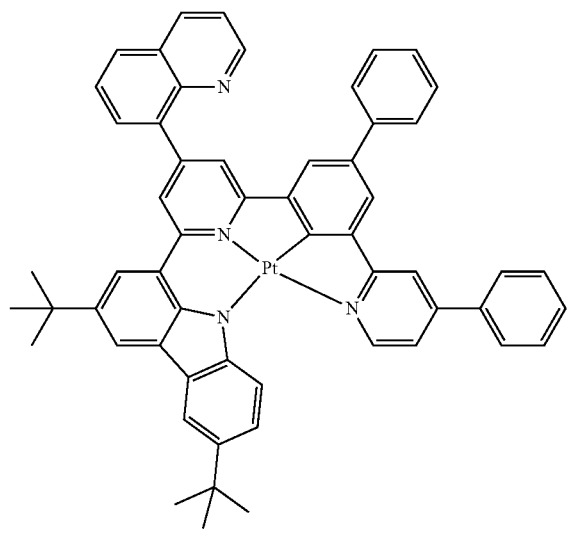
67
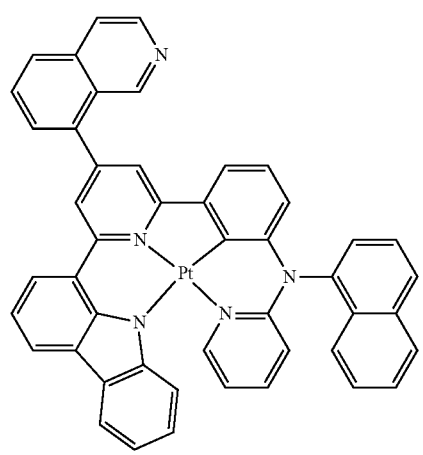
68
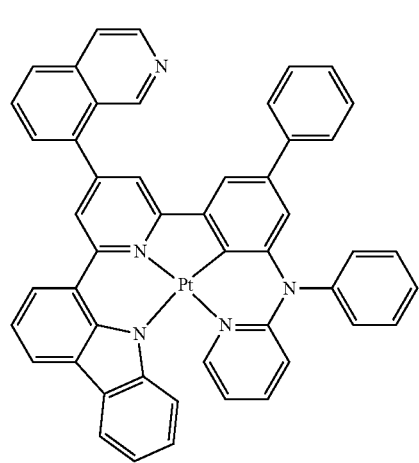
69
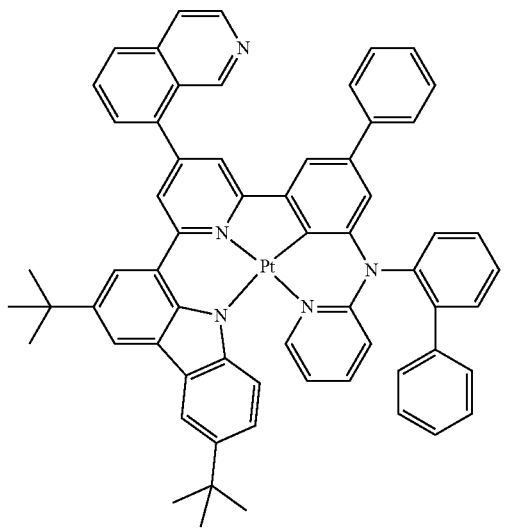
70
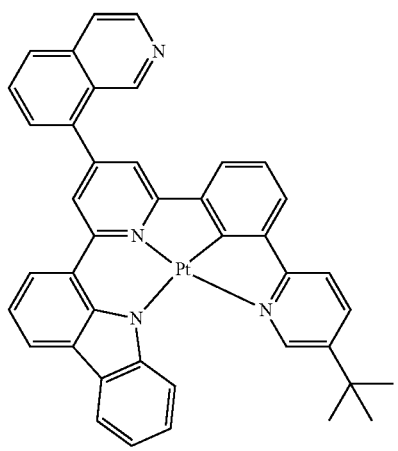
71
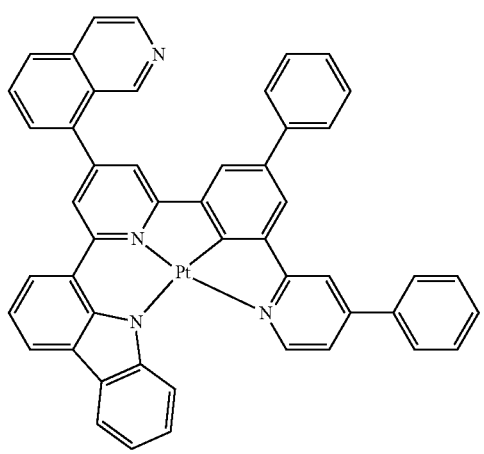

72
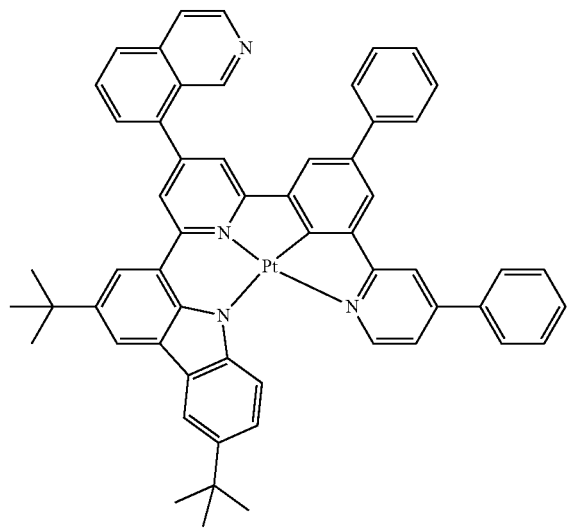
73
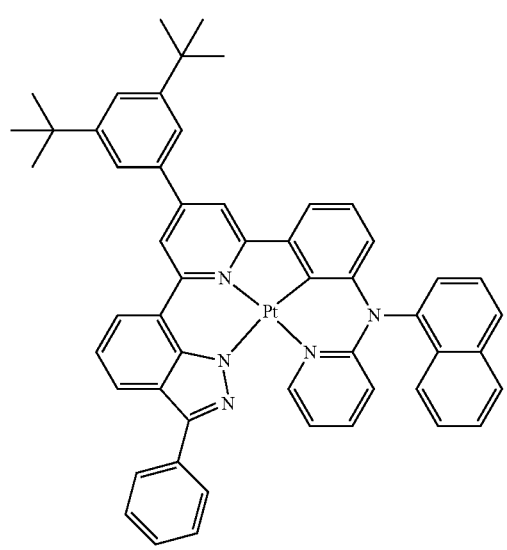
74
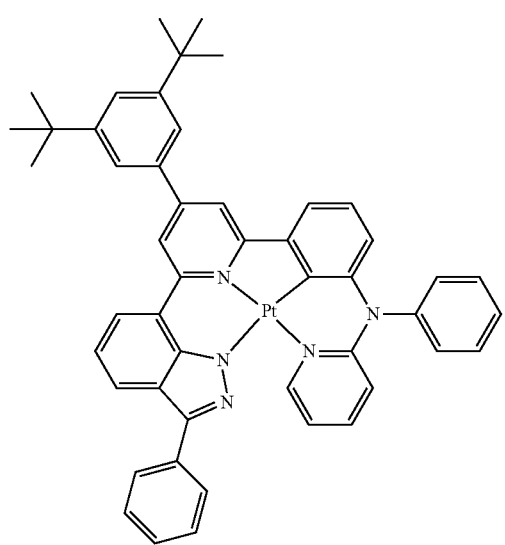
75
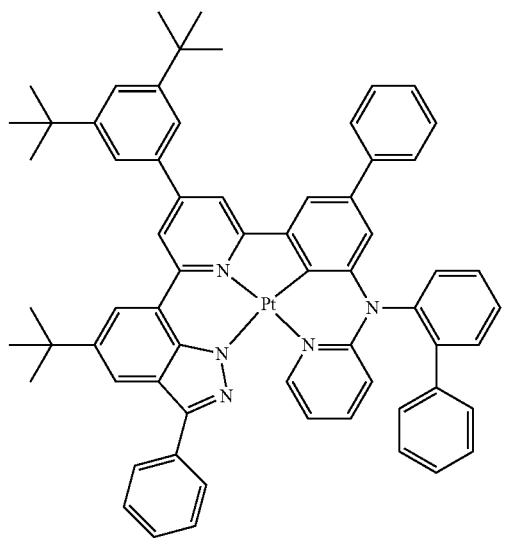
76
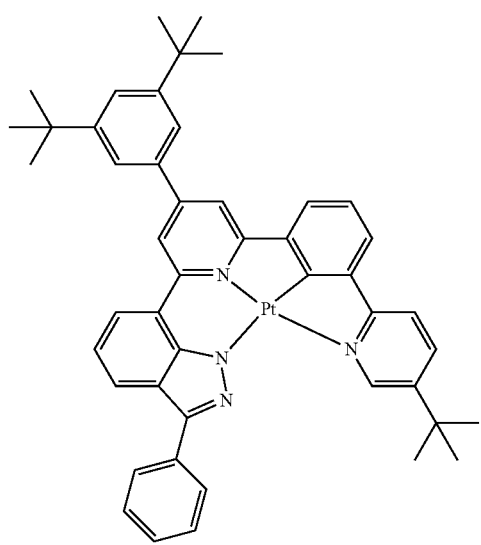
77
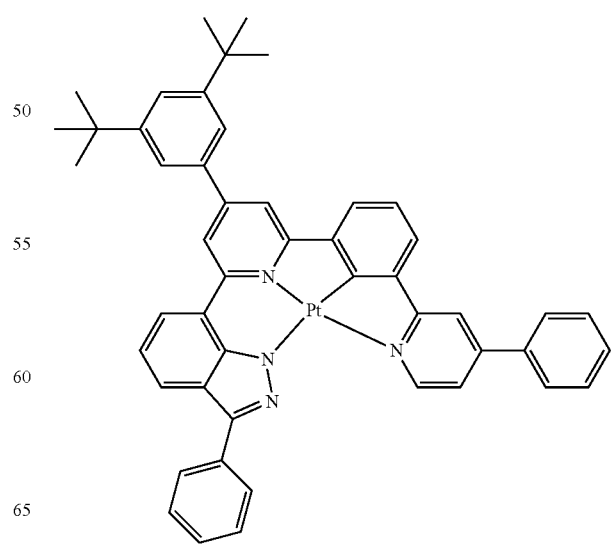

78
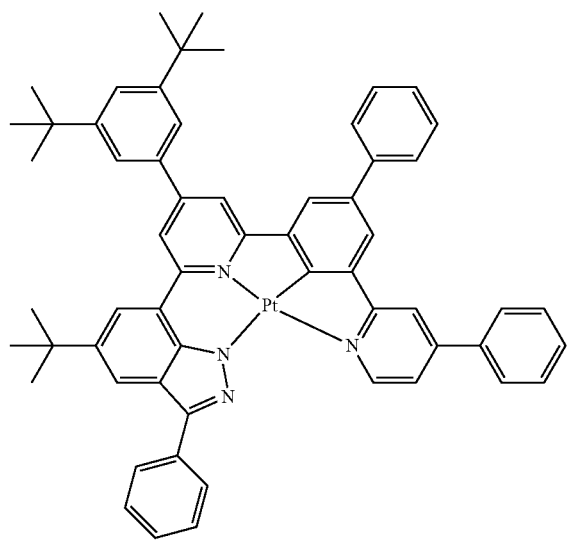
81
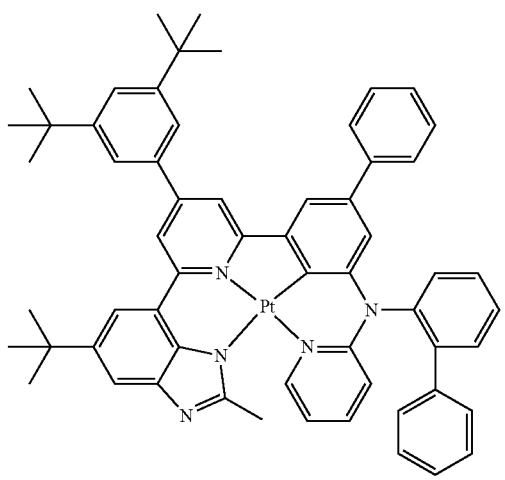
79
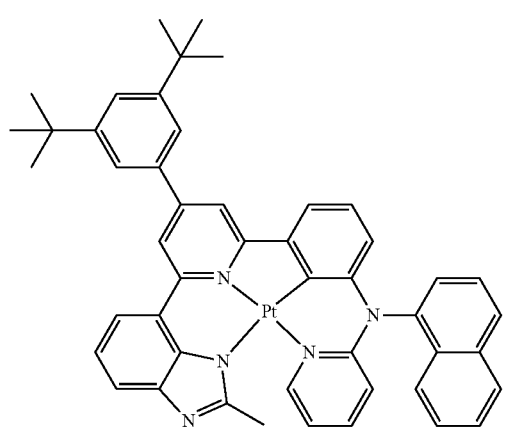
82
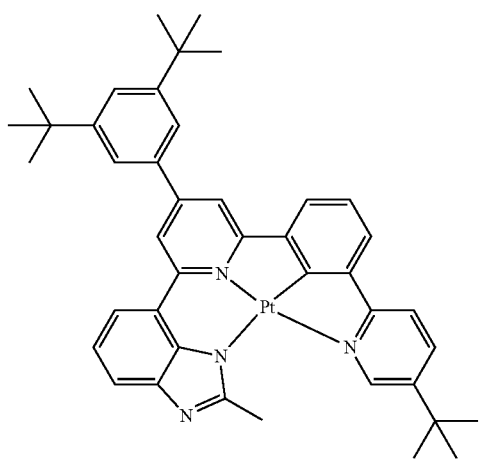
80
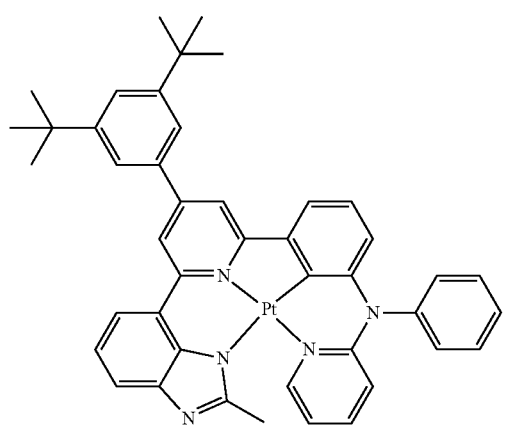
83
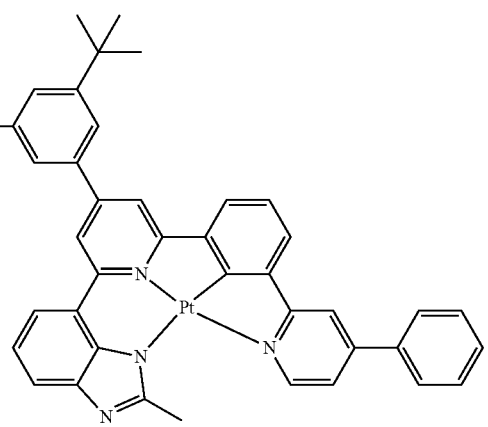

-continued
84
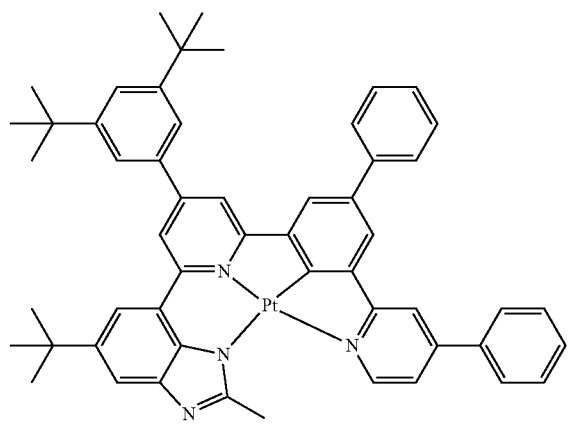
85
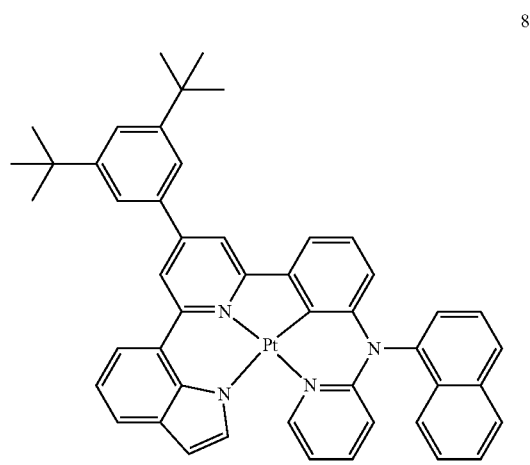
86
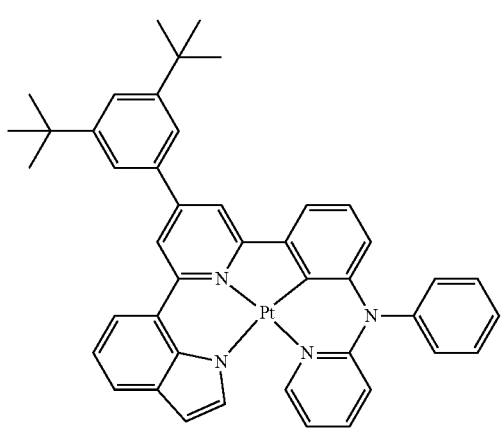
-continued
87
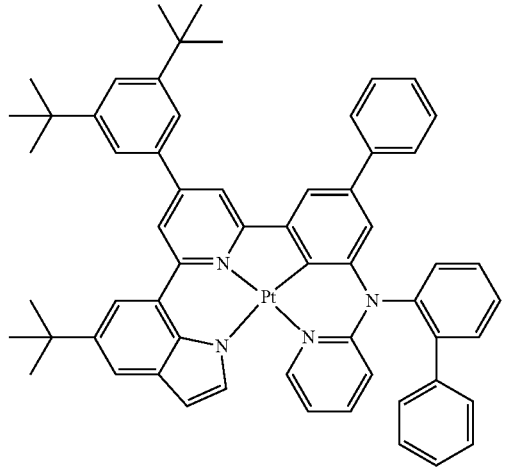
88
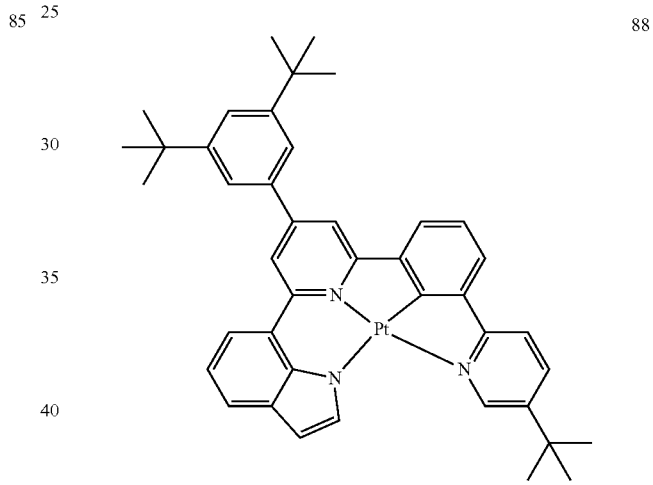
89
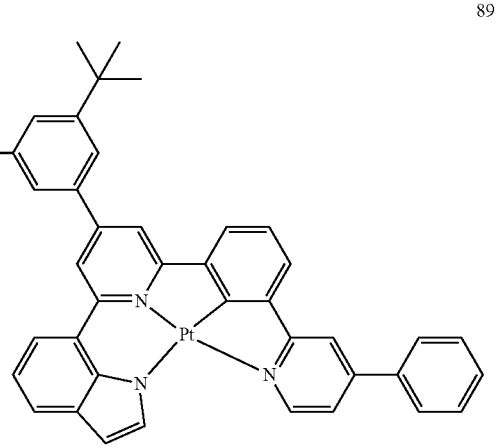

90
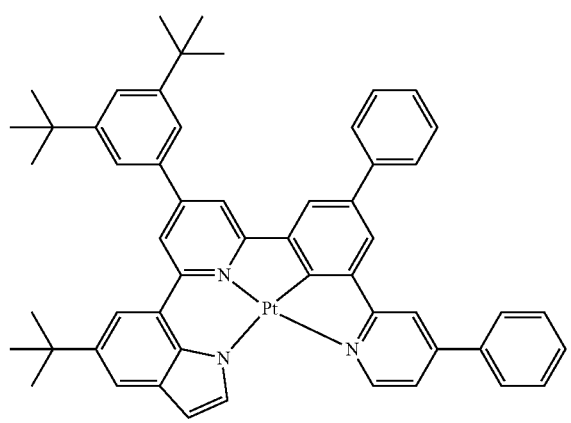
91
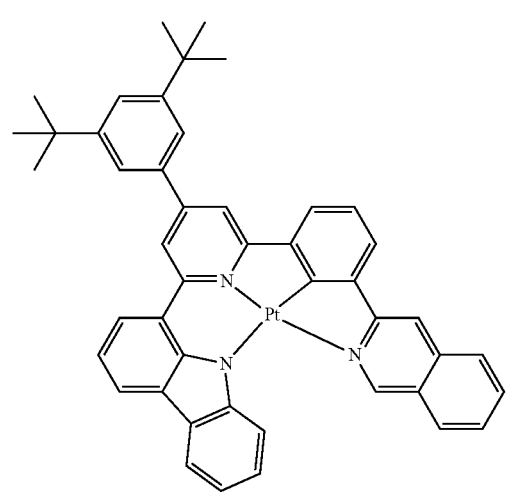
92
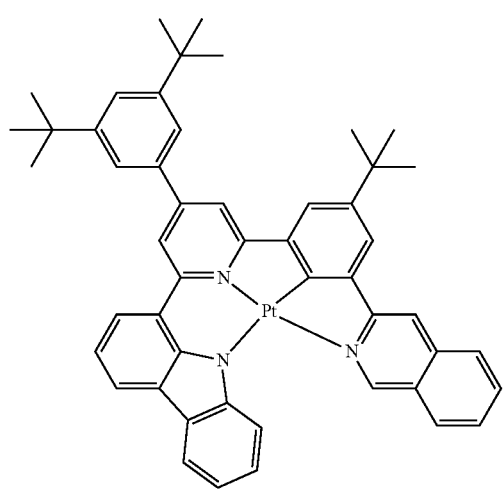
93
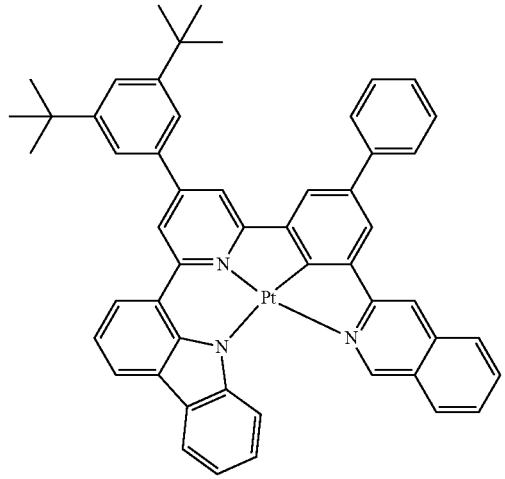
94
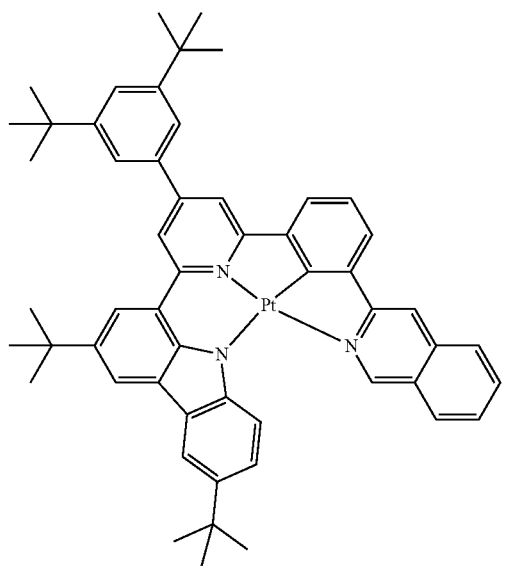
95
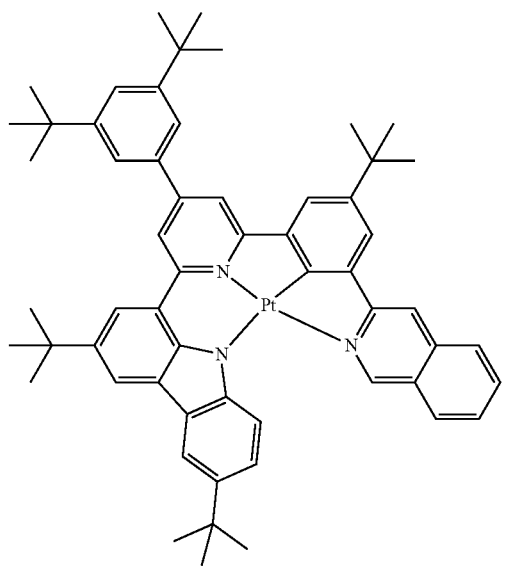

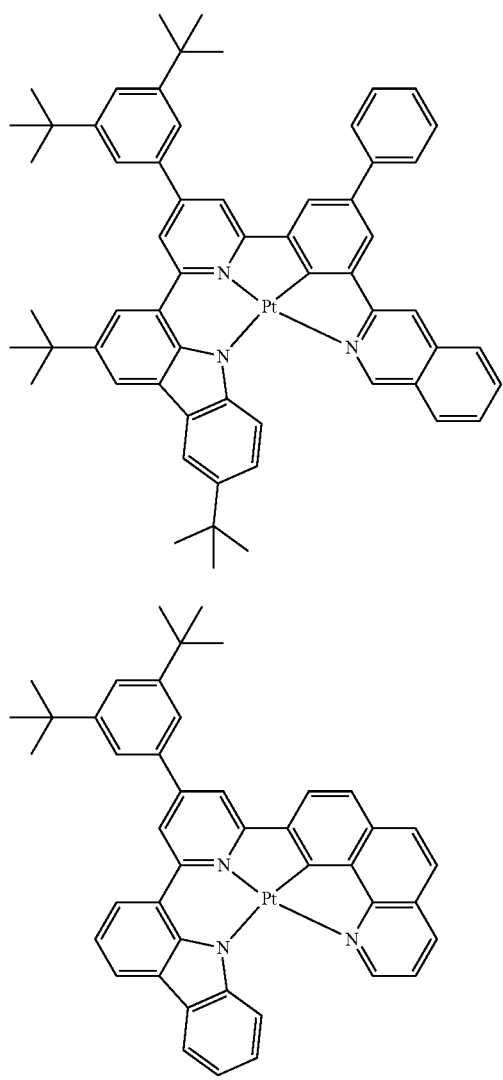
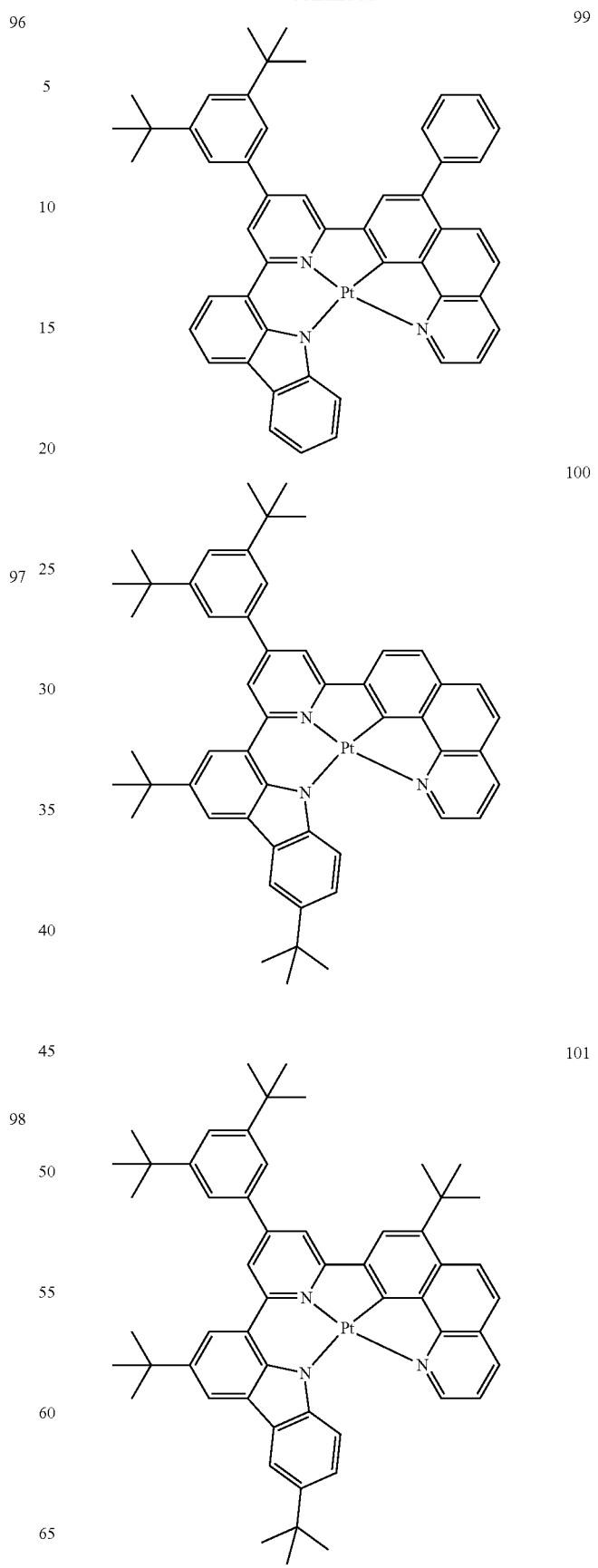

102
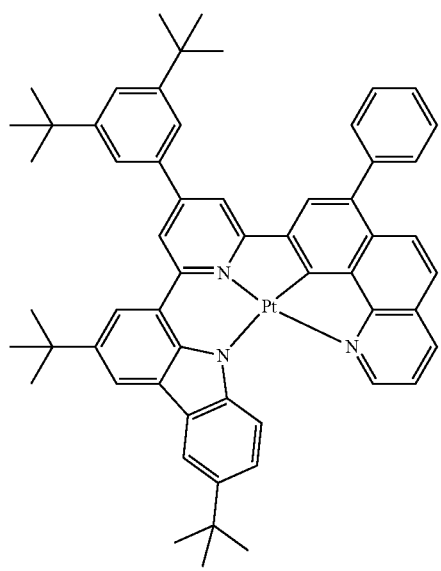
103
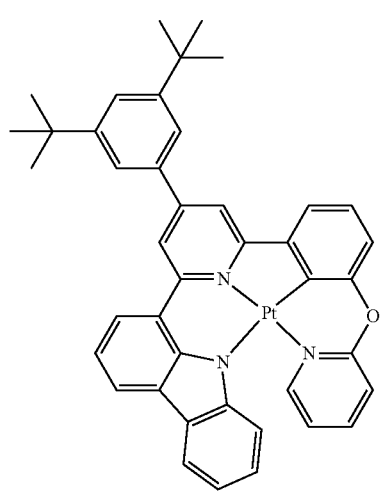
104
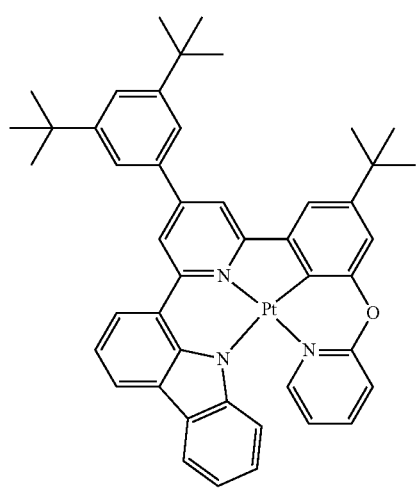
105
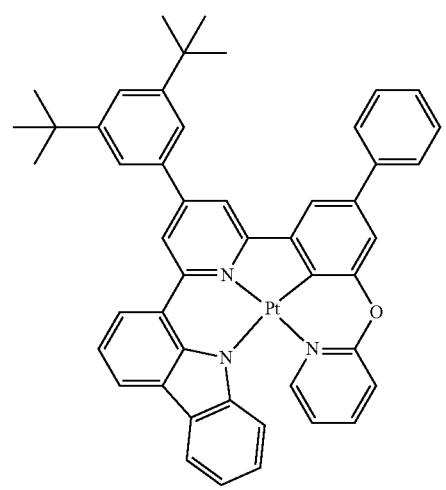
106
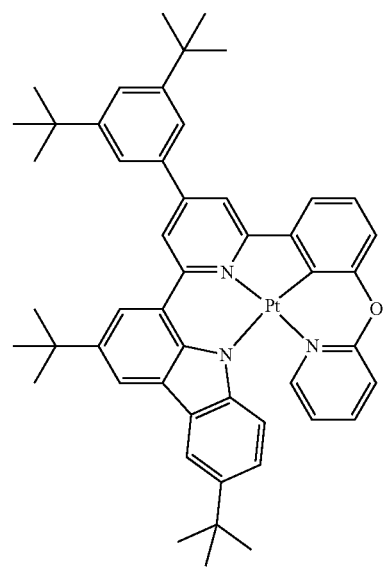
107
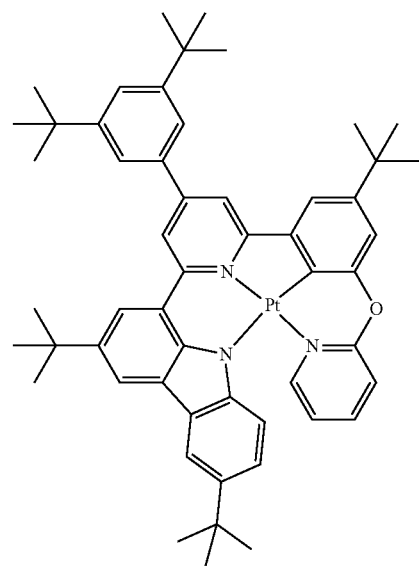

108
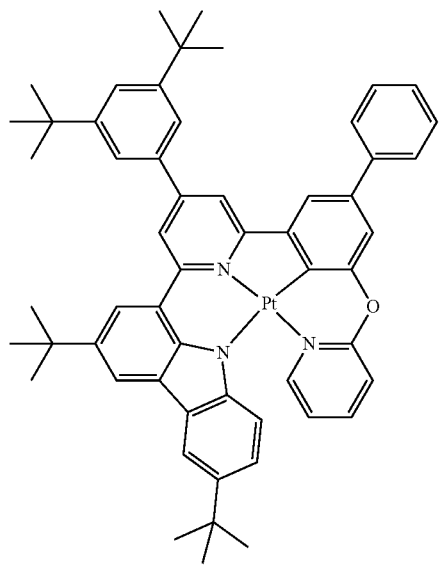
109
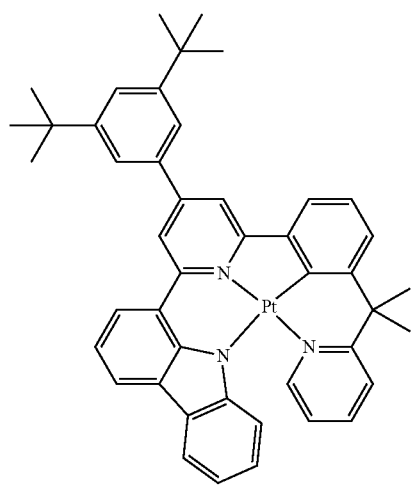
110
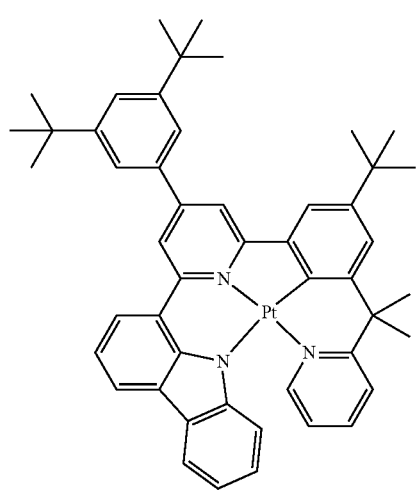
111
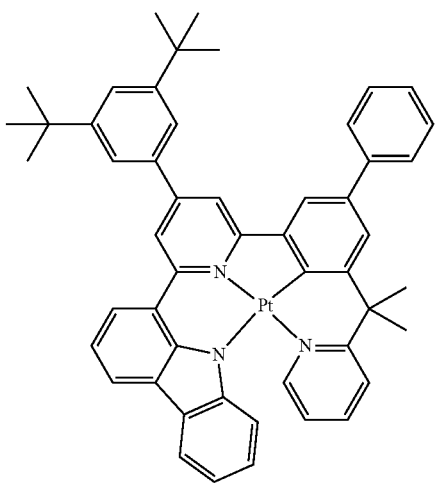
112
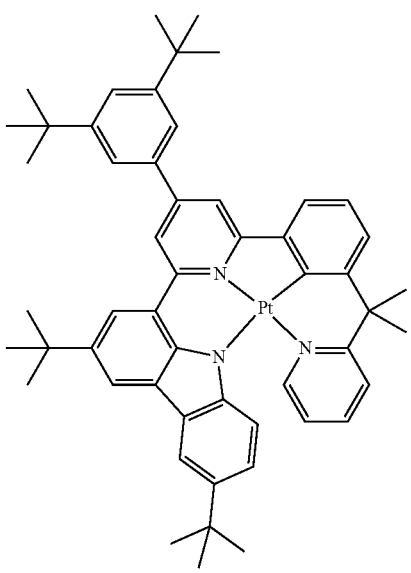
113
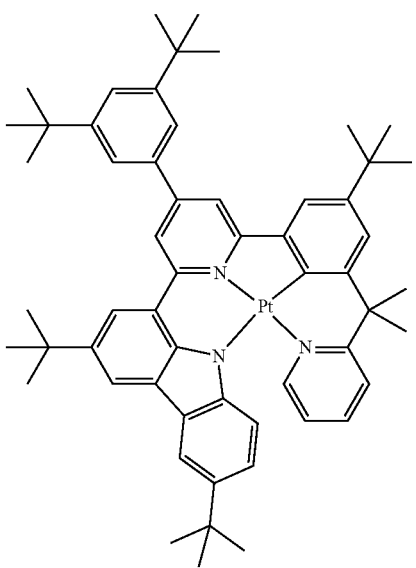

114
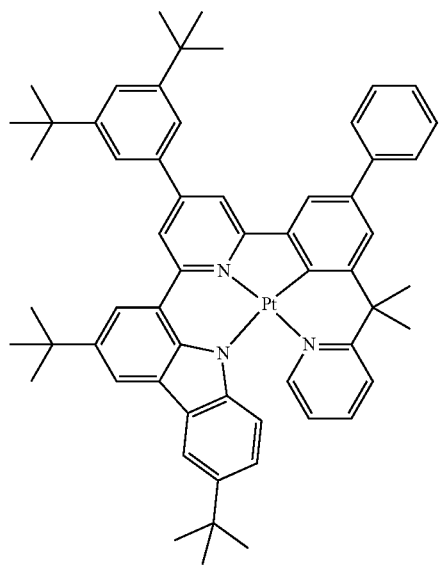
115
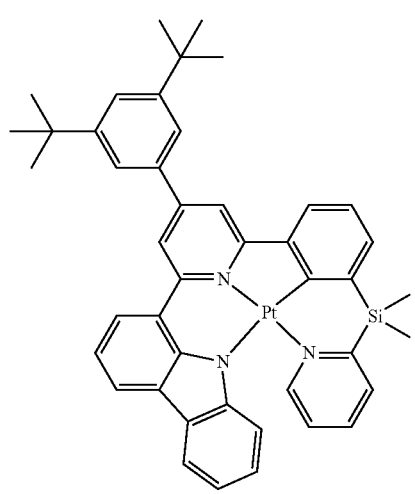
116
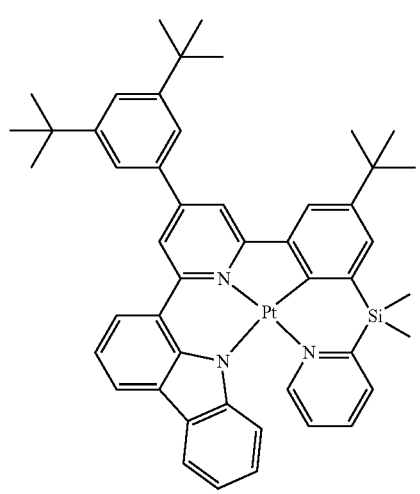
117
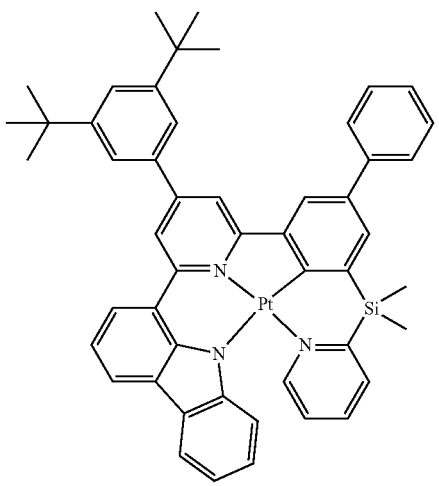
118
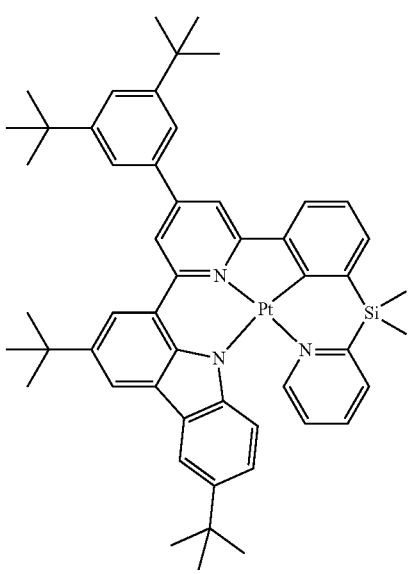
119
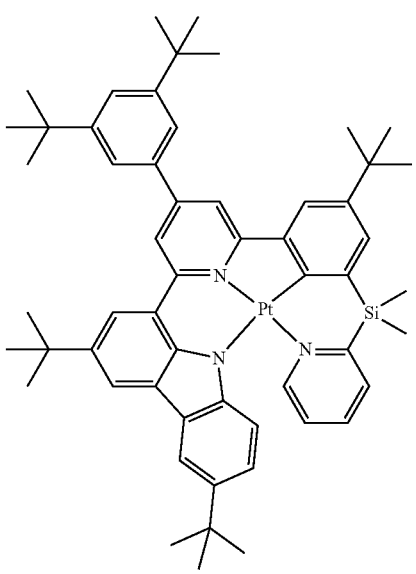

120 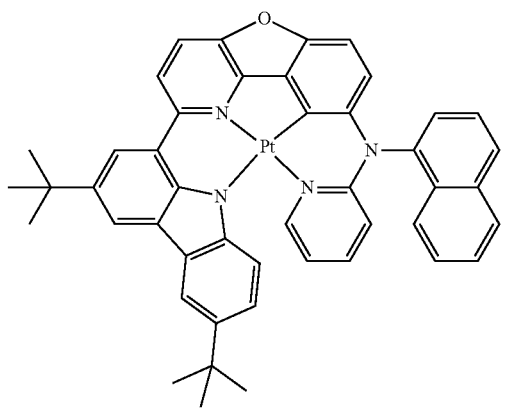
121 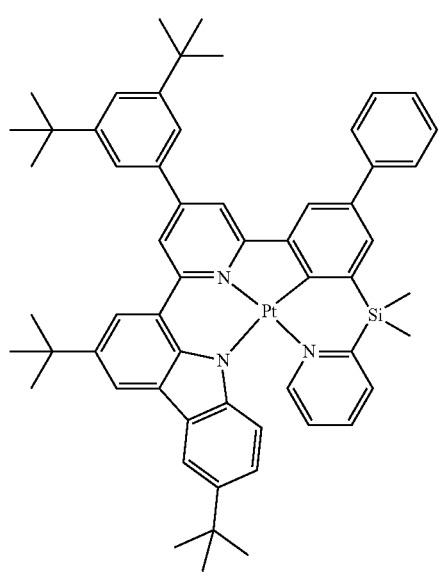
124 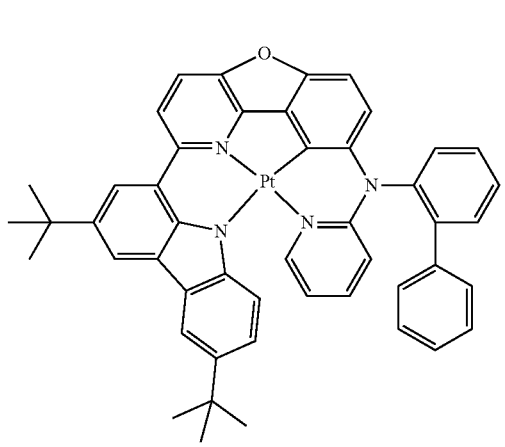
125
122 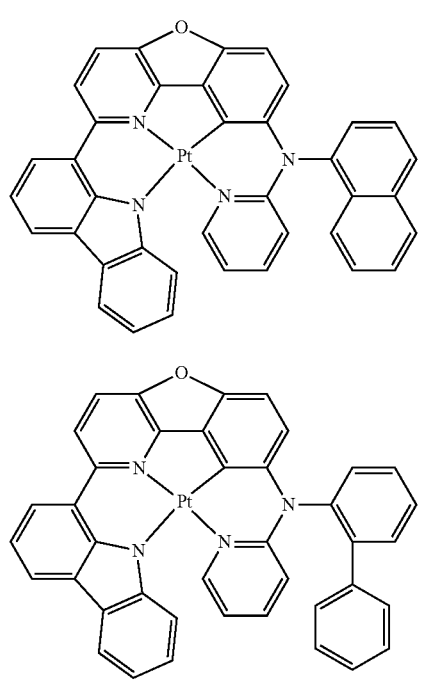
123
126 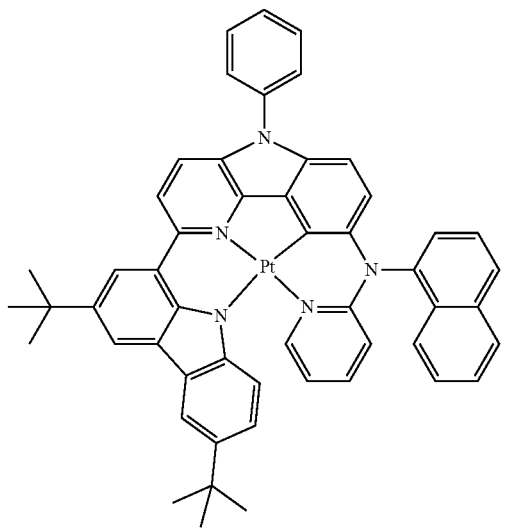

127

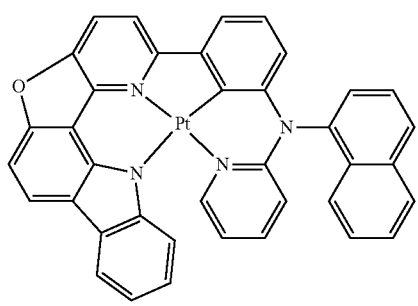

128

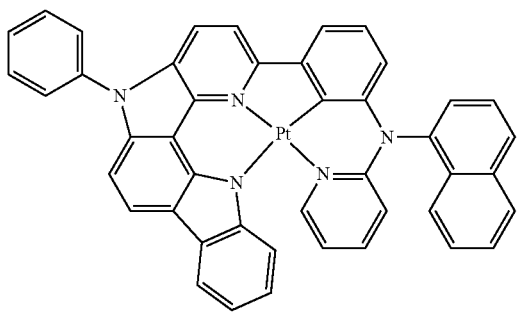

129

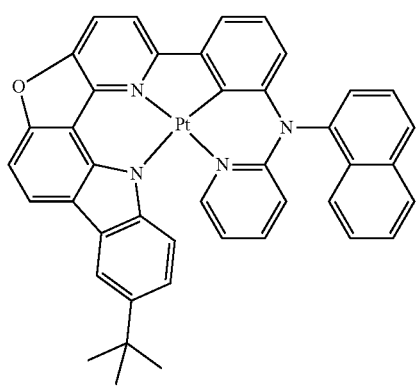

130

131

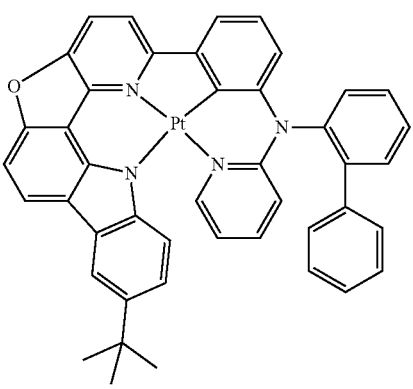

132

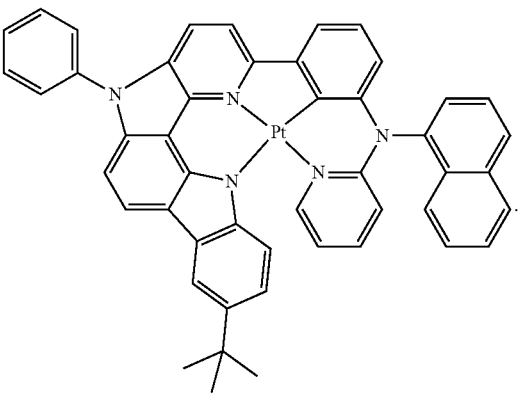

In Formula 1, $X_1$ may be N, a bond between $X_1$ and M may be a covalent bond, $X_2$ to $X_4$ may each independently be N or C, at least one of $X_2$ to $X_4$ may be C, one bond selected from a bond between $X_2$ and M, a bond between $X_3$ and M, and a bond between $X_4$ and M may be a covalent bond, and the remaining two bonds may each be a coordinate bond. That is, the organometallic compound essentially includes a covalent bond between one N and M and a covalent bond between one C and M in the molecular structure (see Formula 1-1'). Since the covalent bond between N and M increases a spin density of the metal M, a maximum emission wavelength of the organometallic compound represented by Formula 1 may be easily controlled, and an organic light-emitting device including the organometallic compound may have excellent efficiency.

Also, Formula 1 essentially includes a 5-membered ring represented by $CY_5$, and a cyclometallated ring formed by $CY_5$, $CY_1$, $CY_2$, and M in Formula 1 is a 6-membered ring, a 7-membered ring, or an 8-membered ring (see Formula 1-1'). Accordingly, since charge mobility of the organometallic compound including a ligand represented by Formula 1-1' is improved and an energy level control is facilitated, an organic light-emitting device including the organometallic compound may have improved efficiency and roll-off.

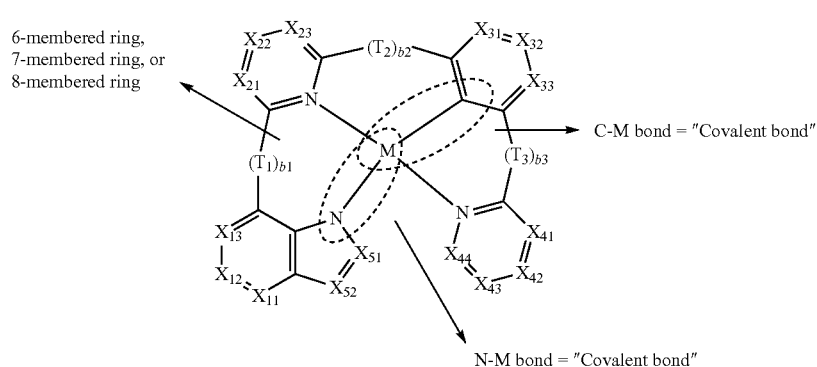

Formula 1-1'

For example, a highest occupied molecular orbital (HOMO) energy level, a lowest unoccupied molecular orbital (LUMO) energy level, a singlet ($S_1$) energy level, and a triplet ($T_1$) energy level of Compounds 1, 32, 43, 49, 55, 61, A, and B were evaluated by a density functional theory (DFT) method of a Gaussian program (the structure was optimized at B3LYP, 6-31G(d,p) level). Results thereof are shown in Table 1.

TABLE 1

| Compound No. | HOMO (eV) | LUMO (eV) | $S_1$ energy level (eV) | $T_1$ energy level (eV) |
| --- | --- | --- | --- | --- |
| 1 | −4.406 | −1.610 | 2.270 | 2.025 |
| 32 | −4.535 | −1.733 | 2.323 | 2.029 |
| 43 | −4.355 | −1.871 | 2.011 | 1.769 |
| 49 | −4.440 | −1.680 | 2.248 | 2.001 |
| 55 | −4.414 | −1.735 | 2.157 | 1.954 |
| 61 | −4.350 | −1.863 | 2.075 | 1.901 |
| A | −5.850 | −4.548 | 1.302 | −0.208 |
| B | −4.418 | −1.584 | 2.230 | 1.971 |

TABLE 1-continued

| Compound No. | HOMO (eV) | LUMO (eV) | $S_1$ energy level (eV) | $T_1$ energy level (eV) |
| --- | --- | --- | --- | --- |

32

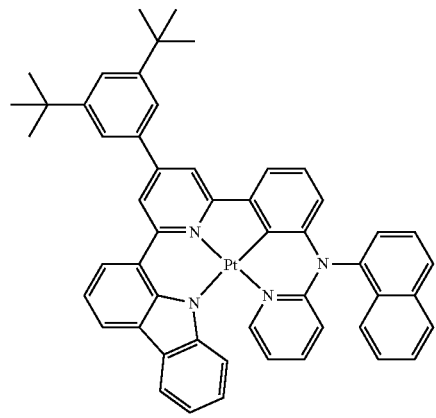

1

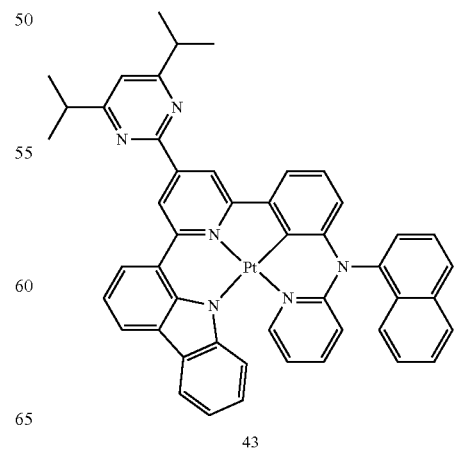

43

TABLE 1-continued

| Compound No. | HOMO (eV) | LUMO (eV) | $S_1$ energy level (eV) | $T_1$ energy level (eV) |
|---|---|---|---|---|

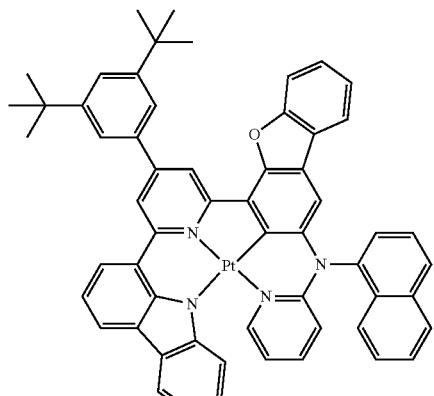

49

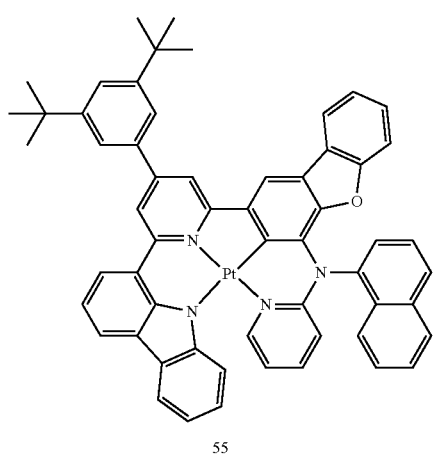

55

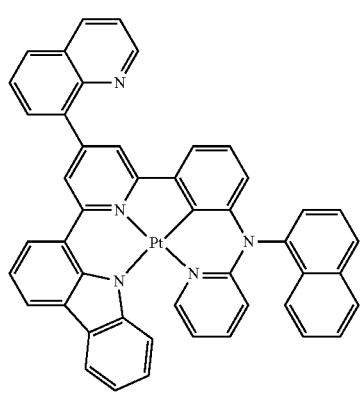

61

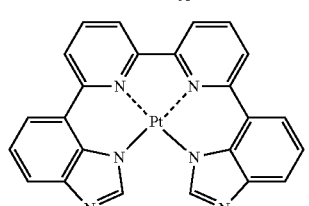

Compound A

TABLE 1-continued

| Compound No. | HOMO (eV) | LUMO (eV) | $S_1$ energy level (eV) | $T_1$ energy level (eV) |
|---|---|---|---|---|

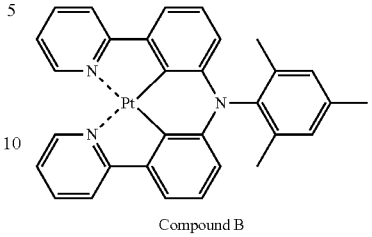

Compound B

From Table 1, it is confirmed that the organometallic compound represented by Formula 1 has electric characteristics suitable for use in an electric device, for example, for use as a dopant for an organic light-emitting device.

Synthesis methods of the organometallic compound represented by Formula 1 may be understood by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;
a second electrode; and
an organic layer disposed between the first electrode and the second electrode,
wherein the organic layer includes an emission layer and at least one of the organometallic compounds represented by Formula 1.

Due to the inclusion of the organic layer including the organometallic compound represented by Formula 1, the organic light-emitting device may have low driving voltage, high efficiency, high power, high quantum efficiency, a long lifespan, a low roll-off ratio, and excellent color purity.

The organometallic compound represented by Formula 1 may be used between a pair of an organic light-emitting device. For example, the organometallic compound represented by Formula 1 may be included in the emission layer. In this regard, the organometallic compound may act as a dopant, and the emission layer may further include a host (that is, an amount of the organometallic compound represented by Formula 1 is smaller than an amount of the host).

The expression "(an organic layer) includes at least one of organometallic compounds" as used herein may include an embodiment in which "(an organic layer) includes identical organometallic compounds represented by Formula 1" and an embodiment in which "(an organic layer) includes two or more different organometallic compounds represented by Formula 1."

For example, the organic layer may include, as the organometallic compound, only Compound 1. In this embodiment, Compound 1 may be included in an emission layer of the organic light-emitting device. In one or more embodiments, the organic layer may include, as the organometallic compound, Compound 1 and Compound 2. In this embodiment, Compound 1 and Compound 2 may be included in an identical layer (for example, Compound 1 and Compound 2 may both be included in an emission layer).

The first electrode may be an anode, which is a hole injection electrode, and the second electrode may be a cathode, which is an electron injection electrode; or the first electrode may be a cathode, which is an electron injection electrode, and the second electrode may be an anode, which is a hole injection electrode.

In one or more embodiments, in the organic light-emitting device, the first electrode is an anode; the second electrode is a cathode; the organic layer further includes a hole transport region disposed between the first electrode and the emission layer and an electron transport region disposed between the emission layer and the second electrode; the hole transport region includes a hole injection layer, a hole transport layer, an electron blocking layer, or any combination thereof; and the electron transport region includes a hole blocking layer, an electron transport layer, an electron injection layer, or any combination thereof.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include a hole injection layer, a hole transport layer, an electron blocking layer, a buffer layer, or any combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary depending on a material that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), polyaniline/poly(4-styrene sulfonate) (PANI/PSS), a compound represented by Formula 201 below, and a compound represented by Formula 202 below:

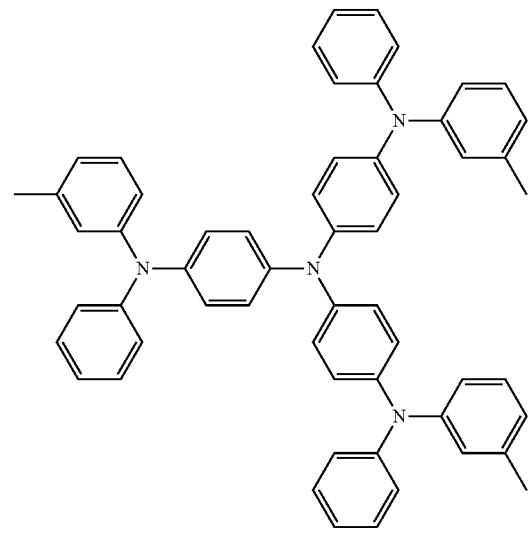

m-MTDATA

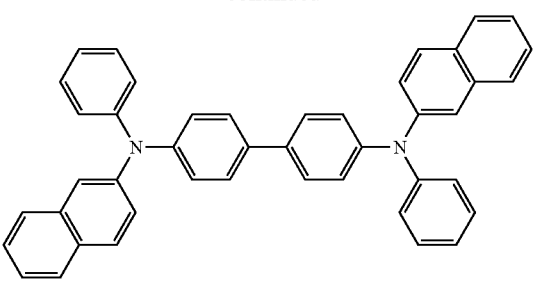
β-NPB
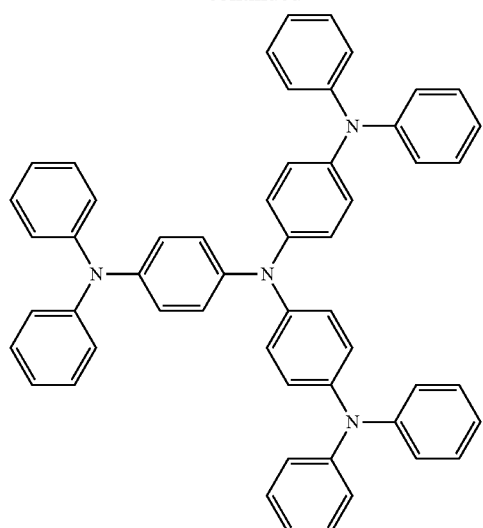
TDATA
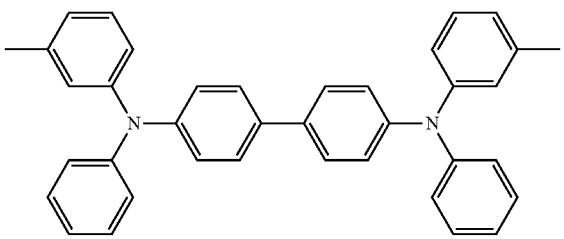
TPD
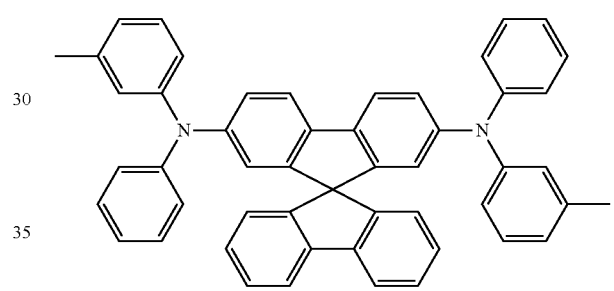
Spiro-TPD
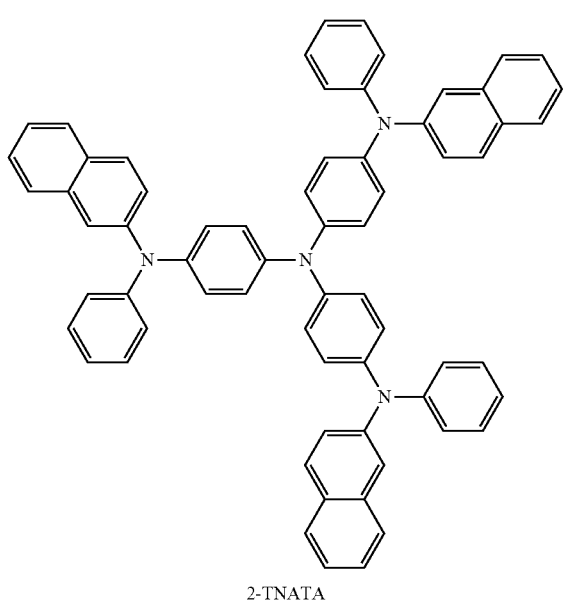
2-TNATA
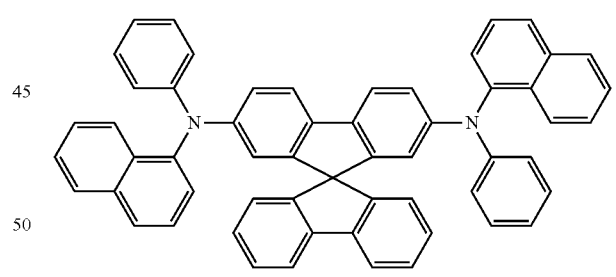
Spiro-NPB
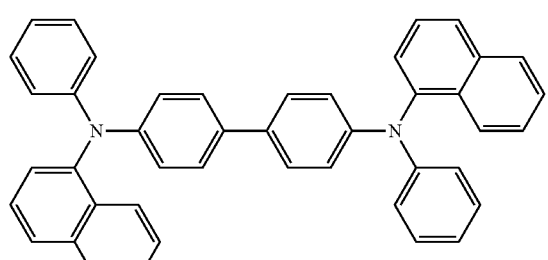
NPB
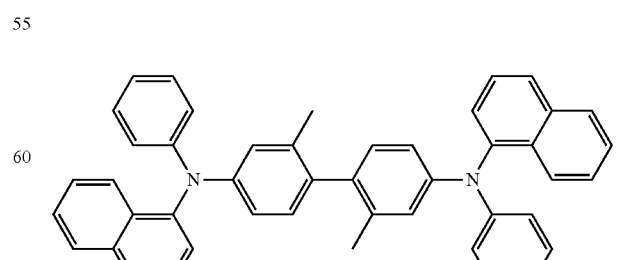
methylated NPB -continued

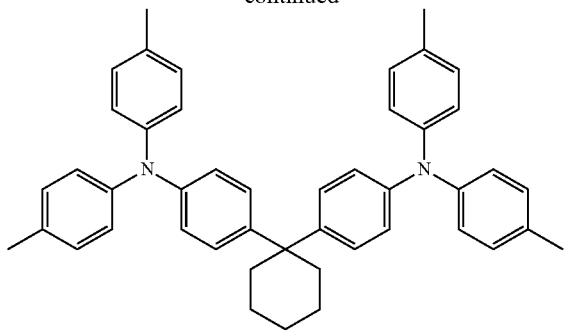
TAPC

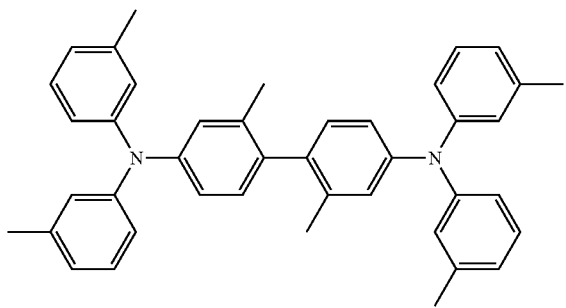
HMTPD

Formula 201

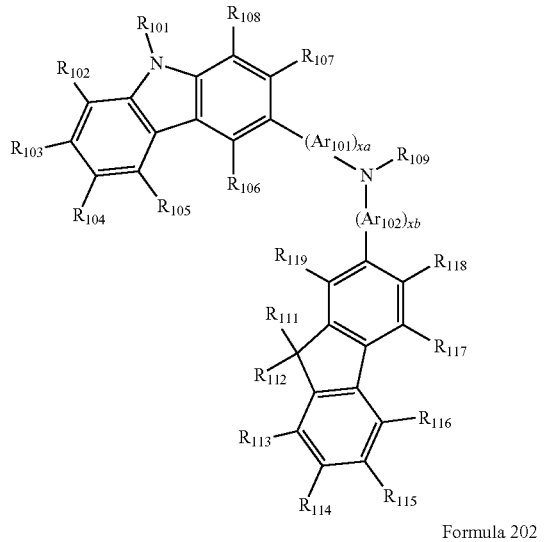

Formula 202

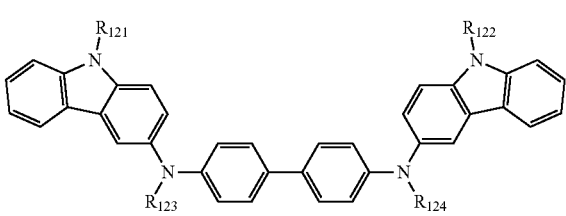

$Ar_{101}$ to $Ar_{102}$ in Formula 201 may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

xa and xb in Formula 201 may each independently be an integer from 0 to 5, or 0, 1, or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, or the like), and a $C_1$-$C_{10}$ alkoxy group (for example, a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one selected from;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

$R_{109}$ in Formula 201 may be selected from:

a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In one or more embodiments, the compound represented by Formula 201 may be represented by Formula 201A, but embodiments of the present disclosure are not limited thereto:

Formula 201A

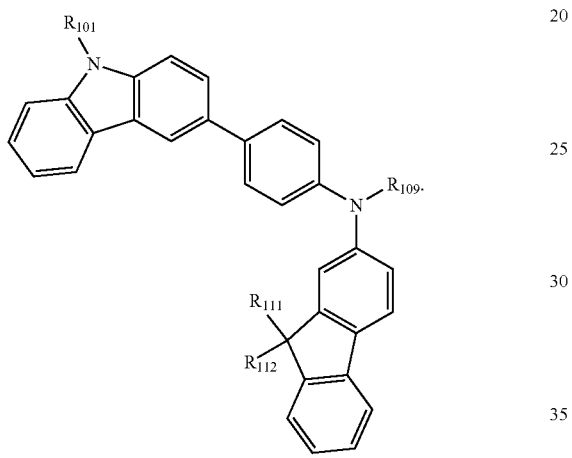

$R_{101}$, $R_{111}$, $R_{112}$, and $R_{109}$ in Formula 201A may be the same as described above.

For example, the compound represented by Formula 201 and the compound represented by Formula 202 may be selected from compounds HT1 to HT20 illustrated below, but embodiments of the present disclosure are not limited thereto.

HT1

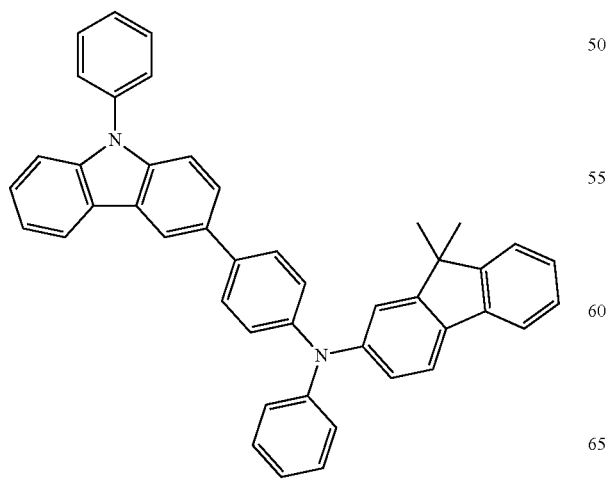

-continued

HT2

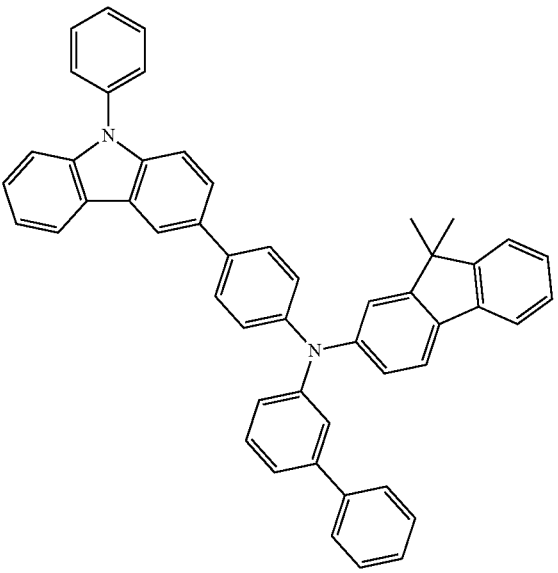

HT3

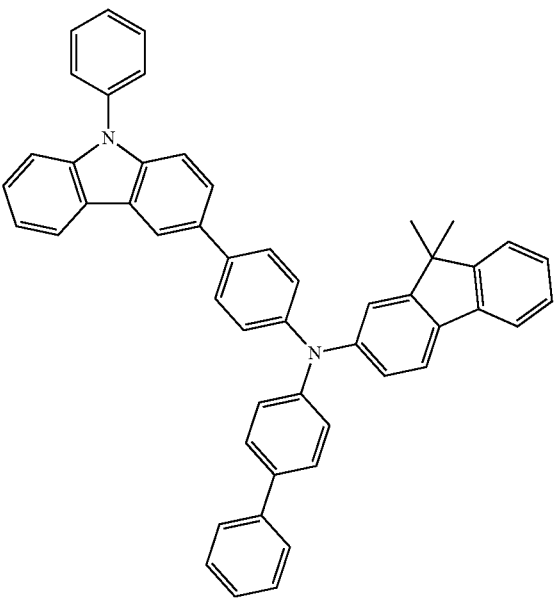

HT4
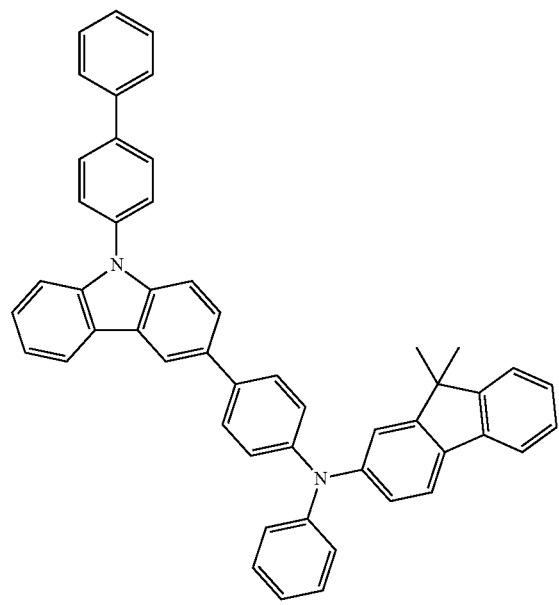
HT5
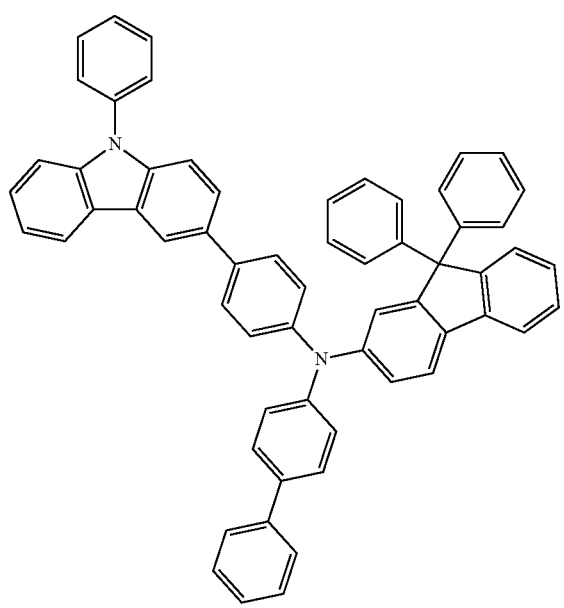
HT6
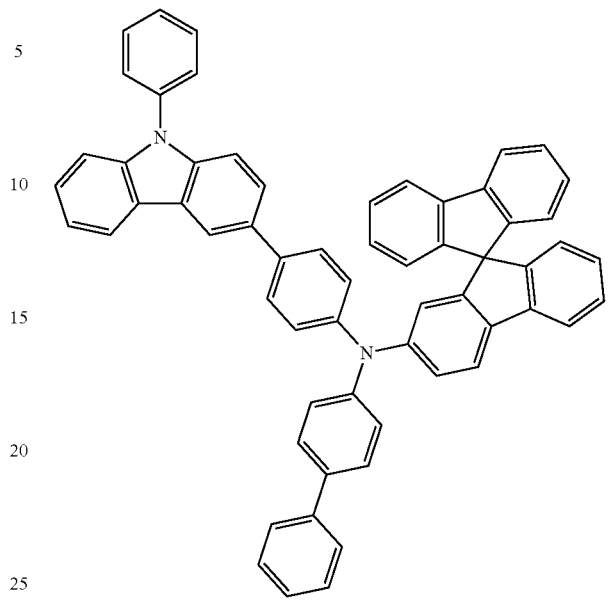
HT7
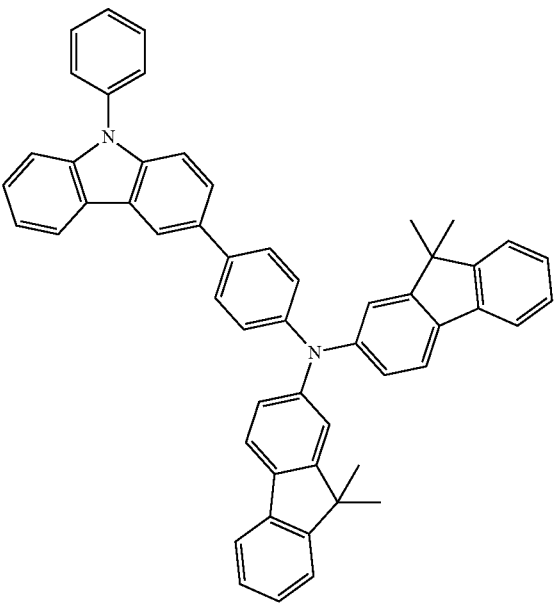

HT8
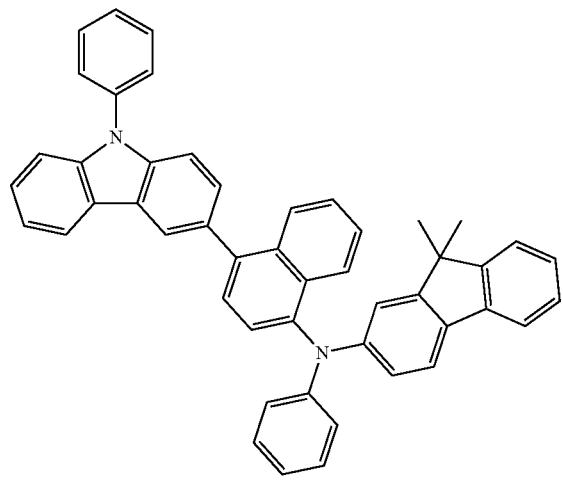
HT9
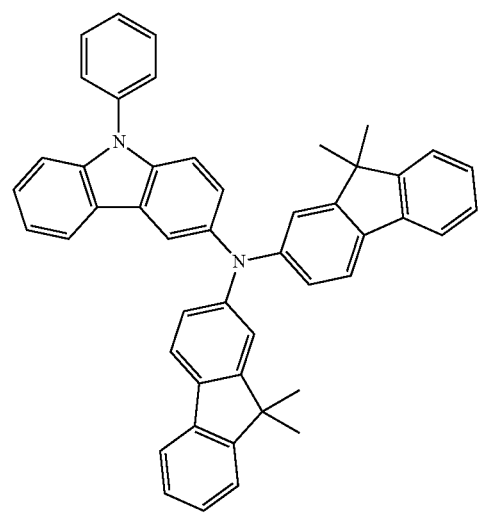
HT10
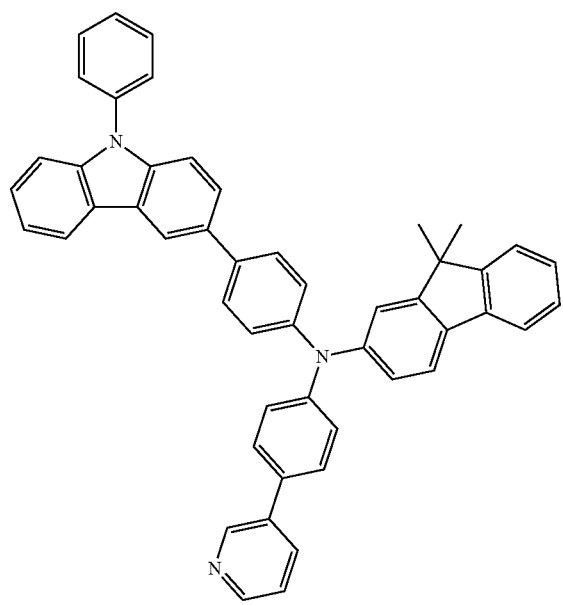
HT11
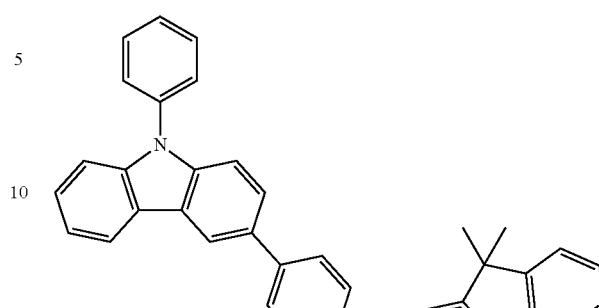
HT12
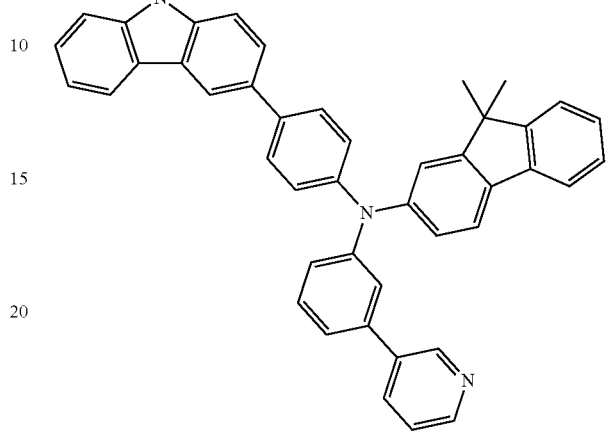
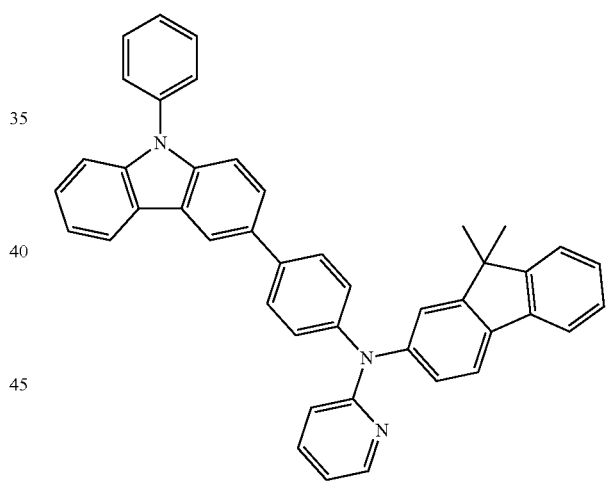
HT13
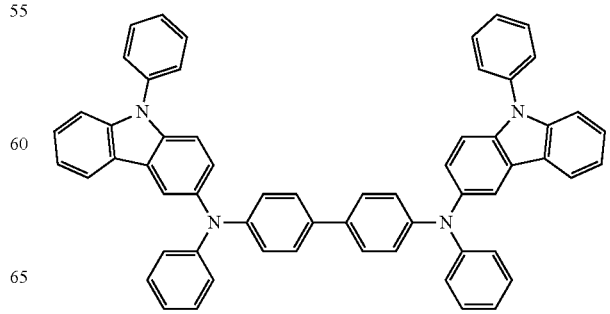

HT14

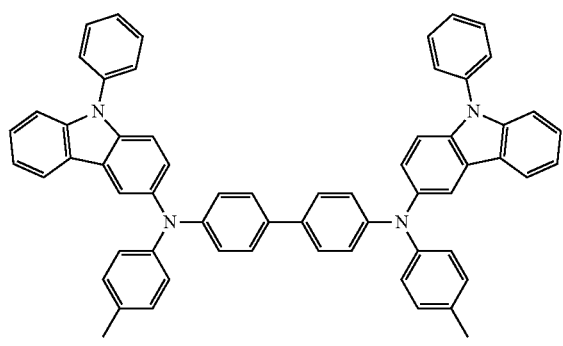

HT15

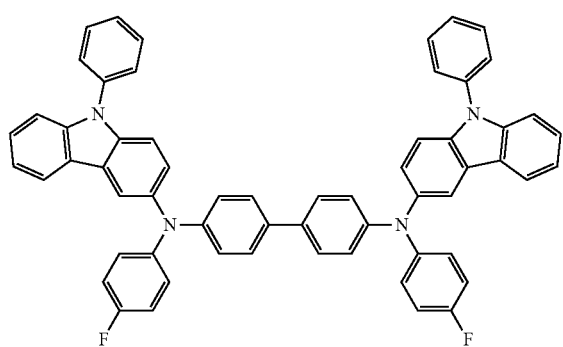

HT16

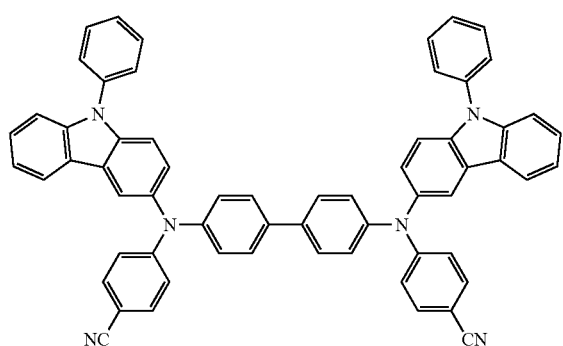

HT17

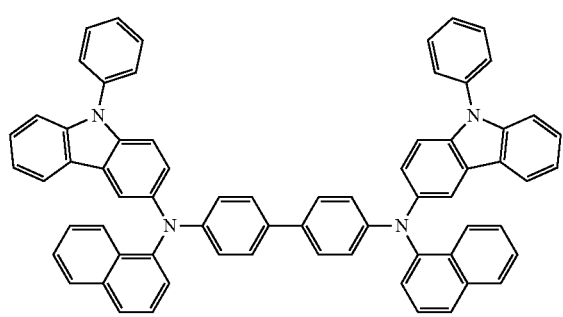

HT18

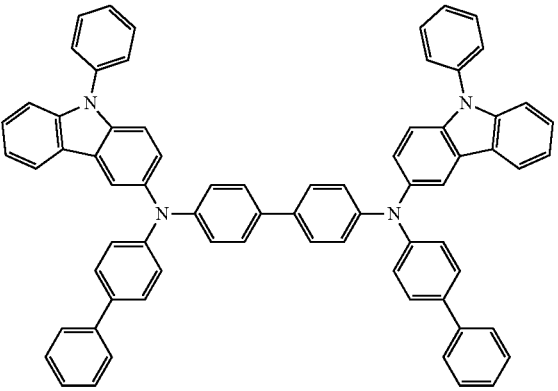

HT19

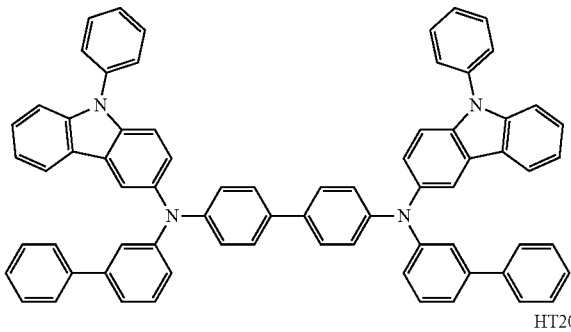

HT20

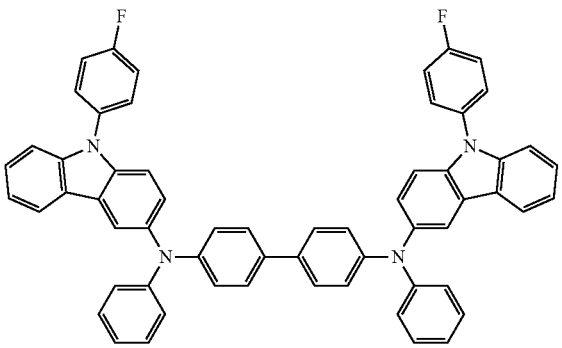

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 below, but embodiments of the present disclosure are not limited thereto.

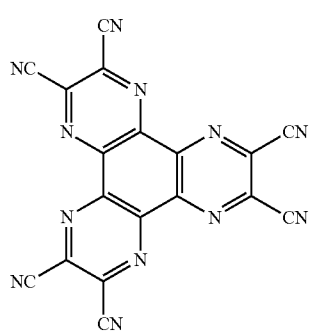

Compound HT-D1

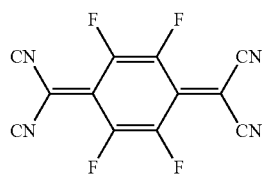

F4-TCNQ

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

Meanwhile, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected from TPBi, TBADN, ADN (also referred to as "DNA"), CBP, CDBP, TCP, mCP, Compound H50, and Compound H51:

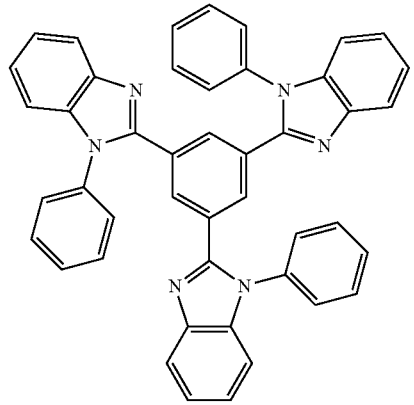

TPBi

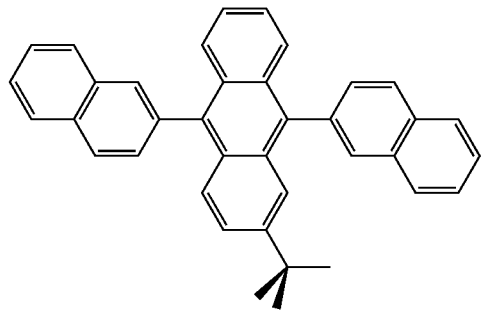

TBADN

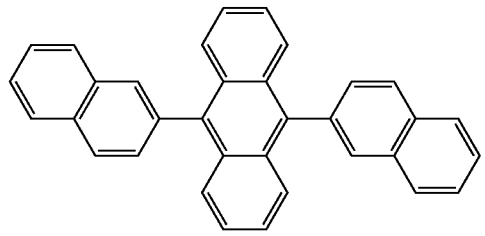

ADN

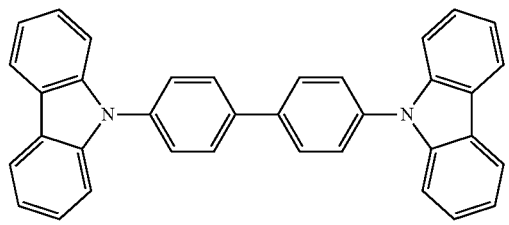

CBP

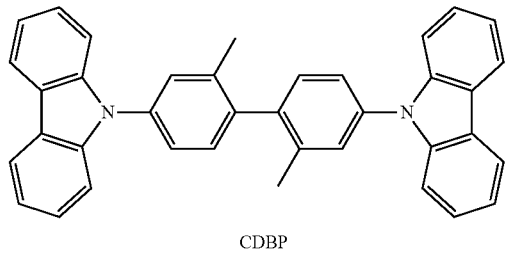

CDBP

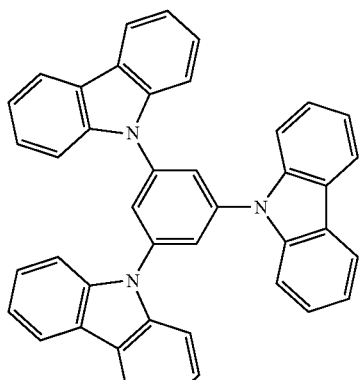

TCP

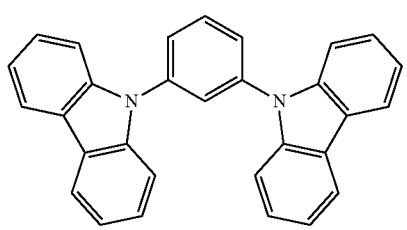

mCP

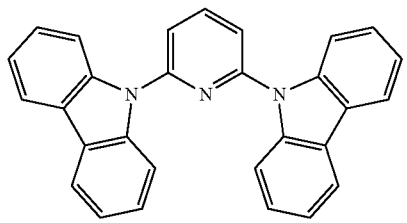

Compound H50

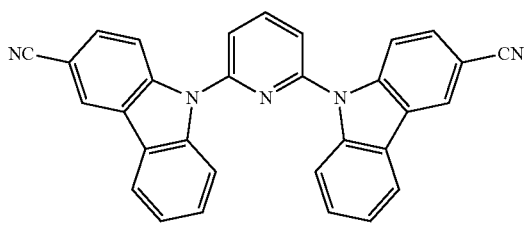

Compound H51

In one or more embodiments, the host may further include a compound represented by Formula 301 below.

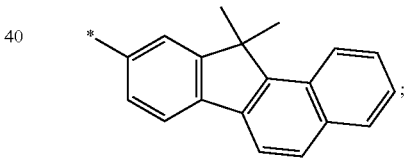

Formula 301

$Ar_{111}$ to $Ar_{112}$ in Formula 301 may each independently be selected from:
a phenylene group, a naphthylene group, a phenanthrenylene group, and a pyrenylene group; and
a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may each independently be selected from:
a $C_1$-$C_{10}$ alkyl group, a phenyl group, a naphthyl group, a phenanthrenyl group, and a pyrenyl group; and
a phenyl group, a naphthyl group, a phenanthrenyl group, and a pyrenyl group, each substituted with at least one selected from a phenyl group, a naphthyl group, and an anthracenyl group.

g, h, i, and j in Formula 301 may each independently be an integer from 0 to 4, and may be, for example, 0, 1, or 2.

$Ar_{113}$ to $Ar_{116}$ in Formula 301 may each independently be selected from:
a $C_1$-$C_{10}$ alkyl group, substituted with at least one selected from a phenyl group, a naphthyl group, and an anthracenyl group;
a phenyl group, a naphthyl group, an anthracenyl group, a pyrenyl, a phenanthrenyl group, and a fluorenyl group;
a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

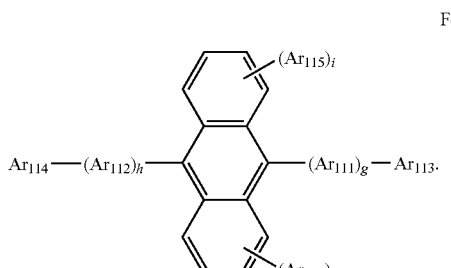

but embodiments of the present disclosure are not limited thereto.

In one or more embodiments, the host may include a compound represented by Formula 302 below:

Formula 302

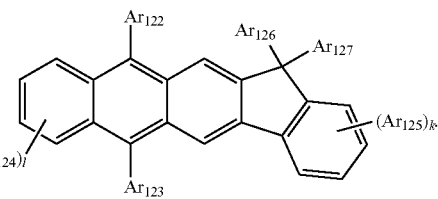

$Ar_{122}$ to $Ar_{125}$ in Formula 302 are the same as described in detail in connection with $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer from 0 to 4. For example, k and l may be 0, 1, or 2.
The compound represented by Formula 301 and the compound represented by Formula 302 may include Compounds H1 to H42 illustrated below, but embodiments of the present disclosure are not limited thereto:
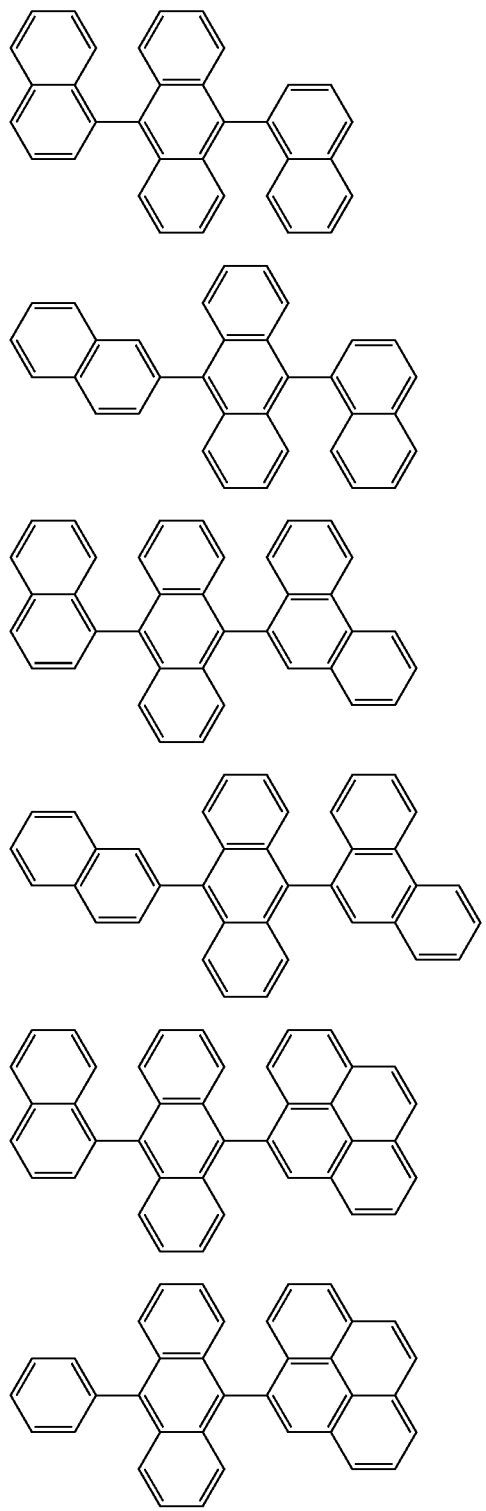
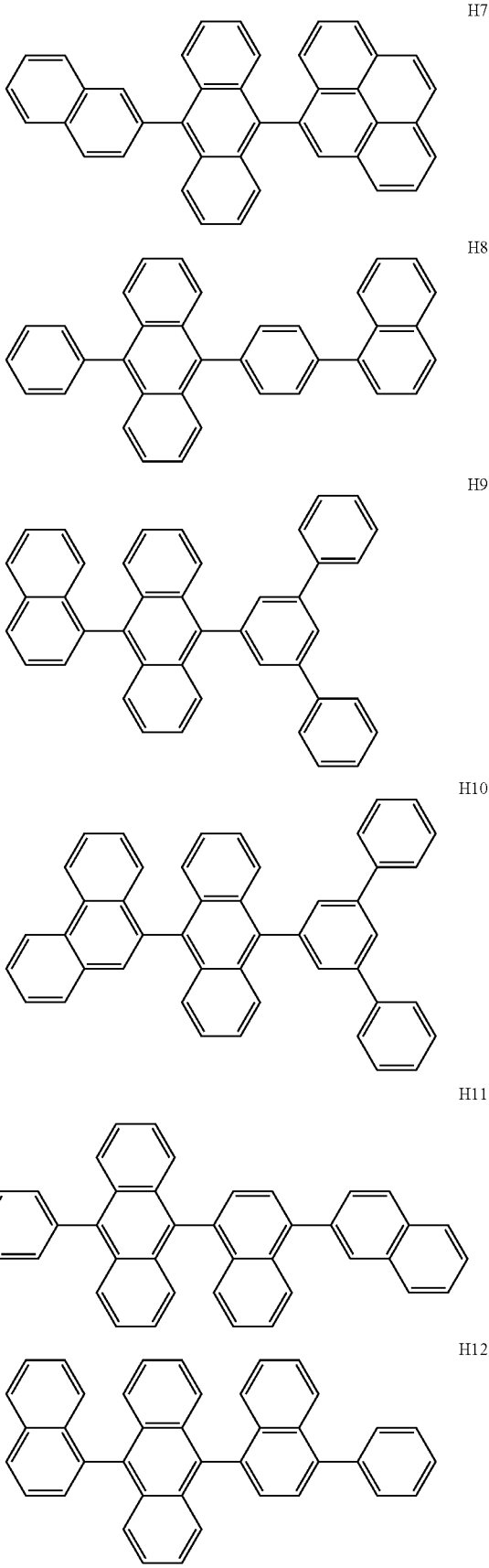

H13
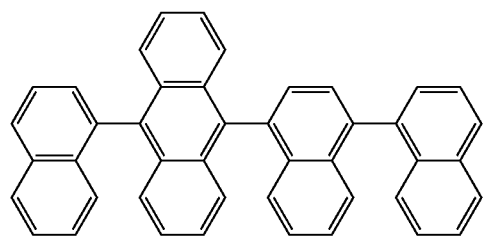
H14
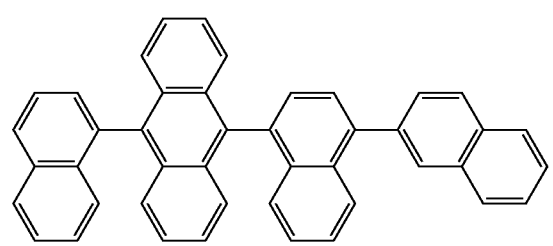
H15
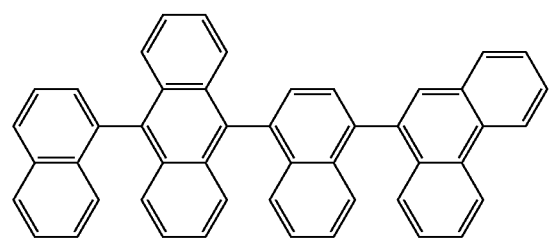
H16
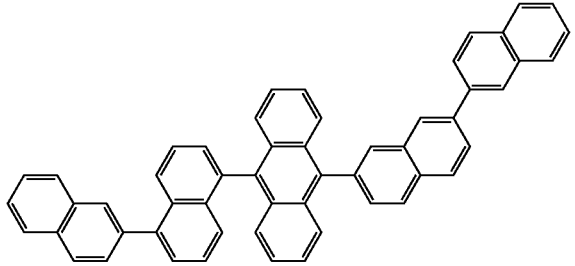
H17
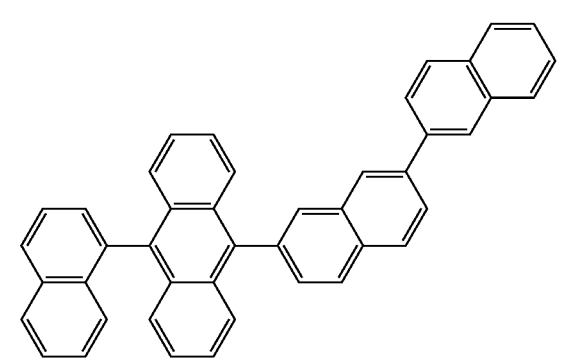
H18
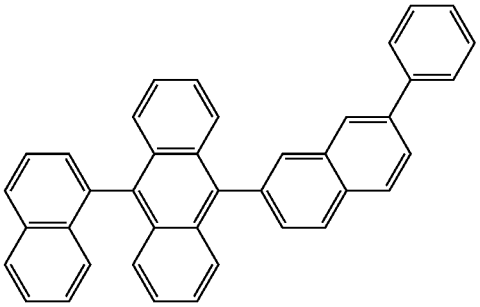
H19
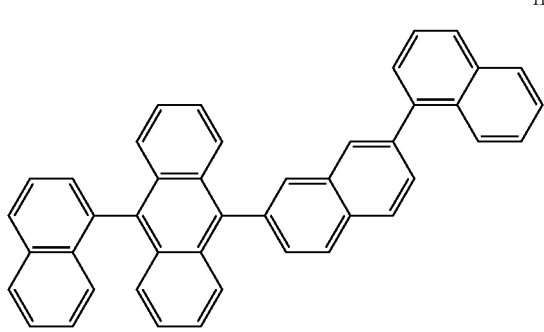
H20
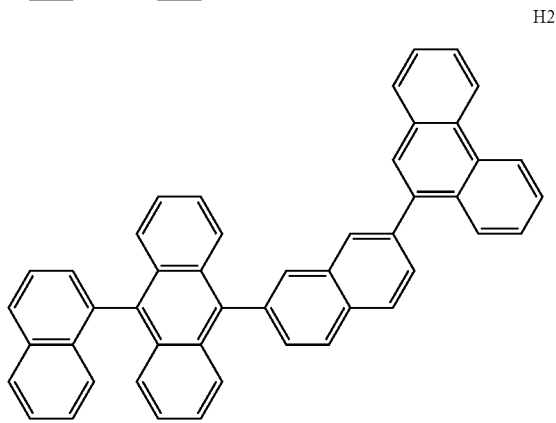
H21
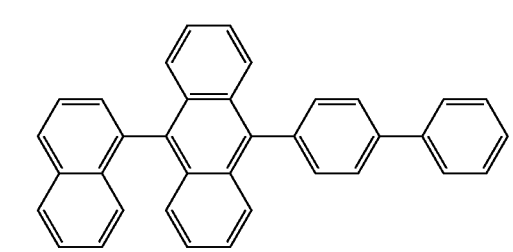
H22
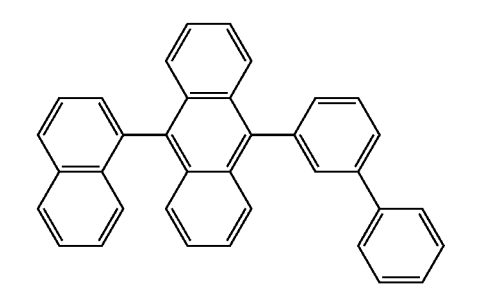

H23
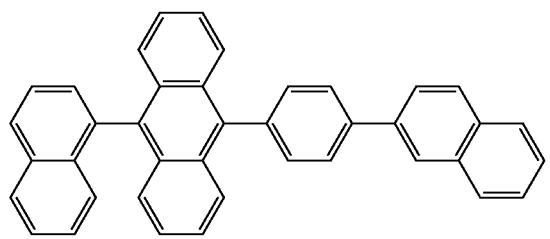
H24
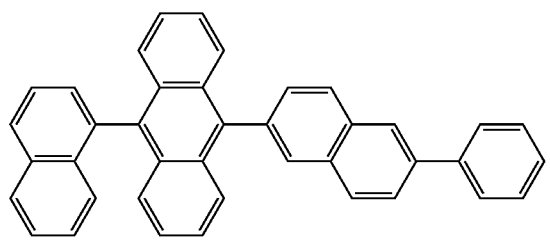
H25
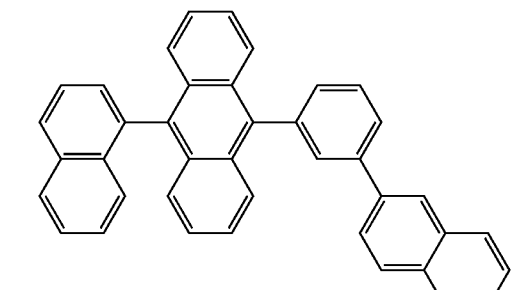
H26
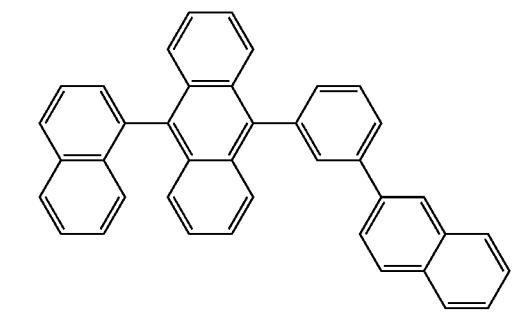
H27
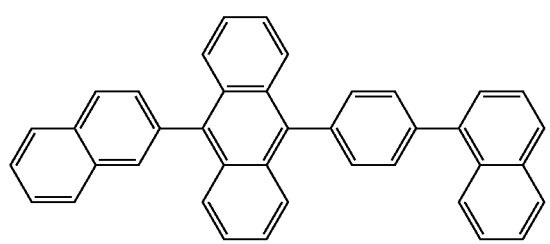
H28
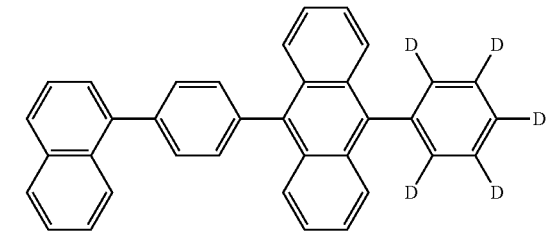
H29
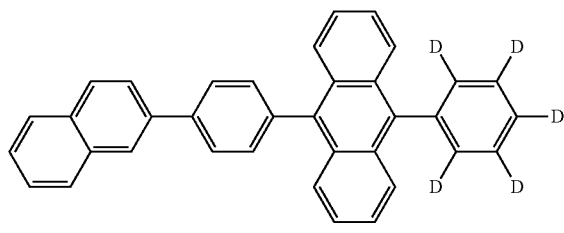
H30
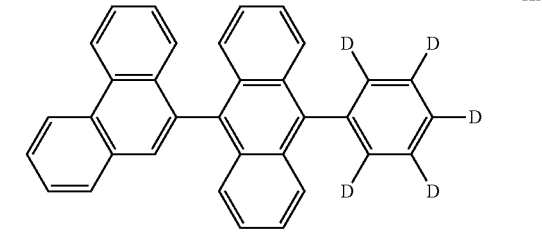
H31
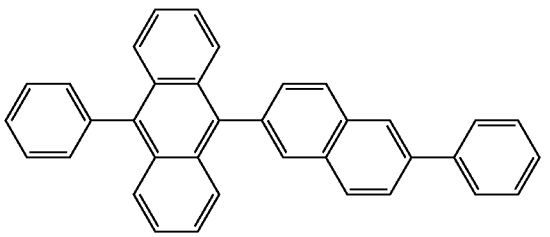
H32
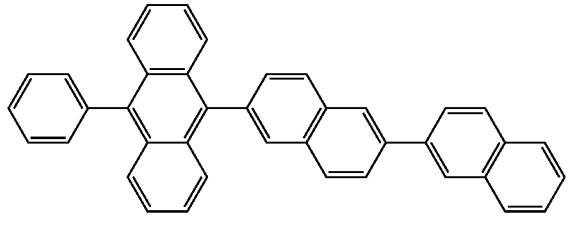
H33
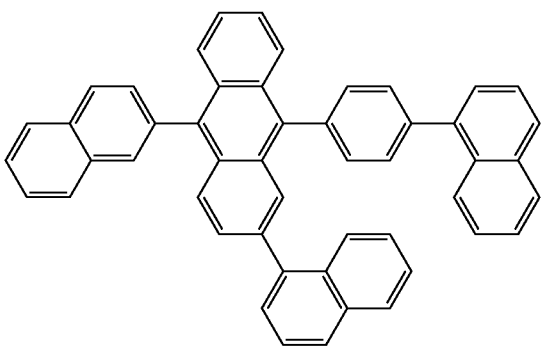

H34
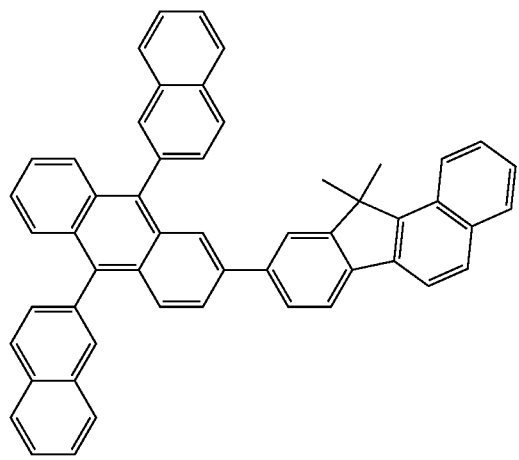
H35
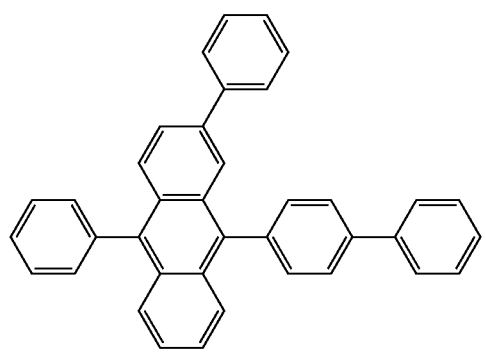
H36
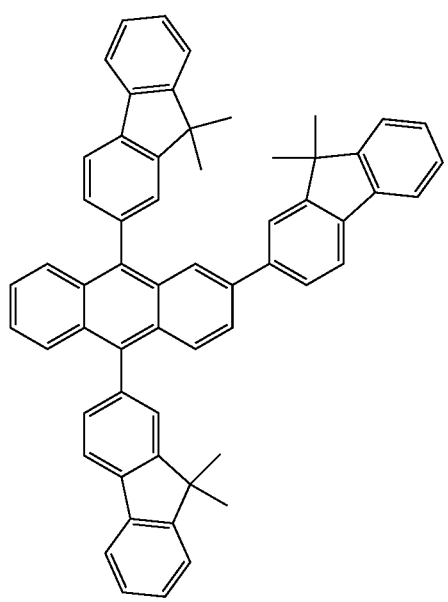
H37
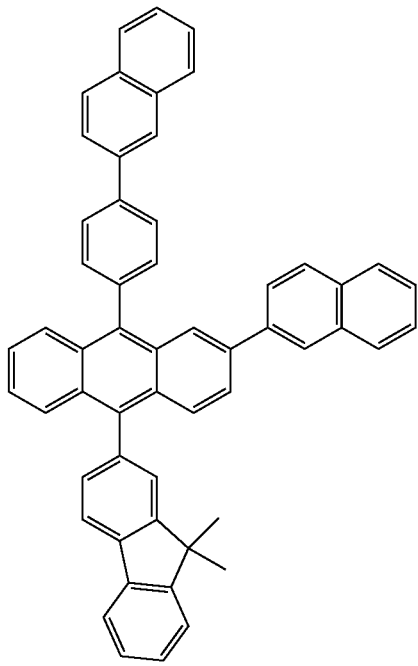
H38
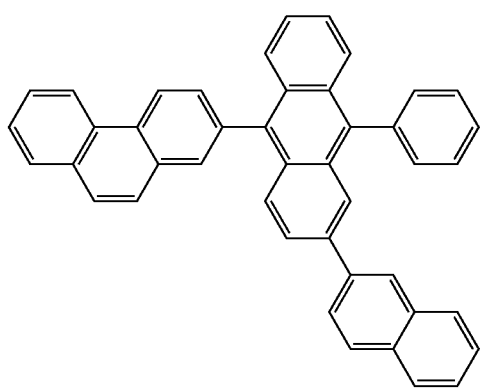
H39
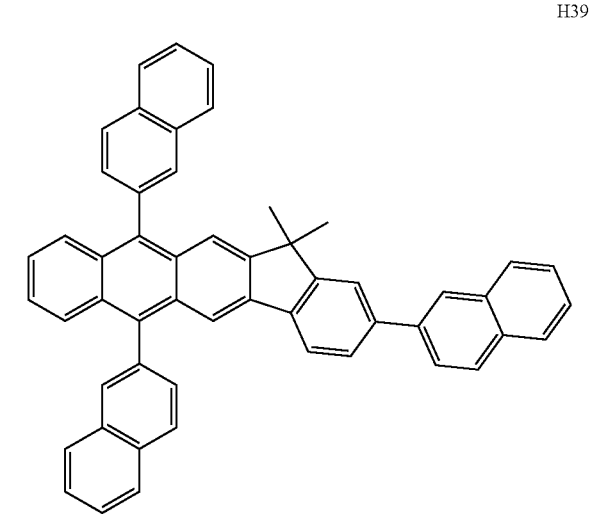

H40

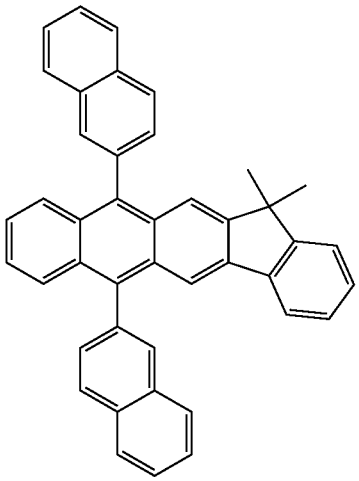

H41

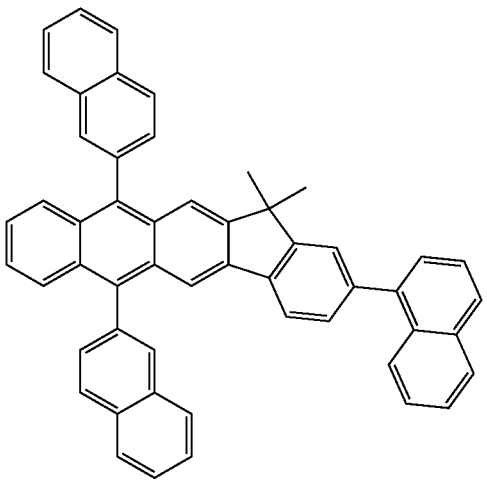

H42

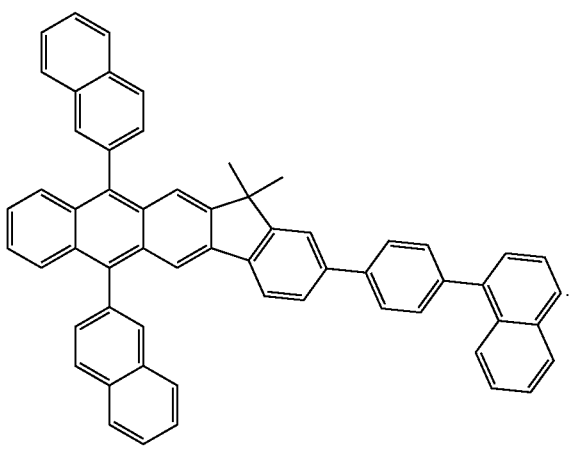

When the organic light-emitting device is a full-color organic light-emitting device, the emission layer may be patterned into a red emission layer, a green emission layer, and a blue emission layer. In one or more embodiments, due to a stack structure including a red emission layer, a green emission layer, and/or a blue emission layer, the emission layer may emit white light.

When the emission layer includes a host and a dopant, an amount of the dopant may be in a range of about 0.01 parts to about 15 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light emission characteristics may be obtained without a substantial increase in driving voltage.

Then, an electron transport region may be disposed on the emission layer.

The electron transport region may include a hole blocking layer, an electron transport layer, an electron injection layer, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one selected from BCP, Bphen, and BAlq but is not limited thereto.

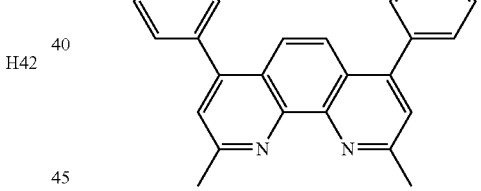

BCP

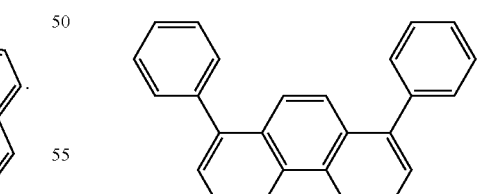

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include at least one selected from BCP, Bphen, Alq$_3$, BAlq, TAZ, and NTAZ:

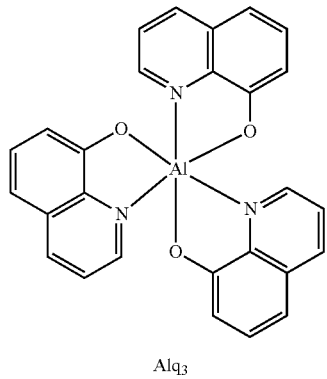

Alq$_3$

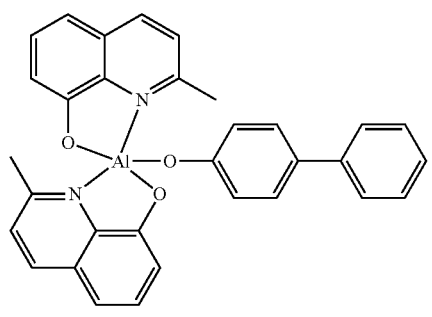

BAlq

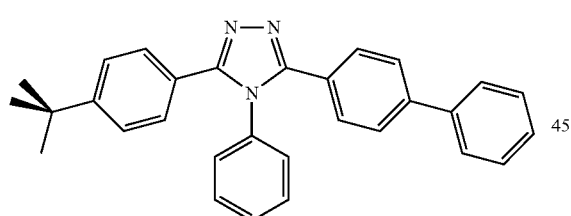

TAZ

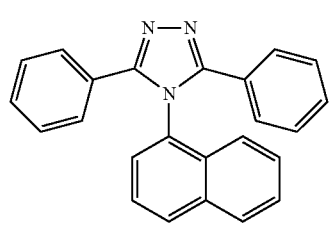

NTAZ

In one or more embodiments, the electron transport layer may include at least one of ET1 and ET2, but embodiments of the present disclosure are not limited thereto:

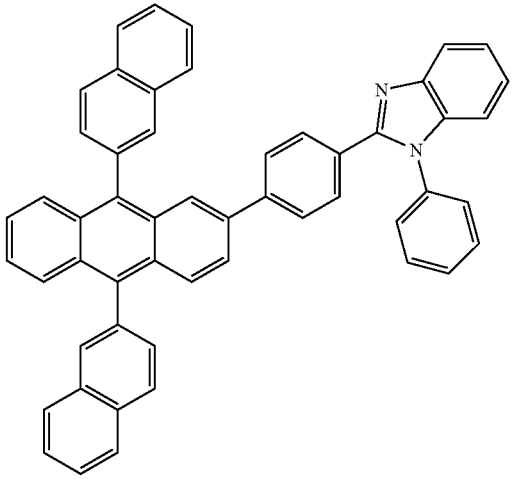

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

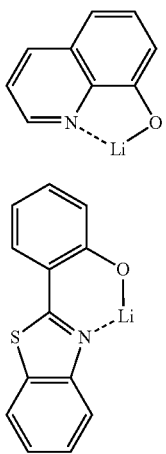

ET-D1

ET-D2

The electron transport region may include an electron injection layer (EIL) that promotes flow of electrons from the second electrode 19 thereinto.

The electron injection layer may include at least one selected from LiF, NaCl, CsF, $Li_2O$, and BaO.

A thickness of the electron injection layer may be in a range of about 1 Å to about 100 Å, and, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device has been described with reference to FIG. 1, but is not limited thereto.

Another aspect provides a diagnosis composition including at least one organometallic compound represented by Formula 1.

The organometallic compound represented by Formula 1 provides high luminescent efficiency. Accordingly, a diagnosis composition including the organometallic compound may have high diagnosis efficiency.

The diagnosis composition may be used in various applications including a diagnosis kit, a diagnosis reagent, a biosensor, and a biomarker.

The term "$C_1$-$C_{60}$ alkyl group" as used herein refers to a linear or branched saturated aliphatic hydrocarbon monovalent group having 1 to 60 carbon atoms, and non-limiting examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an iso-propyloxy (iso-propoxy) group.

The term "$C_2$-$C_{60}$ alkenyl group" as used herein refers to a hydrocarbon group formed by including at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group formed by including at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si, and S as a ring-forming atom and 1 to 10 carbon atoms, and non-limiting examples thereof include a tetrahydrofuranyl group and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms, at least one carbon-carbon double bond in the ring thereof, and no aromaticity. Non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Examples of the $C_1$-$C_{10}$ heterocycloalkenyl group are a 2,3-dihydrofuranyl group and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a cyclic aromatic system that has at least one heteroatom selected from N, O, P, Si, and S as a ring-forming atom, and 1 to 60 carbon atoms. The term "$C_1$-$C_{60}$ heteroarylene group" as used herein refers to a divalent group having a carbocyclic aromatic system that has at least one heteroatom selected from N, O, P, Si, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group," as used herein, refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group," as used herein, refers to a divalent group having the same structure as the monovalent non-aromatic condensed heteropolycyclic group.

The term "$C_5$-$C_{30}$ carbocyclic group" as used herein refers to a saturated or unsaturated cyclic group having, as ring-forming atoms, 5 to 30 carbon atoms only. The $C_5$-$C_{30}$ carbocyclic group may be a monocyclic group or a polycyclic group.

The term "$C_1$-$C_{30}$ heterocyclic group" as used herein refers to a saturated or unsaturated cyclic group having, as a ring-forming atom, at least one heteroatom selected from N, O, Si, P, and S other than 1 to 30 carbon atoms. The $C_1$-$C_{30}$ heterocyclic group may be a monocyclic group or a polycyclic group.

At least one substituent of the substituted $C_5$-$C_{30}$ carbocyclic group, the substituted $C_2$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$ and —$P(=O)(Q_{28})(Q_{29})$;

—$N(Q_{31})(Q_{32})$, —$Si(Q_{33})(Q_{34})(Q_{35})$, —$B(Q_{36})(Q_{37})$ and —$P(=O)(Q_{38})(Q_{39})$; and $Q_1$ to $Q_9$, $Q_{11}$ to $Q_{19}$, $Q_{21}$ to $Q_{29}$, and $Q_{31}$ to $Q_{39}$ may each independently be selected from a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ alkyl group, and a $C_6$-$C_{60}$ aryl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device according to embodiments are described in detail with reference to Synthesis Examples and Examples. However, the organic light-emitting device is not limited thereto. The wording "B was used instead of A" used in describing Synthesis Examples means that the number of molar equivalents of A used was identical to the number of molar equivalents of B.

EXAMPLES

Synthesis Example 1: Synthesis of Compound 1

Compound 1 was synthesized according to the Reaction Scheme 1.

Reaction Scheme 1

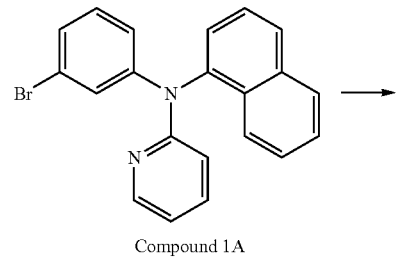

Compound 1A

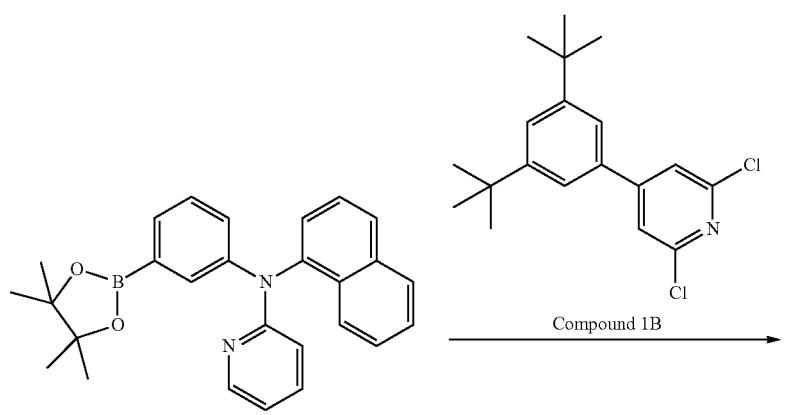

Intermediate 1-3    Compound 1B

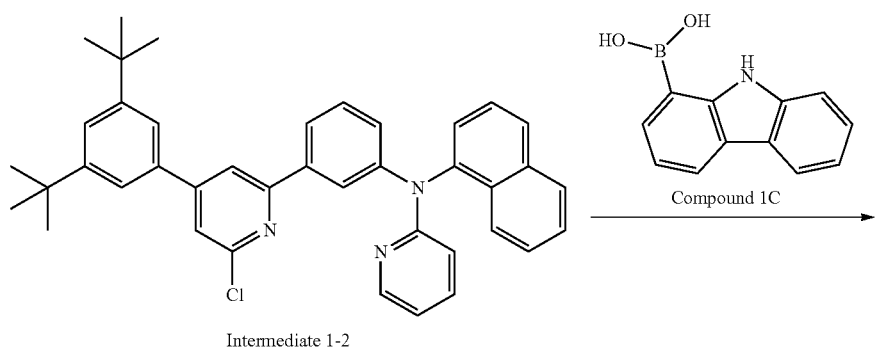

Intermediate 1-2    Compound 1C

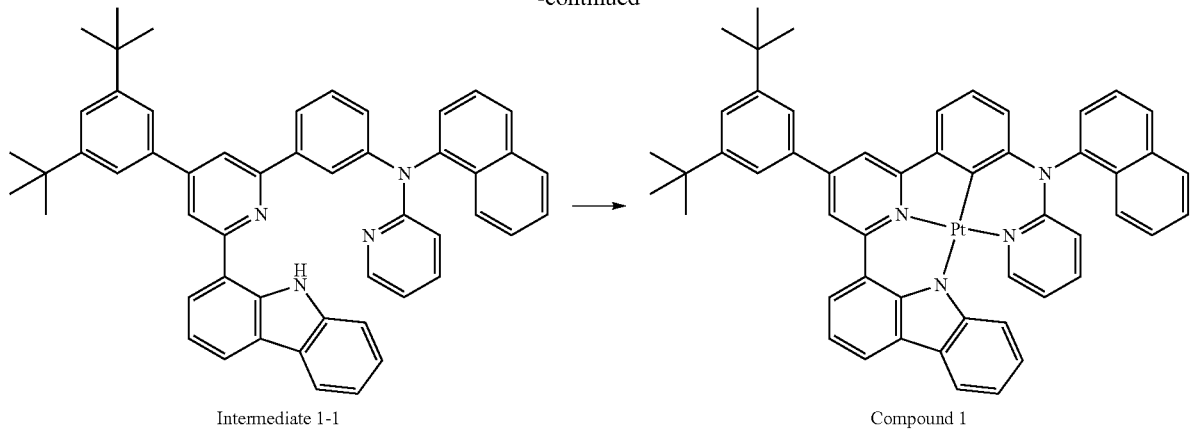

Intermediate 1-1 → Compound 1

1) Synthesis of Intermediate 1-3

4.0 grams (g) (10.66 millimoles, mmol) of Compound 1A, 3.3 g (12.80 mmol) of bis(pinacolato)diboron, 3.1 g (31.98 mmol) of potassium acetate, and 0.78 g (1.07 mmol) of Pd(dppf)$_2$Cl$_2$ were mixed with 150 milliliters (ml) of toluene, and the mixture was heated to a temperature of 120° C. and stirred for 8 hours under reflux. The reactant obtained therefrom was cooled to room temperature. The organic layer was extracted by using 300 ml of water and 300 ml of ethyl acetate. The organic layer was dried by using MgSO$_4$ and a solvent was evaporated. The residue obtained therefrom was separated and purified by silica gel column chromatography, thereby completing the preparation of 2.1 g (58%) of Intermediate 1-3. The obtained compound was identified by LC-MS.

LC-MS m/z=341.14 (M+H)$^+$

2) Synthesis of Intermediate 1-2

2.1 g (6.17 mmol) of Intermediate 1-3, 1.73 g (5.144 mmol) of Compound 1B, 1.36 g (12.86 mmol) of sodium carbonate, and 0.4 g (0.36 mmol) of Pd(PPh$_3$)$_4$ were mixed with 90 ml of tetrahydrofuran (THF), 30 ml of distilled water, and 30 ml of ethanol, and the mixture was heated to a temperature of 100 QC and stirred for 16 hours under reflux. The reactant obtained therefrom was cooled to room temperature. The organic layer was extracted by using 200 ml of water and 200 ml of ethyl acetate. The organic layer was dried by using MgSO$_4$, and a solvent was evaporated. The residue obtained therefrom was separated and purified by silica gel column chromatography, thereby completing the preparation of 2.47 g (81%) of Intermediate 1-2. The obtained compound was identified by LC-MS.

LC-MS m/z=596.28 (M+H)$^+$

3) Synthesis of Intermediate 1-1

2.47 g (4.14 mmol) of Intermediate 1-2, 1.14 g (5.39 mmol) of Compound 1C, 1.72 g (12.43 mmol) of sodium carbonate, and 0.34 g (0.29 mmol) of Pd(PPh$_3$)$_4$ were mixed with 90 ml of THF, 30 ml of distilled water, and 30 ml of ethanol, and the mixture was heated to a temperature of 100° C. and stirred for 16 hours under reflux. The reactant obtained therefrom was cooled to room temperature. The organic layer was extracted by using 200 ml of water and 200 ml of ethyl acetate. The organic layer was dried by using MgSO$_4$, and a solvent was evaporated. The residue obtained therefrom was separated and purified by silica gel column chromatography, thereby completing the preparation of 2.6 g (86%) of Intermediate 1-1. The obtained compound was identified by LC-MS.

LC-MS m/z=727.37 (M+H)$^+$

4) Synthesis of Compound 1

2.6 g (3.58 mmol) of Intermediate 1-1, 1.48 g (3.58 mmol) of potassium tetrachloroplatinate, and 100 ml of acetic acid were mixed, and the mixture was heated to a temperature of 130° C. and stirred for 16 hours under reflux. The reactant obtained therefrom was cooled to room temperature, and the organic layer was washed with a sodium bicarbonate aqueous solution, water, and extracted with 200 ml of ethyl acetate. The organic layer was dried by using MgSO$_4$ and a solvent was evaporated. The residue obtained therefrom was separated and purified by silica gel column chromatography, thereby completing the preparation of 1.48 g (45%) of Compound 1. The obtained compound was identified by LC-MS.

LC-MS m/z=920.32 (M+H)$^+$

Synthesis Example 2: Synthesis of Compound 2

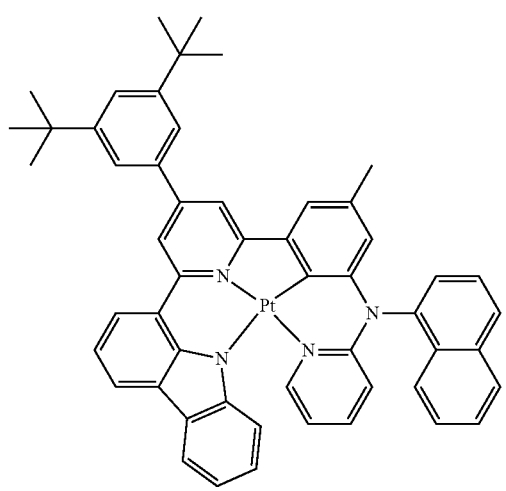

2

Compound 2 was synthesized in the same manner as in Synthesis Example 1, except that N-(3-bromo-5-methylphenyl)-N-(naphthalen-1-yl)pyridin-2-amine was used instead of Compound 1A in synthesizing Intermediate 1-3. The obtained compound was identified by LC-MS.

LC-MS m/z=934.34 (M+H)+

Synthesis Example 3: Synthesis of Compound 3

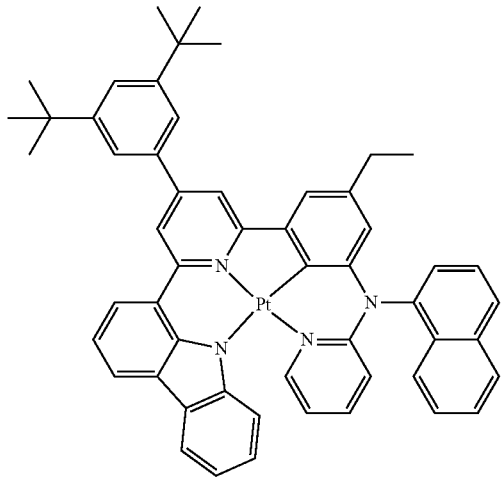

3

Compound 3 was synthesized in the same manner as in Synthesis Example 1, except that N-(3-bromo-5-ethylphenyl)-N-(naphthalen-1-yl)pyridin-2-amine was used instead of Compound 1A in synthesizing Intermediate 1-3. The obtained compound was identified by LC-MS.

LC-MS m/z=948.35 (M+H)+

Synthesis Example 4: Synthesis of Compound 7

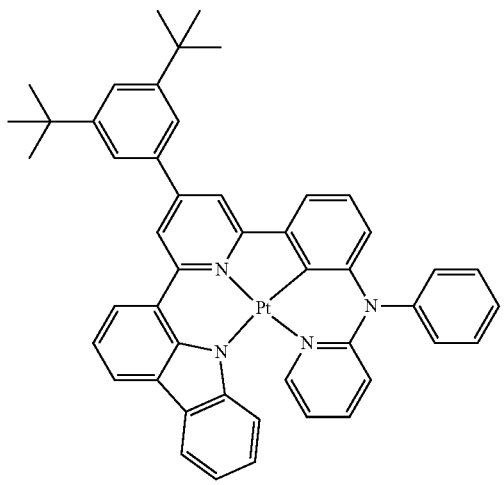

7

Compound 7 was synthesized in the same manner as in Synthesis Example 1, except that N-(3-bromophenyl)-N-phenylpyridin-2-amine was used instead of Compound 1A in synthesizing Intermediate 1-3. The obtained compound was identified by LC-MS.

LC-MS m/z=870.31 (M+H)+

Synthesis Example 5: Synthesis of Compound 8

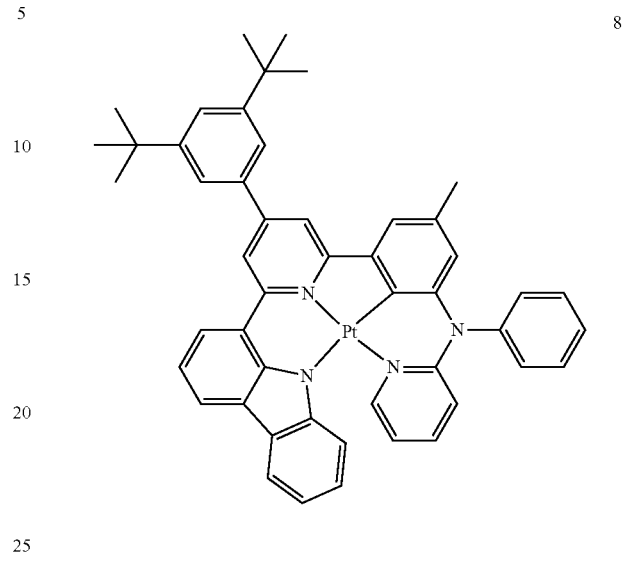

8

Compound 8 was synthesized in the same manner as in Synthesis Example 1, except that N-(3-bromo-5-methylphenyl)-N-phenylpyridin-2-amine was used instead of Compound 1A in synthesizing Intermediate 1-3. The obtained compound was identified by LC-MS.

LC-MS m/z=884.32 (M+H)+

Synthesis Example 6: Synthesis of Compound 9

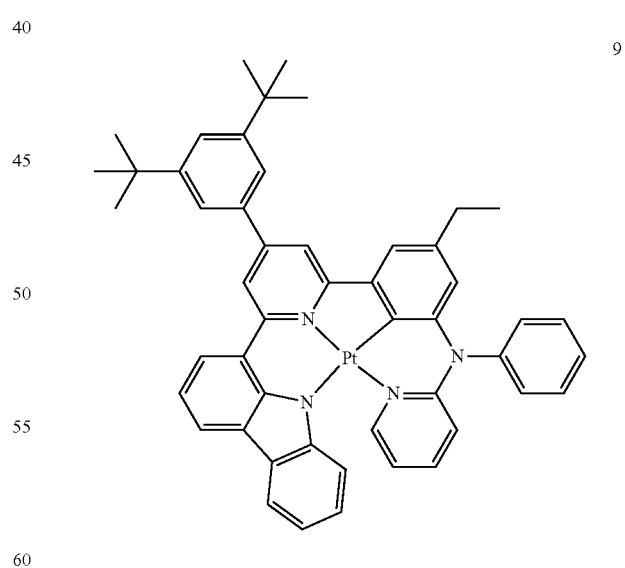

9

Compound 9 was synthesized in the same manner as in Synthesis Example 1, except that N-(3-bromo-5-ethylphenyl)-N-phenylpyridin-2-amine was used instead of Compound 1A in synthesizing Intermediate 1-3. The obtained compound was identified by LC-MS.

LC-MS m/z=898.34 (M+H)+

Synthesis Example 7: Synthesis of Compound 19

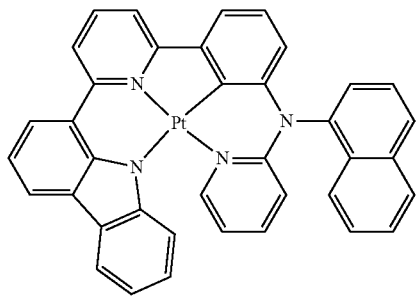

19

Compound 19 was synthesized in the same manner as in Synthesis Example 1, except that 2,6-dichloropyridine was used instead of Compound 1B in synthesizing Intermediate 1-2. The obtained compound was identified by LC-MS.
LC-MS m/z=732.16 (M+H)$^+$ Synthesis Example 8: Synthesis of Compound 20

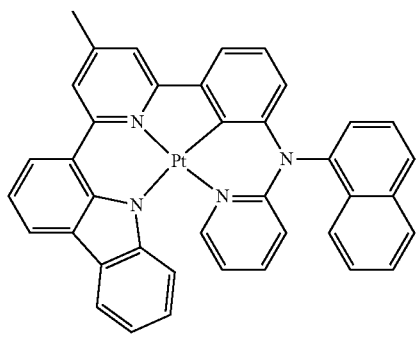

20

Compound 20 was synthesized in the same manner as in Synthesis Example 1, except that 2,6-dichloro-4-methyl-pyridine was used instead of Compound 1B in synthesizing Intermediate 1-2. The obtained compound was identified by LC-MS.
LC-MS m/z=746.18 (M+H)$^+$ Synthesis Example 9: Synthesis of Compound 21

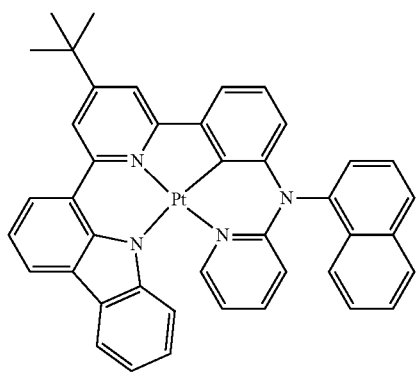

21

Compound 21 was synthesized in the same manner as in Synthesis Example 1, except that 4-(tert-butyl)-2,6-dichloropyridine was used instead of Compound 1B in synthesizing Intermediate 1-2. The obtained compound was identified by LC-MS.
LC-MS m/z=788.23 (M+H)$^+$ Synthesis Example 10: Synthesis of Compound 25

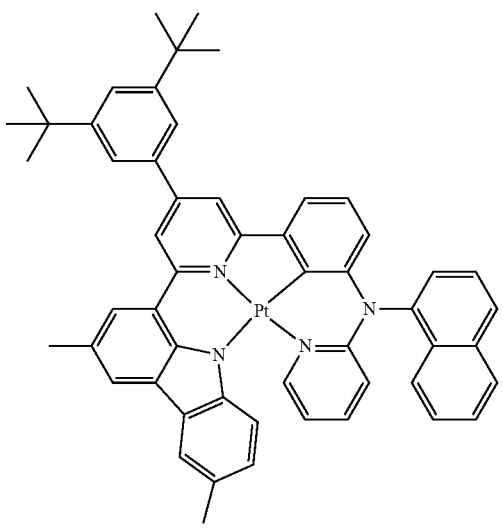

25

Compound 25 was synthesized in the same manner as in Synthesis Example 1, except that a (3,6-dimethyl-9H-carbazol-1-yl)boronic acid was used instead of Compound 1C in synthesizing Intermediate 1-1. The obtained compound was identified by LC-MS.
LC-MS m/z=948.35 (M+H)$^+$ Synthesis Example 11: Synthesis of Compound 28

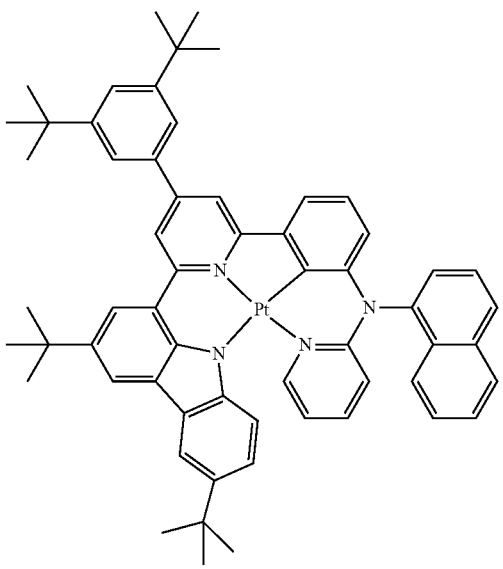

28

Compound 28 was synthesized in the same manner as in Synthesis Example 1, except that a (3,6-di-tert-butyl-9H-carbazol-1-yl)boronic acid was used instead of Compound 1C in synthesizing Intermediate 1-1. The obtained compound was identified by LC-MS.

LC-MS m/z=1032.45 (M+H)+

Synthesis Example 12: Synthesis of Compound 31

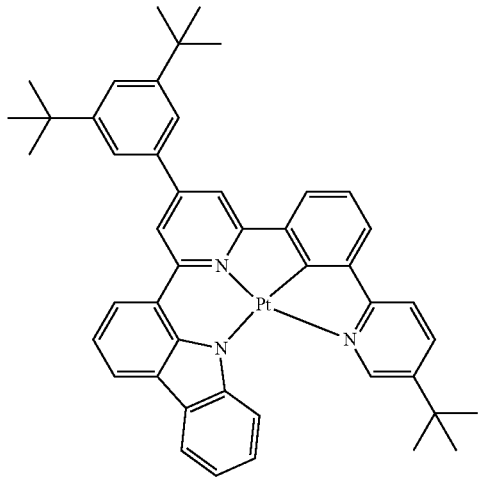

31

Compound 31 was synthesized in the same manner as in Synthesis Example 1, except that 2-(3-bromophenyl)-5-(tert-butyl)pyridine was used instead of Compound 1A in synthesizing Intermediate 1-3. The obtained compound was identified by LC-MS.

LC-MS m/z=835.33 (M+H)+

Synthesis Example 13: Synthesis of Compound 32

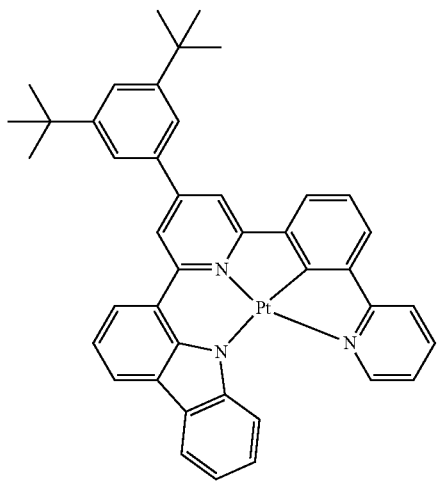

32

Compound 32 was synthesized in the same manner as in Synthesis Example 1, except that 2-(3-bromophenyl)pyridine was used instead of Compound 1A in synthesizing Intermediate 1-3. The obtained compound was identified by LC-MS.

LC-MS m/z=779.26 (M+H)+

Synthesis Example 14: Synthesis of Compound 41

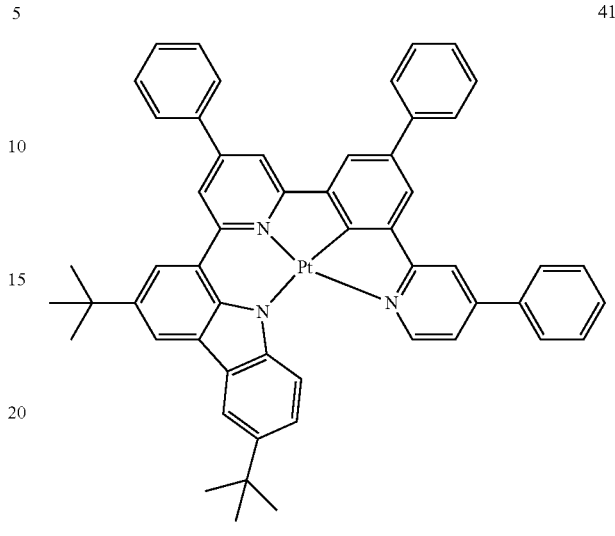

41

Compound 41 was synthesized in the same manner as in Synthesis Example 1, except that, in forming Compound 1, 2-(5-bromo-[1,1'-biphenyl]-3-yl)-4-phenylpyridine was used instead of Compound 1A, and a (3,6-di-tert-butyl-9H-carbazol-1-yl)boronic acid was used instead of Compound 1C. The obtained compound was identified by LC-MS.

LC-MS m/z=931.33 (M+H)+

Synthesis Example 15: Synthesis of Compound 103

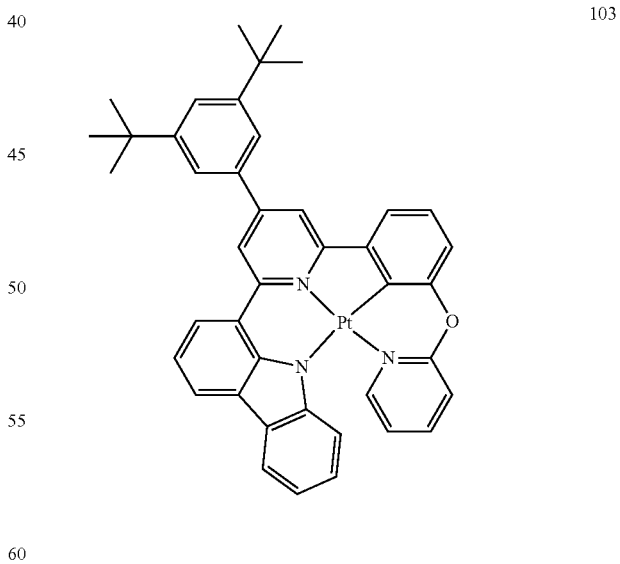

103

Compound 103 was synthesized in the same manner as in Synthesis Example 1, except that 2-(3-bromophenoxy)pyridine was used instead of Compound 1A in synthesizing Intermediate 1-3. The obtained compound was identified by LC-MS.

LC-MS m/z=795.26 (M+H)+

Synthesis Example 16: Synthesis of Compound 115

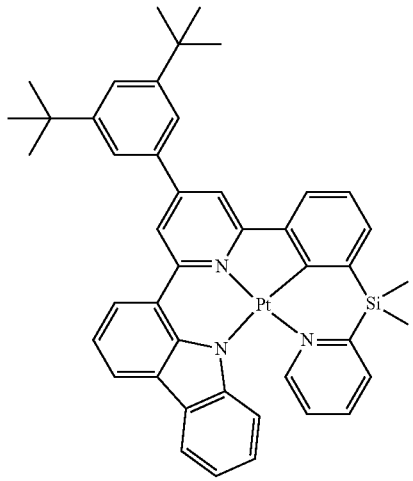

Compound 115 was synthesized in the same manner as in Synthesis Example 1, except that 2-((3-bromophenyl)dimethylsilyl)pyridine was used instead of Compound 1A in synthesizing Intermediate 1-3. The obtained compound was identified by LC-MS.

LC-MS m/z=837.29 (M+H)$^+$

Example 1

An ITO glass substrate was cut to a size of 50 mm×50 mm×0.5 mm (mm=millimeters), sonicated in acetone, isopropyl alcohol, and pure water each for 15 minutes, and then, washed by exposing the ITO glass substrate to UV irradiation and ozone for 30 minutes.

Then, m-MTDATA was deposited on an ITO electrode (anode) of the ITO glass substrate at a deposition rate of 1 Angstroms per second (Å/sec) to form a hole injection layer having a thickness of 600 Angstroms (Å), and then, α-NPD was deposited on the hole injection layer at a deposition rate of 1 Å/sec to form a hole transport layer having a thickness of 250 Å.

Compound 1 (dopant) and CBP (host) were each co-deposited on the hole transport layer at a deposition rate of 0.1 Å/sec and 1 Å/sec to form an emission layer having a thickness of 400 Å.

BAlq was deposited on the emission layer at a deposition rate of 1 Å/sec to form a hole blocking layer having a thickness of 50 Å, Alq$_3$ was deposited on the hole blocking layer to form an electron transport layer having a thickness of 300 Å, LiF was deposited on the electron transport layer to form an electron injection layer having a thickness of 10 Å, and Al was vacuum-deposited on the electron injection layer to form a second electrode (cathode) having a thickness of 1,200 Å, thereby completing the manufacture of an organic light-emitting device having a structure of ITO/m-MTDATA (600 Å)/α-NPD (250 Å)/CBP+10% (Compound 1) (400 Å)/Balq (50 Å)/Alq$_3$ (300 Å)/LiF (10 Å)/Al (1,200 Å).

Examples 2 to 4 and Comparative Example 1

Organic light-emitting devices of Examples 2 to 4 and Comparative Example 1 were manufactured in the same manner as in Example 1, except that Compounds shown in Table 2 were each used instead of Compound 1 as a dopant in forming an emission layer.

Evaluation Example: Evaluation of Characteristics of Organic Light-Emitting Devices The driving voltage, efficiency, power, color purity, quantum efficiency, and roll-off ratio of the organic light-emitting devices manufactured according to Examples 1 to 4 and Comparative Example 1 were evaluated. Results thereof are shown in Table 2. This evaluation was performed by using a current-voltage meter (Keithley 2400) and a luminance meter (Minolta Cs-1000A). The roll-off ratio was calculated by Equation 20:

Roll-off ratio={1−(efficiency (at 9000 nit)/maximum emission efficiency)}×100%  Equation 20

TABLE 2

| | Dopant | Driving voltage (V) | Efficiency (cd/A) | Power (lm/W) | CIEx | CIEy | Quantum Efficiency (%) | Roll-off ratio (%) |
|---|---|---|---|---|---|---|---|---|
| Example 1 | Compound 1 | 3.809 | 41.426 | 34.168 | 0.576 | 0.42 | 20.64 | 7.8 |
| Example 2 | Compound 7 | 3.712 | 40.413 | 33.519 | 0.572 | 0.415 | 20.53 | 8.1 |
| Example 3 | Compound 31 | 3.365 | 65.547 | 61.214 | 0.512 | 0.481 | 22.78 | 4.8 |
| Example 4 | Compound 32 | 3.420 | 62.183 | 58.831 | 0.525 | 0.471 | 22.82 | 6.2 |
| Comparative Example 1 | Compound B | 5.371 | 16.461 | 9.63 | 0.642 | 0.354 | 13.32 | 25.5 |

TABLE 2-continued
| Dopant | Driving voltage (V) | Efficiency (cd/A) | Power (lm/W) | CIEx | CIEy | Quantum Efficiency (%) | Roll-off ratio (%) |
|---|---|---|---|---|---|---|---|
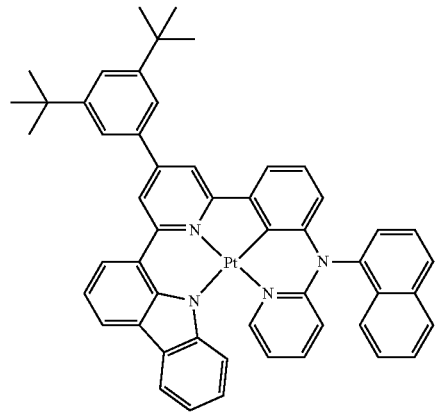
1
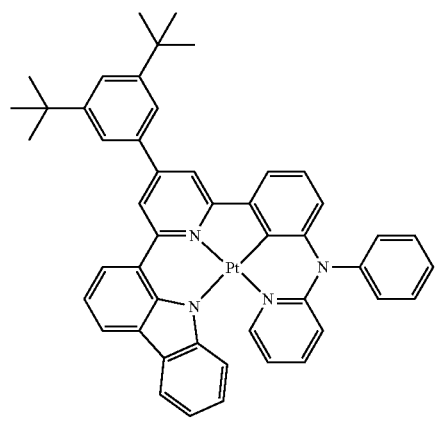
7
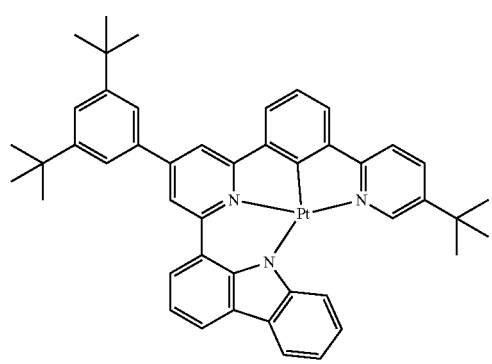
31

| | Dopant | Driving voltage (V) | Efficiency (cd/A) | Power (lm/W) | CIEx | CIEy | Quantum Efficiency (%) | Roll-off ratio (%) |
|---|---|---|---|---|---|---|---|---|

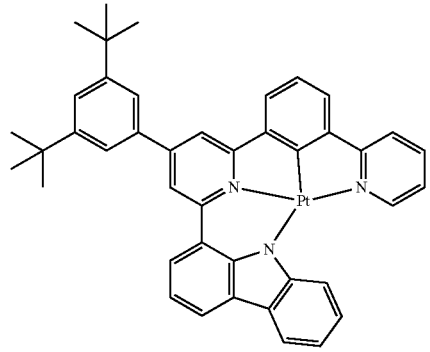

32

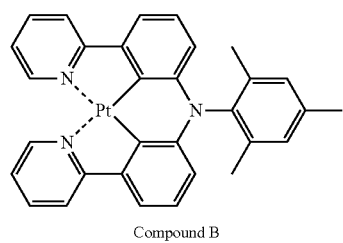

Compound B

Referring to Table 2, it was determined that the organic light-emitting devices of Examples 1 to 4 had excellent driving voltage, efficiency, power, color purity, quantum efficiency, and roll-off ratio characteristics, compared to those of the organic light-emitting device of Comparative Example 1.

Since the organometallic compound has excellent electrical characteristics and thermal stability, an organic light-emitting device including the organometallic compound has excellent driving voltage, efficiency, power, color purity, quantum efficiency, and roll-off ratio characteristics. Also, since the organometallic compound has excellent phosphorescence characteristics, a diagnosis composition having high diagnosis efficiency may be provided by using the organometallic compound.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound represented by Formula 1:

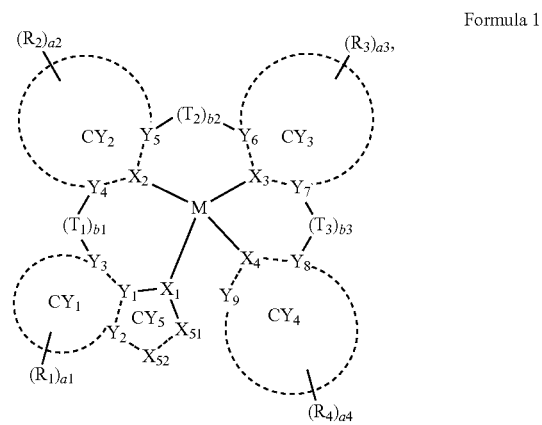

Formula 1 wherein, in Formula 1,

M is beryllium (Be), magnesium (Mg), aluminum (Al), calcium (Ca), titanium (Ti), manganese (Mn), cobalt (Co), copper (Cu), zinc (Zn), gallium (Ga), germanium (Ge), zirconium (Zr), ruthenium (Ru), rhodium (Rh), palladium (Pd), silver (Ag), rhenium (Re), platinum (Pt), or gold (Au), $X_1$ is N and a bond between $X_1$ and M is a covalent bond, $X_2$ to $X_4$ are each independently N or C; at least one of $X_2$ to $X_4$ is C; one bond selected from a bond between $X_2$ and M, a bond between $X_3$ and M, and a bond between $X_4$ and M is a covalent bond; and each of the remaining two bonds is a coordinate bond, $Y_1$ to $Y_9$ are each independently C or N, a bond between $Y_1$ and $Y_2$, a bond between $Y_1$ and $Y_3$, a bond between $X_2$ and $Y_4$, a bond between $X_2$ and $Y_5$, a bond between $X_3$ and $Y_6$, a bond between $X_3$ and $Y_7$, a bond between $X_4$ and $Y_8$, a bond between $X_4$ and $Y_9$, a bond between $Y_2$ and $X_{52}$, and a bond between $X_{51}$ and $X_{52}$ are each independently a single bond or a double bond, $CY_1$ to $CY_5$ are each independently selected from a $C_5$-$C_{30}$ carbocyclic group and a $C_1$-$C_{30}$ heterocyclic group, a cyclometallated ring formed by $CY_5$, $CY_1$, $CY_2$, and M is a 6-membered ring, a 7-membered ring, or an 8-membered ring, $T_1$ to $T_3$ are each independently selected from *—O—*', *—S—*', *—C($R_5$)($R_6$)—*', *—C($R_5$)=*', *=C($R_5$)—*', *—C($R_5$)=C($R_6$)—*', *—C(=O)—*', *—C(=S)—', *—C≡C—*', *—N($R_5$)—*', *—Si($R_5$)($R_6$)—*', and *—P($R_5$)($R_6$)—*', $R_5$ and $R_6$ are optionally linked via a first linking group to form a substituted or unsubstituted $C_5$-$C_{30}$ carbocyclic group or a substituted or unsubstituted $C_1$-$C_{30}$ heterocyclic group, b1 to b3 are each independently 0, 1, 2, or 3, wherein when b1 is zero, *-$(T_1)_{b1}$-*' is a single bond, when b2 is zero, *-$(T_2)_{b2}$-*' is a single bond, and when b3 is zero, *-$(T_3)_{b3}$-*' is a single bond, $X_{51}$ is selected from O, S, N, N($R_{51}$), C($R_{51}$), C($R_{51}$)($R_{52}$), Si($R_{51}$)($R_{52}$), and C(=O), $X_{52}$ is selected from O, S, N, N($R_{53}$), C($R_{53}$), C($R_{53}$)($R_{54}$), Si($R_{53}$)($R_{54}$), and C(=O), $R_{51}$ and $R_{52}$ are optionally linked via a second linking group to form a substituted or unsubstituted $C_5$-$C_{30}$ carbocyclic group or a substituted or unsubstituted $C_1$-$C_{30}$ heterocyclic group, $R_{53}$ and $R_{54}$ are optionally linked via a third linking group to form a substituted or unsubstituted $C_5$-$C_{30}$ carbocyclic group or a substituted or unsubstituted $C_1$-$C_{30}$ heterocyclic group, $R_{51}$ and $R_{53}$ are optionally linked via a fourth linking group to form a substituted or unsubstituted $C_5$-$C_{30}$ carbocyclic group or a substituted or unsubstituted $C_1$-$C_{30}$ heterocyclic group, $R_1$ to $R_6$ and $R_{51}$ to $R_{54}$ are each independently selected from hydrogen, deuterium, —F, —Cl, —Br, —I, —$SF_5$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_6$), —B($Q_6$)($Q_7$), and —P(=O)($Q_8$)($Q_9$), a1 to a4 are each independently 0, 1, 2, 3, 4, or 5, two of groups $R_1$ in the number of a1 are optionally linked to form a substituted or unsubstituted $C_5$-$C_{30}$ carbocyclic group or a substituted or unsubstituted $C_1$-$C_{30}$ heterocyclic group, two of groups $R_2$ in the number of a2 are optionally linked to form a substituted or unsubstituted $C_5$-$C_{30}$ carbocyclic group or a substituted or unsubstituted $C_1$-$C_{30}$ heterocyclic group, two of $R_3$ in the number of a3 are optionally linked to form a substituted or unsubstituted $C_5$-$C_{30}$ carbocyclic group or a substituted or unsubstituted $C_1$-$C_{30}$ heterocyclic group, two of groups $R_4$ in the number of a4 are optionally linked to form a substituted or unsubstituted $C_5$-$C_{30}$ carbocyclic group or a substituted or unsubstituted $C_1$-$C_{30}$ heterocyclic group, two or more neighboring groups selected from $R_1$ to $R_4$ are optionally linked to form a substituted or unsubstituted $C_5$-$C_{30}$ carbocyclic group or a substituted or unsubstituted $C_1$-$C_{30}$ heterocyclic group,

* and *' each indicate a binding site to a neighboring atom, and at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$, wherein $Q_1$ to $Q_9$, $Q_{11}$ to $Q_{19}$, $Q_{21}$ to $Q_{29}$, and $Q_{31}$ to $Q_{39}$ are each independently selected from hydrogen, deuterium, —F, —Cl, —Br, —I, a hydroxyl group, a cyano group, a nitro group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one of a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein $CY_1$ to $CY_4$ are each independently selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an azafluorene group, an azacarbazole group, an azadibenzofuran group, an azadibenzothiophene group, an azadibenzosilole group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an iso-oxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline.

3. The organometallic compound of claim 1, wherein a moiety represented by

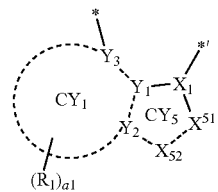

in Formula 1 is a group represented by Formula CY1-1:

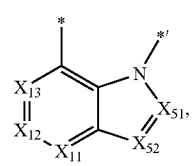

CY1-1 wherein, in Formula CY1-1, $X_{51}$ and $X_{52}$ are the same as described in claim 1, $X_{11}$ is N or $C(R_{11})$, $X_{12}$ is N or $C(R_{12})$, and $X_{13}$ is N or $C(R_{13})$, $R_{11}$ to $R_{13}$ are each independently the same as described in connection with $R_1$ in claim 1, and

* and *' each indicate a binding site to a neighboring atom.

4. The organometallic compound of claim 1, wherein a moiety represented by

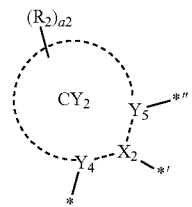

in Formula 1 is selected from groups represented by Formulae CY2-1 to CY2-6:

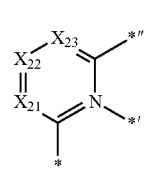

CY2-1

-continued

CY2-2
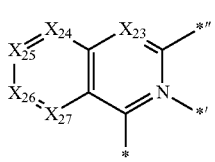

CY2-3
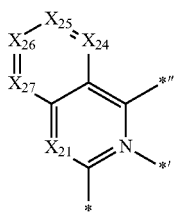

CY2-4
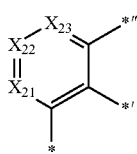

CY2-5
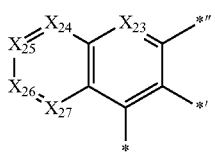

CY2-6
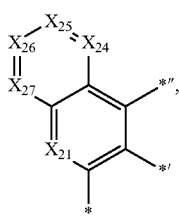

wherein, in Formulae CY2-1 to CY2-4, $X_{21}$ is N or $C(R_{21})$, $X_{22}$ is N or $C(R_{22})$, $X_{23}$ is N or $C(R_{23})$, $X_{24}$ is N or $C(R_{24})$, $X_{25}$ is N or $C(R_{25})$, $X_{26}$ is N or $C(R_{26})$, and $X_{27}$ is N or $C(R_{27})$, $R_{21}$ to $R_{27}$ are each independently the same as described in connection with $R_2$ in claim 1, and \*, \*', and \*" each indicate a binding site to a neighboring atom.

5. The organometallic compound of claim 1, wherein a moiety represented by

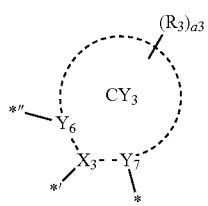

in Formula 1 is selected from groups represented by Formulae CY3-1 to CY3-22:

CY3-1
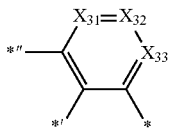

CY3-2
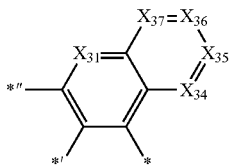

CY3-3
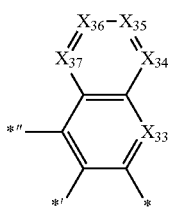

CY3-4
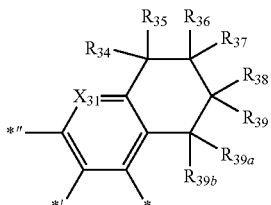

CY3-5
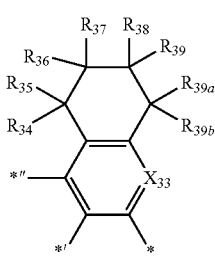

CY3-6
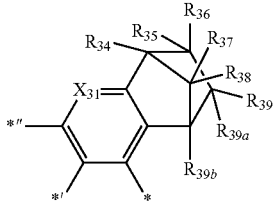

CY3-7
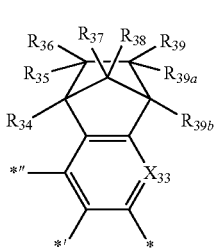

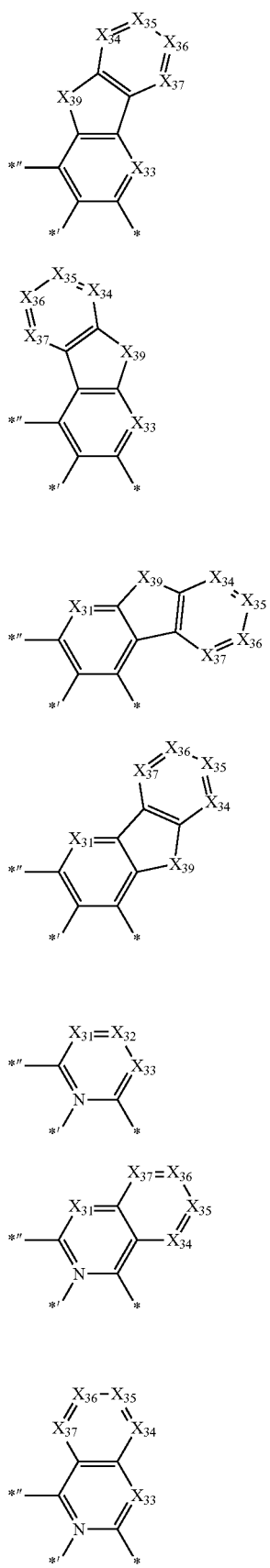
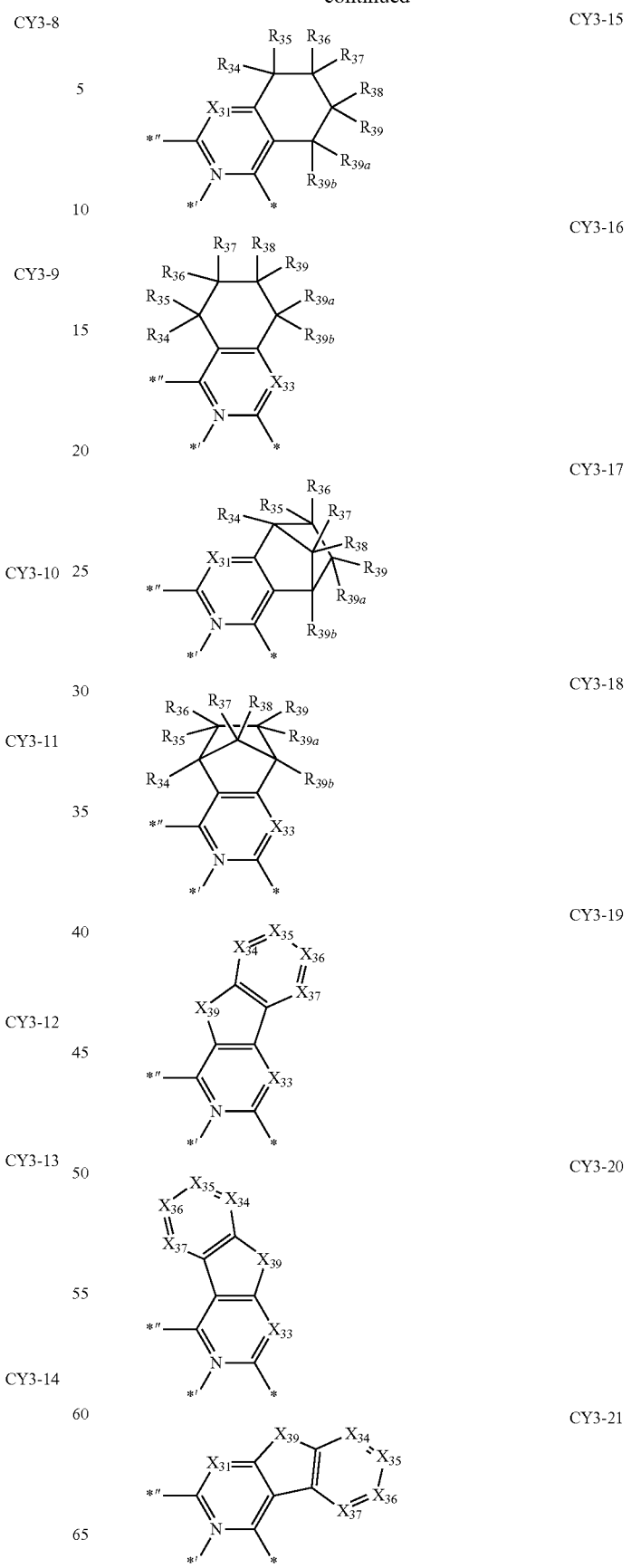

-continued

CY3-22

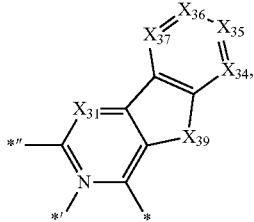

-continued

CY4-4

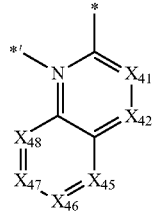

CY4-5

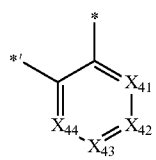

CY4-6

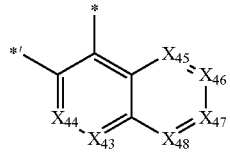

CY4-7

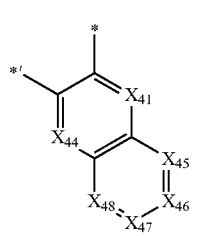

CY4-8

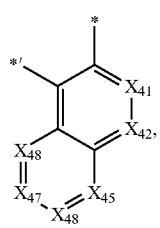

wherein, in Formulae CY3-1 to CY3-22, $X_{31}$ is N or $C(R_{31})$, $X_{32}$ is N or $C(R_{32})$, $X_{33}$ is N or $C(R_{33})$, $X_{34}$ is N or $C(R_{34})$, $X_{35}$ is N or $C(R_{35})$, $X_{36}$ is N or $C(R_{36})$, $X_{37}$ is N or $C(R_{37})$, and $X_{38}$ is N or $C(R_{38})$, $X_{39}$ is $C(R_{39a})(R_{39b})$ $N(R_{39})$, O, S, or $Si(R_{39a})(R_{39b})$, $R_{31}$ to $R_{39}$, $R_{39a}$, and $R_{39b}$ are each independently the same as described in connection with $R_3$ in claim 1, and

*, *', and *" each indicate a binding site to a neighboring atom.

6. The organometallic compound of claim 1, wherein a moiety represented by

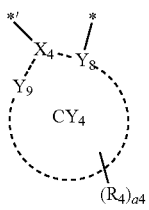

in Formula 1 is selected from groups represented by Formulae CY4-1 to CY4-8:

CY4-1

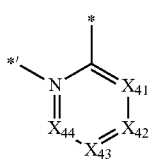

CY4-2

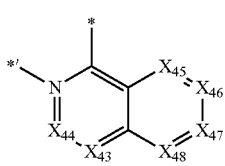

CY4-3

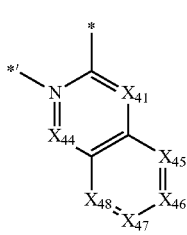

wherein, in Formulae CY4-1 to CY4-8, $X_{41}$ is N or $C(R_{41})$, $X_{42}$ is N or $C(R_{42})$, $X_{43}$ is N or $C(R_{43})$, $X_{44}$ is N or $C(R_{44})$, $X_{45}$ is N or $C(R_{45})$, $X_{46}$ is N or $C(R_{46})$, $X_{47}$ is N or $C(R_{47})$, and $X_{48}$ is N or $C(R_{48})$, $R_{41}$ to $R_{48}$ are each independently the same as described in connection with $R_4$ in claim 1, and

* and *' each indicate a binding site to a neighboring atom.

7. The organometallic compound of claim 1, wherein $T_1$ to $T_3$ are each independently selected from *—O—*', *—S—*', *—C($R_5$)($R_6$)—*', *—N($R_5$)—*', *—Si($R_5$)($R_6$)—*', and *—P($R_5$)($R_6$)—*'.

8. The organometallic compound of claim 1, wherein $T_1$ to $T_3$ are each independently selected from *—C($R_5$)($R_6$)—*', *—Si($R_5$)($R_6$)—*', and *—P($R_5$)($R_6$)—*', $R_5$ and $R_6$ are linked via a first linking group, and the first linking group is selected from a single bond, *—O—*', *—S—*', *—C($R_9$)($R_{10}$)—*', *—C($R_9$)=*', *=C($R_9$)—*', *—C($R_9$)=C($R_{10}$)—*', *—C(=O)—*', *—C(=S)—*', *—C≡C—*', *—N($R_9$)—*', *—Si($R_9$)($R_{10}$)—*', and *—P($R_9$)($R_{10}$)—*', wherein $R_9$ and $R_{10}$ are the same as described in connection with $R_5$ in claim 1, and * and *' each indicate a binding site to a neighboring atom.

9. The organometallic compound of claim 1, wherein
b1 is 1 and b2 and b3 are each zero;
b2 is 1 and b1 and b3 are each zero; or
b3 is 1 and b1 and b2 are each zero.

10. The organometallic compound of claim 1, wherein $R_1$ to $R_6$ and $R_{51}$ to $R_{54}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ are each independently selected from: —CH$_3$, —CD$_3$, —CD$_2$H, —CDH$_2$, —CH$_2$CH$_3$, —CH$_2$CD$_3$, —CH$_2$CD$_2$H, —CH$_2$CDH$_2$, —CHDCH$_3$, —CHDCD$_2$H, —CHDCDH$_2$, —CHDCD$_3$, —CD$_2$CD$_3$, —CD$_2$CD$_2$H, and —CD$_2$CDH$_2$;

an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

11. The organometallic compound of claim 1, wherein $R_1$ to $R_6$ and $R_{51}$ to $R_{54}$ are each independently selected from:

hydrogen, deuterium, —F, a cyano group, a nitro group, —$SF_5$, a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a quinolinyl group, an isoquinolinyl group, a carbazolyl group, a dibenzofuranyl group, and a dibenzothiophenyl group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a quinolinyl group, an isoquinolinyl group, a carbazolyl group, a dibenzofuranyl group, and a dibenzothiophenyl group, each substituted with at least one selected from deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a naphthyl group, a pyridinyl group, a pyrimidinyl group, a carbazolyl group, a dibenzofuranyl group, and a dibenzothiophenyl group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from:
—$CH_3$, —$CD_3$, —$CD_2H$, —$CDH_2$, —$CH_2CH_3$, —$CH_2CD_3$, —$CH_2CD_2H$, —$CH_2CDH_2$, —$CHDCH_3$, —$CHDCD_2H$, —$CHDCDH_2$, —$CHDCD_3$, —$CD_2CD_3$, —$CD_2CD_2H$, and —$CD_2CDH_2$;
an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group; and an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, a phenyl group, and a naphthyl group, each substituted with at least one selected from deuterium, a $C_1$-$C_{10}$ alkyl group, and a phenyl group.

12. The organometallic compound of claim 1, wherein $R_1$ to $R_6$ and $R_{51}$ to $R_{54}$ are each independently selected from hydrogen, deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulae 9-1 to 9-19, groups represented by Formulae 10-1 to 10-48, and —$Si(Q_3)(Q_4)(Q_5)$:

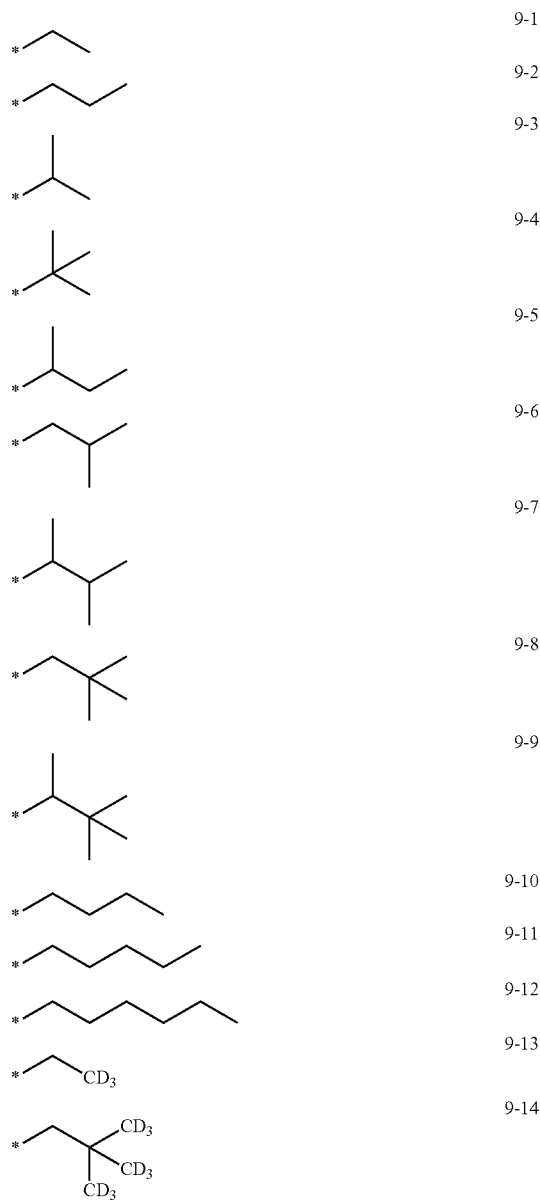

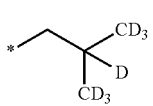
9-15
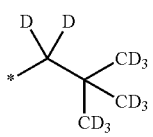
9-16
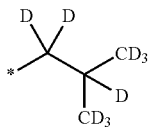
9-17
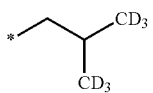
9-18
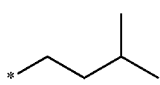
9-19
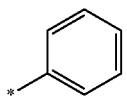
10-1
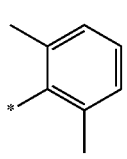
10-2
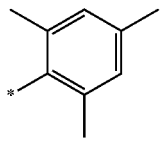
10-3
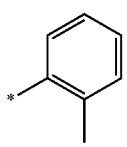
10-4
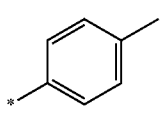
10-5
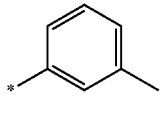
10-6
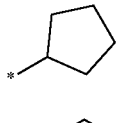
10-7
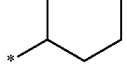
10-8

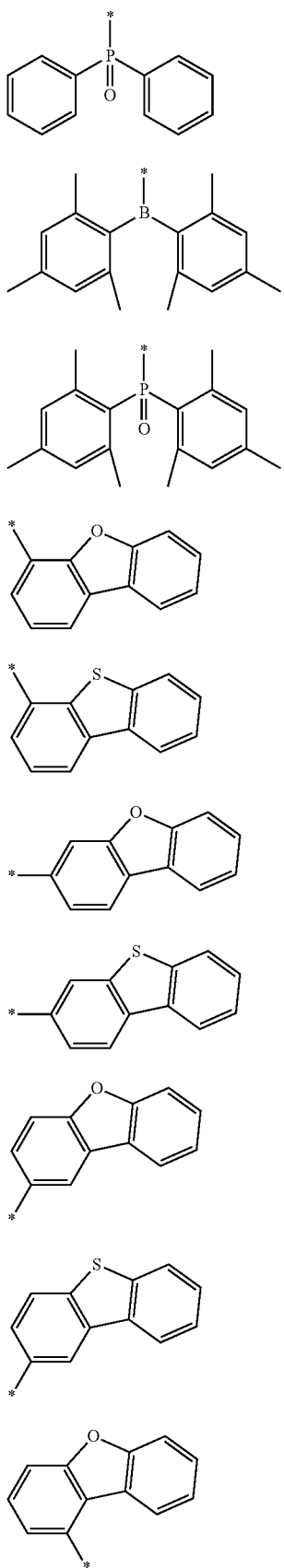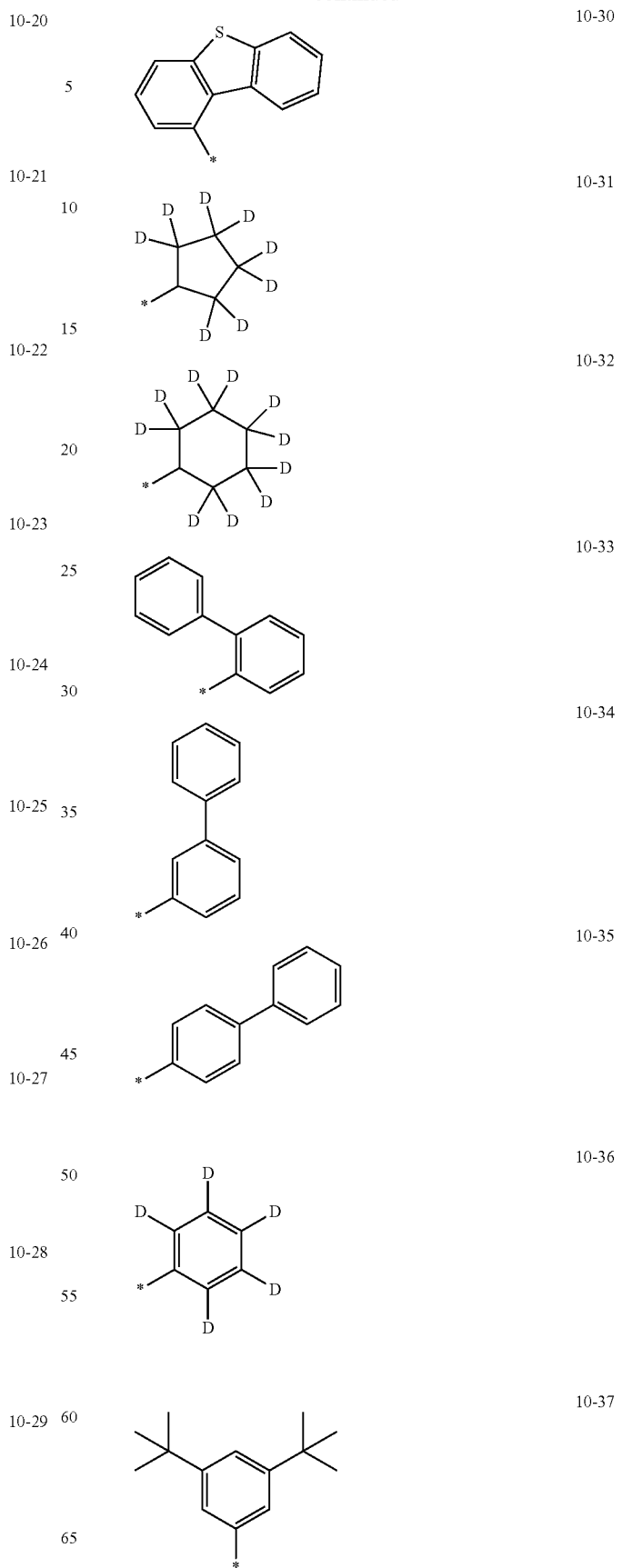

-continued

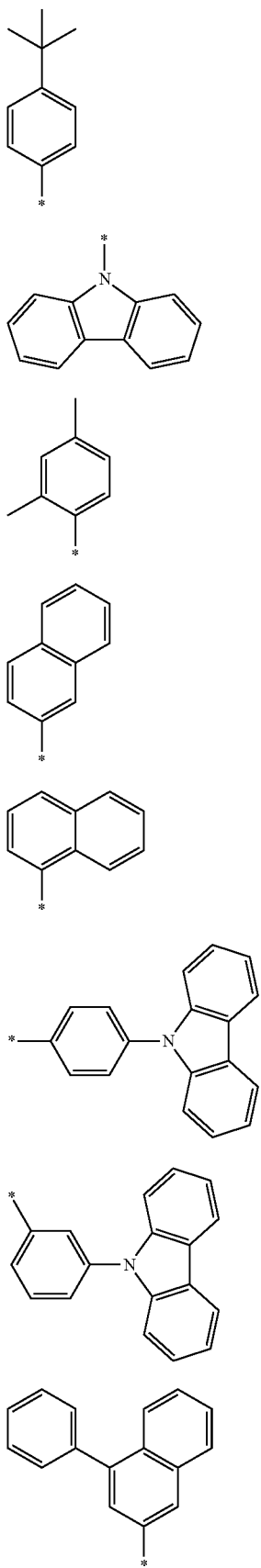

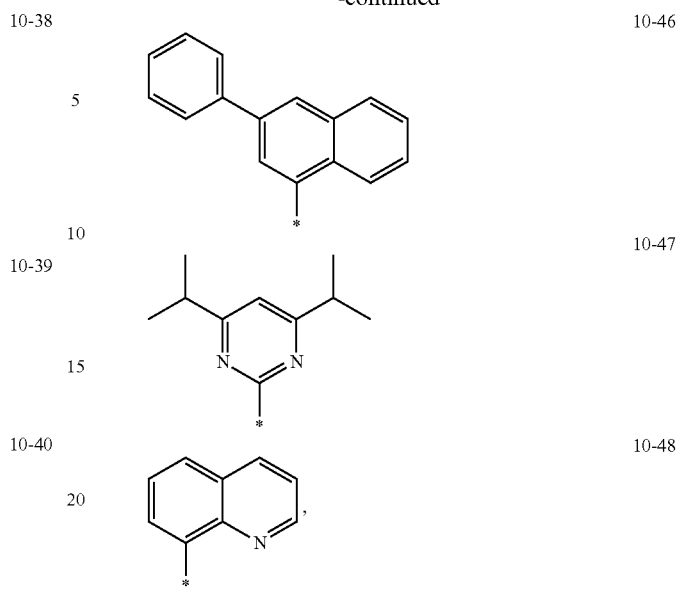

wherein * in Formulae 9-1 to 9-19 and 10-1 to 10-48 indicates a binding site to a neighboring atom.

13. The organometallic compound of claim 1, wherein the organometallic compound is represented by Formula 1-1:

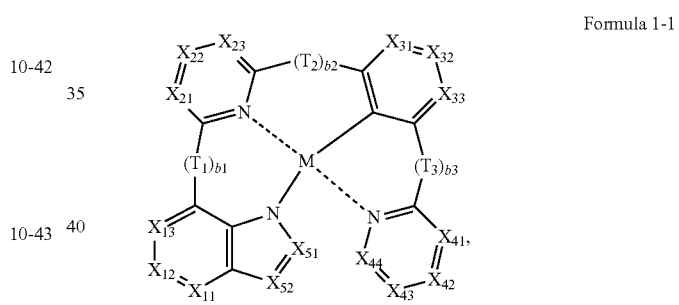

Formula 1-1 wherein, in Formula 1-1,

M, $T_1$ to $T_3$, b1 to b3, $X_{51}$, and $X_{52}$ are the same as described in claim 1, $X_{11}$ is N or $C(R_{11})$, $X_{12}$ is N or $C(R_{12})$, $X_{13}$ is N or $C(R_{13})$, $X_{21}$ is N or $C(R_{21})$, $X_{22}$ is N or $C(R_{22})$, $X_{23}$ is N or $C(R_{23})$, $X_{31}$ is N or $C(R_{31})$, $X_{32}$ is N or $C(R_{32})$, $X_{33}$ is N or $C(R_{33})$, $X_{41}$ is N or $C(R_{41})$, $X_{42}$ is N or $C(R_{42})$, $X_{43}$ is N or $C(R_{43})$, and $X_{44}$ is N or $C(R_{44})$, $R_{11}$ to $R_{13}$ are each independently the same as described in connection with $R_1$ in claim 2, and two of $R_{11}$ to $R_{13}$ are optionally linked to form a substituted or unsubstituted $C_5$-$C_{30}$ carbocyclic group or a substituted or unsubstituted $C_1$-$C_{30}$ heterocyclic group, $R_{21}$ to $R_{23}$ are each independently the same as described in connection with $R_2$ in claim 1, and two of $R_{21}$ to $R_{23}$ are optionally linked to form a substituted or unsubstituted $C_5$-$C_{30}$ carbocyclic group or a substituted or unsubstituted $C_1$-$C_{30}$ heterocyclic group, $R_{31}$ to $R_{33}$ are each independently the same as described in connection with $R_3$ in claim 1, and two of $R_{31}$ to $R_{33}$ are optionally linked to form a substituted or unsubstituted $C_5$-$C_{30}$ carbocyclic group or a substituted or unsubstituted $C_1$-$C_{30}$ heterocyclic group, $R_{41}$ to $R_{44}$ are each independently the same as described in connection with $R_4$ in claim 1, and two of $R_{41}$ to $R_{44}$ are optionally linked to form a substituted or unsubstituted $C_5$-$C_{30}$ carbocyclic group or a substituted or unsubstituted $C_1$-$C_{30}$ heterocyclic group, and two of $R_{11}$ to $R_{13}$, $R_{21}$ to $R_{23}$, $R_{31}$ to $R_{33}$, and $R_{41}$ to $R_{44}$ are optionally linked to form a substituted or unsubstituted $C_5$-$C_{30}$ carbocyclic group or a substituted or unsubstituted $C_1$-$C_{30}$ heterocyclic group.

14. The organometallic compound of claim 1, wherein the organometallic compound is represented by Formula 1-1A:

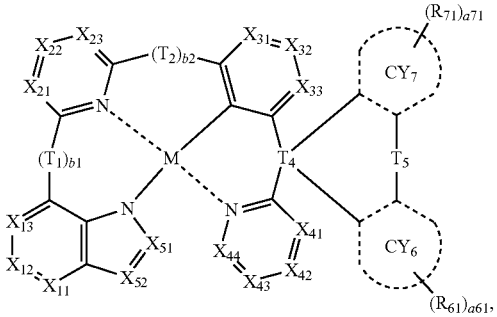

Formula 1-1A wherein, in Formula 1-1A,

M, $T_1$, $T_2$, b1, b2, $X_{51}$, and $X_{52}$ are the same as described in claim 1, $X_{11}$ is N or C($R_{11}$), $X_{12}$ is N or C($R_{12}$), $X_{13}$ is N or C($R_{13}$), $X_{21}$ is N or C($R_{21}$), $X_{22}$ is N or C($R_{22}$), $X_{23}$ is N or C($R_{23}$), $X_{31}$ is N or C($R_{31}$), $X_{32}$ is N or C($R_{32}$), $X_{33}$ is N or C($R_{33}$), $X_{41}$ is N or C($R_{41}$), $X_{42}$ is N or C($R_{42}$), $X_{43}$ is N or C($R_{43}$), and $X_{44}$ is N or C($R_{44}$), $R_{11}$ to $R_{13}$ are each independently the same as described in connection with $R_1$ in claim 1, and two of $R_{11}$ to $R_{13}$ are optionally linked to form a substituted or unsubstituted $C_5$-$C_{30}$ carbocyclic group or a substituted or unsubstituted $C_1$-$C_{30}$ heterocyclic group, $R_{21}$ to $R_{23}$ are each independently the same as described in connection with $R_2$ in claim 1, and two of $R_{21}$ to $R_{23}$ are optionally linked to form a substituted or unsubstituted $C_5$-$C_{30}$ carbocyclic group or a substituted or unsubstituted $C_1$-$C_{30}$ heterocyclic group, $R_{31}$ to $R_{33}$ are each independently the same as described in connection with $R_3$ in claim 1, and two of $R_{31}$ to $R_{33}$ are optionally linked to form a substituted or unsubstituted $C_5$-$C_{30}$ carbocyclic group or a substituted or unsubstituted $C_1$-$C_{30}$ heterocyclic group, $R_{41}$ to $R_{44}$ are each independently the same as described in connection with $R_4$ in claim 1, and two of $R_{41}$ to $R_{44}$ are optionally linked to form a substituted or unsubstituted $C_5$-$C_{30}$ carbocyclic group or a substituted or unsubstituted $C_1$-$C_{30}$ heterocyclic group, two of $R_{11}$ to $R_{13}$, $R_{21}$ to $R_{23}$, $R_{31}$ to $R_{33}$, and $R_{41}$ to $R_{44}$ are optionally linked to form a substituted or unsubstituted $C_6$-$C_{30}$ carbocyclic group or a substituted or unsubstituted $C_1$-$C_{30}$ heterocyclic group, $R_{61}$ and $R_{71}$ are each independently the same as described in connection with $R_1$ in claim 1, a61 and a71 are each independently 0, 1, 2, or 3, $T_4$ is C or Si, $T_5$ is selected from a single bond, *—O—*', *—S—*', *—C($R_7$)($R_8$)—*', *—C($R_7$)=*', *=C($R_8$)—*', *—C($R_7$)=C($R_8$)—*', *—C(=O)—*', *—C(=S)—*', *—C≡C—*', *—N($R_7$)—*, *—Si($R_7$)($R_8$)—*', and *—P($R_7$)($R_8$)—*', $R_7$ and $R_8$ are each independently the same as described in connection with $R_5$ in claim 1, and

* and *' each indicate a binding site to a neighboring atom.

15. The organometallic compound of claim 1, wherein the organometallic compound is one of Compounds 1 to 132:

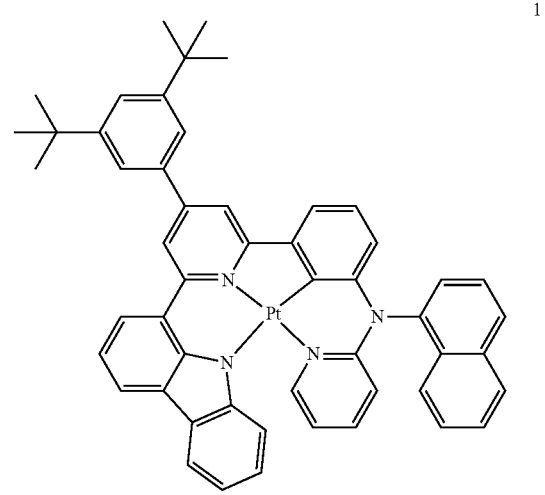

1

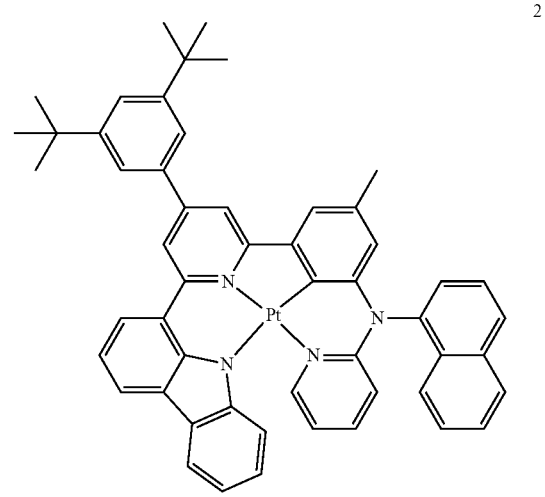

2

3
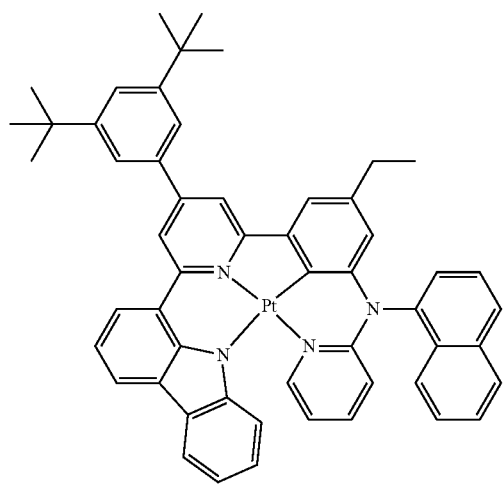
4
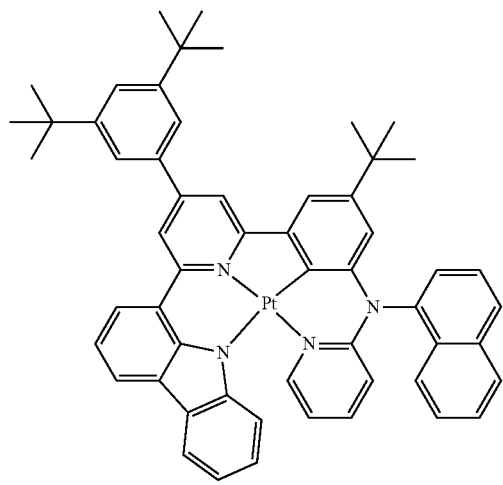
5
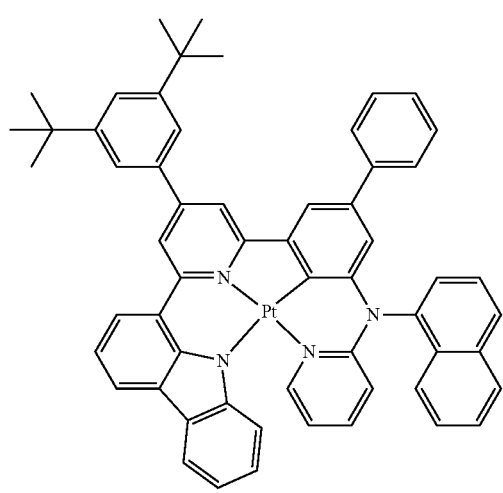
6
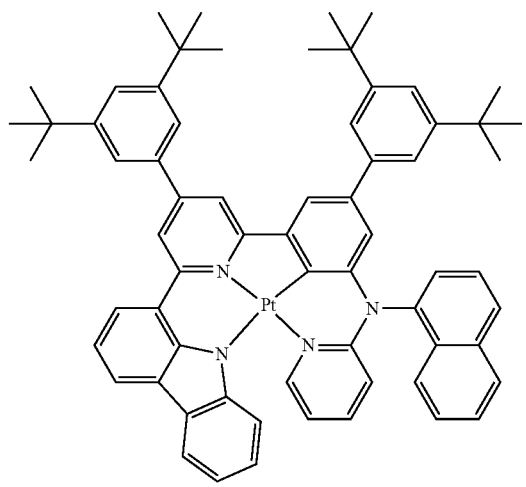
7
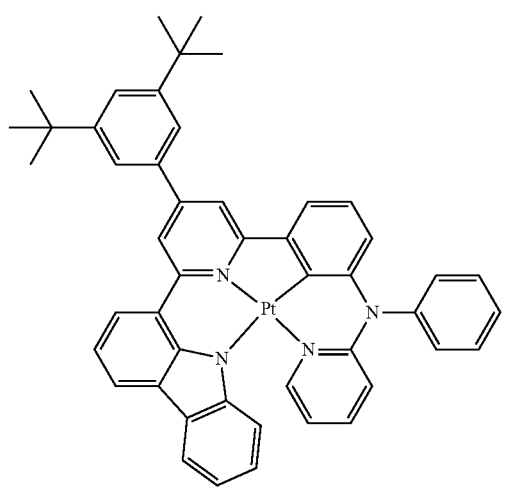
8
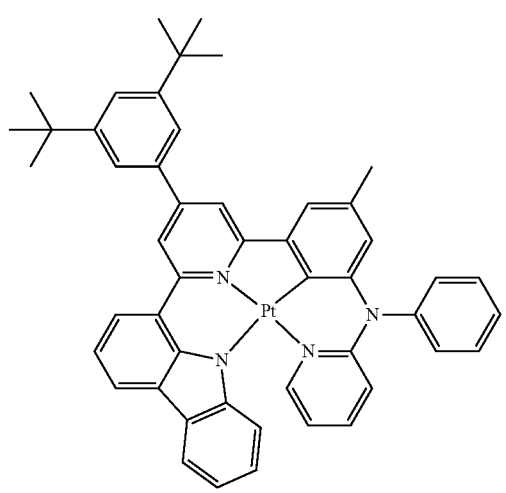

9
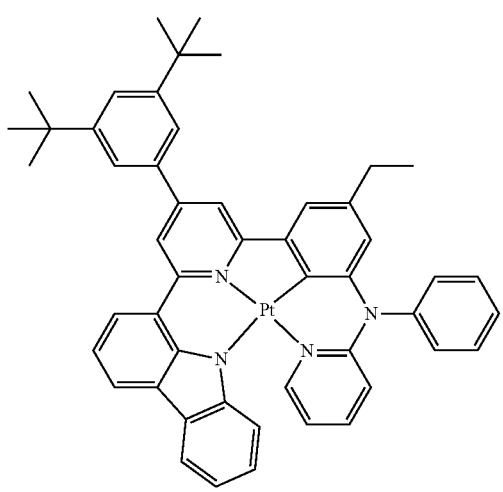
10
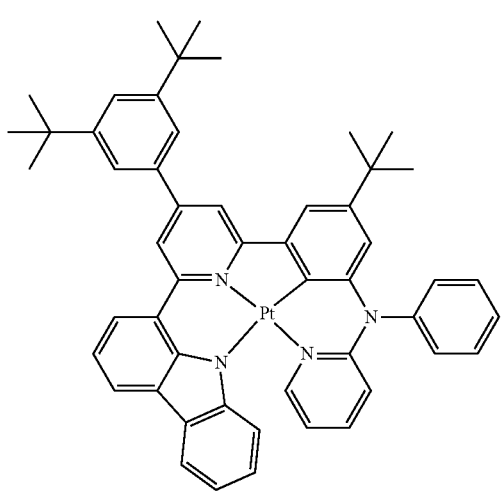
11
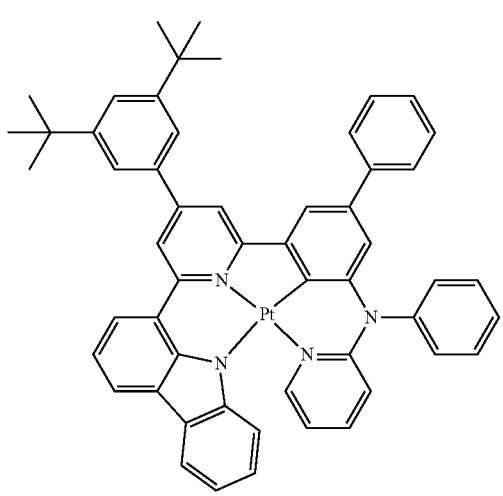
12
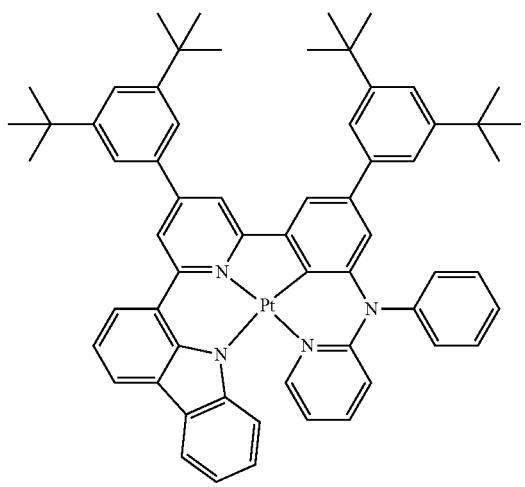
13
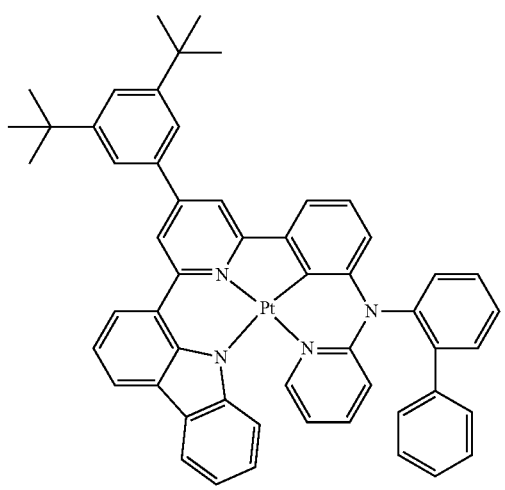
14
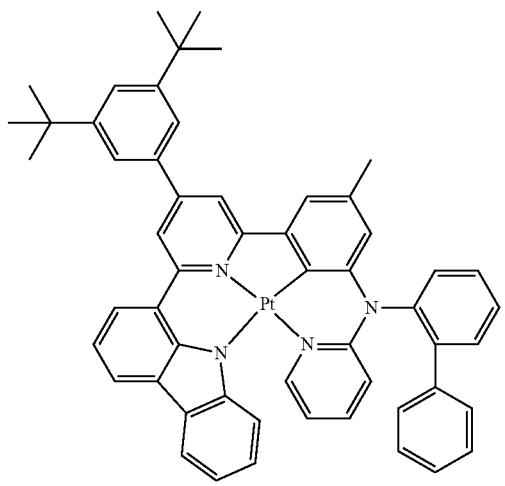

15
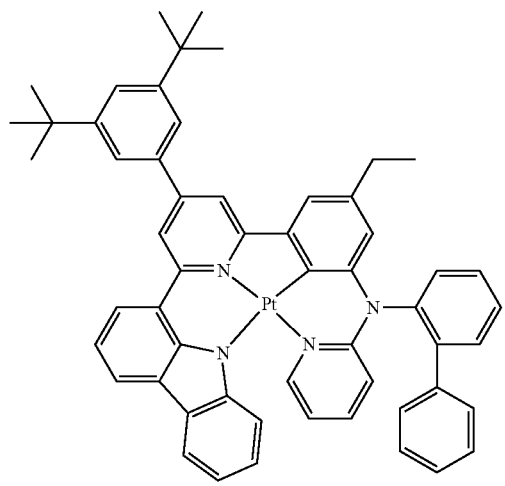
16
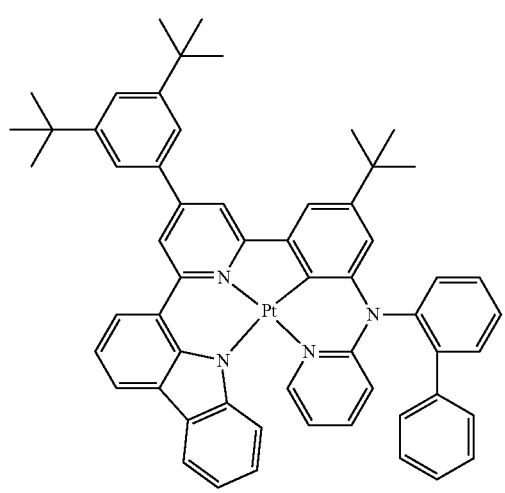
17
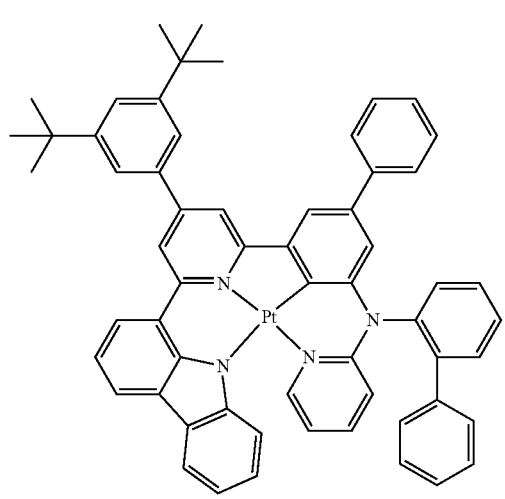
18
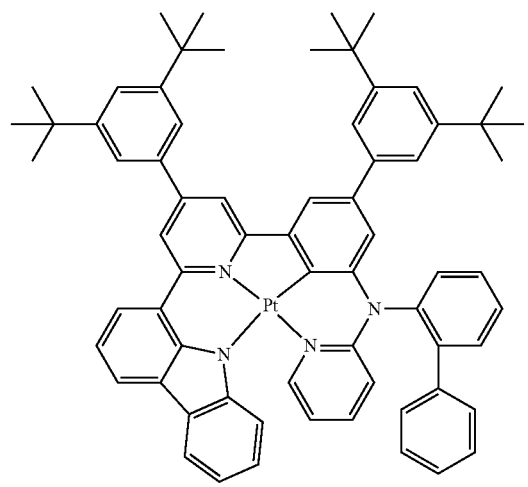
19
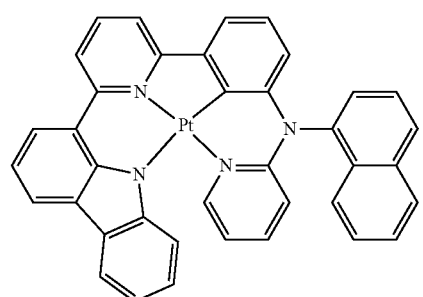
20
21
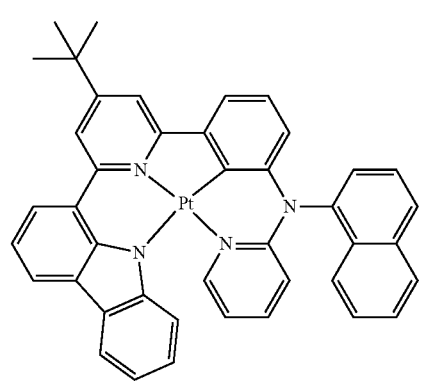

22
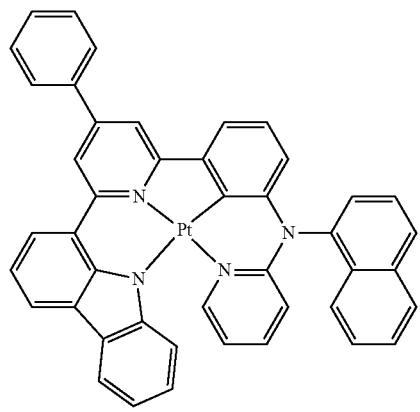
23
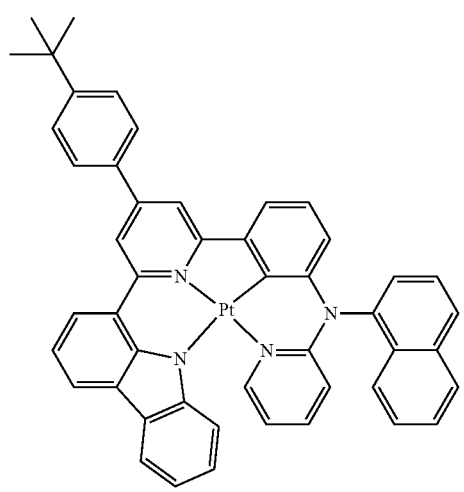
24
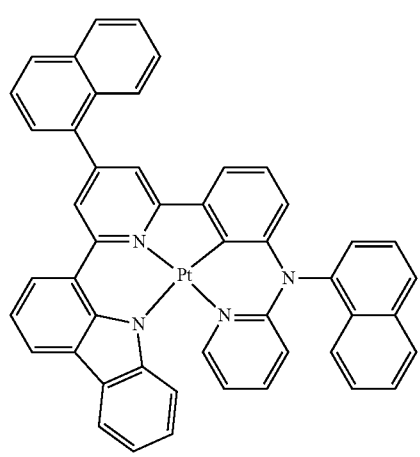
25
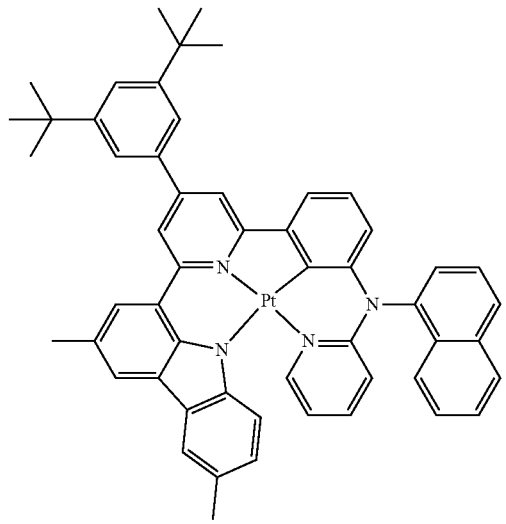
26
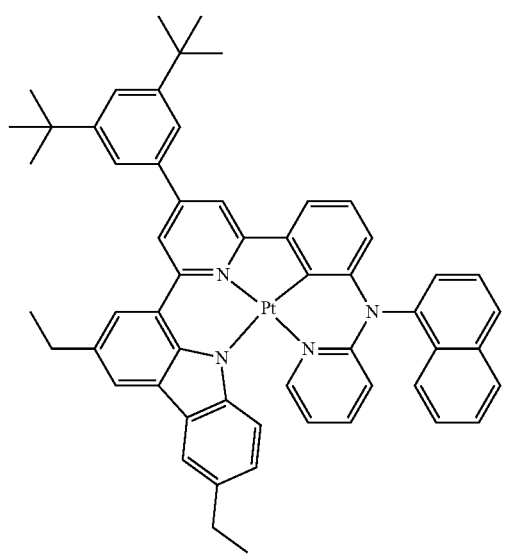

27
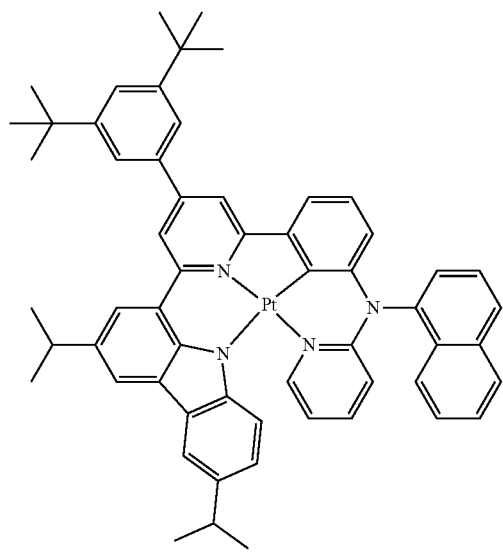
28
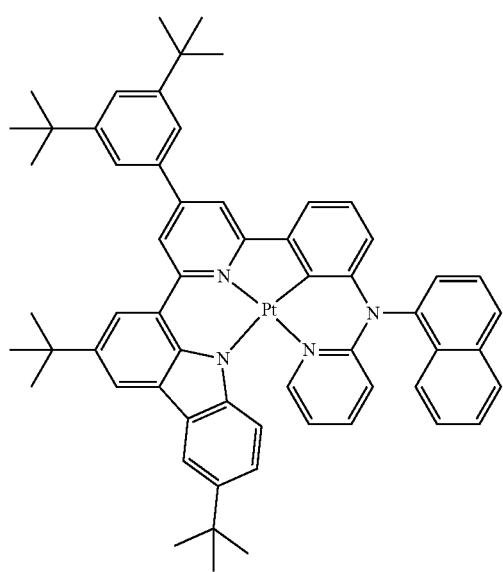
29
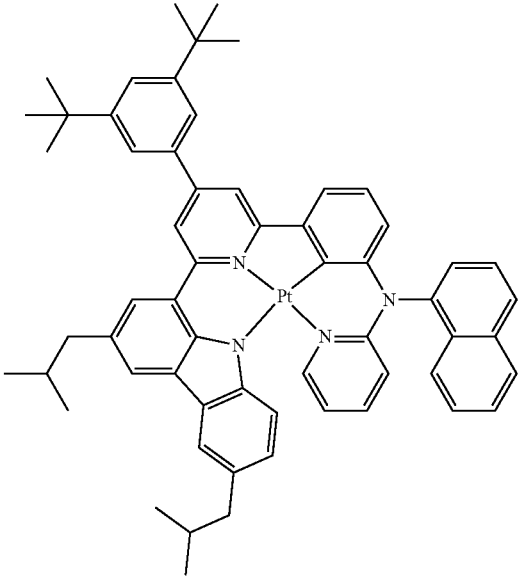
30
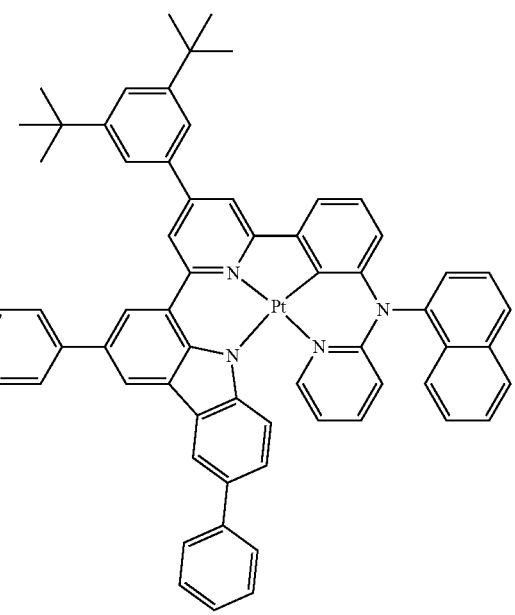

31
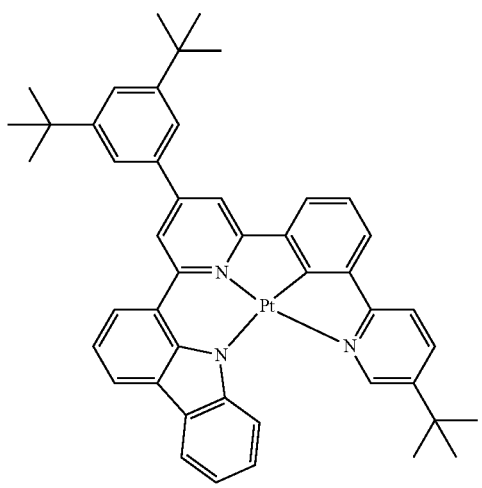
34
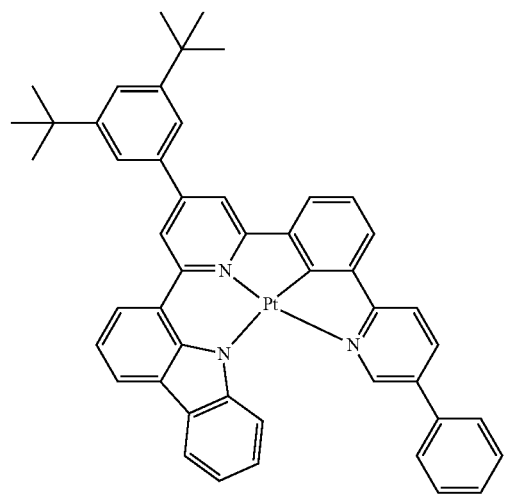
32
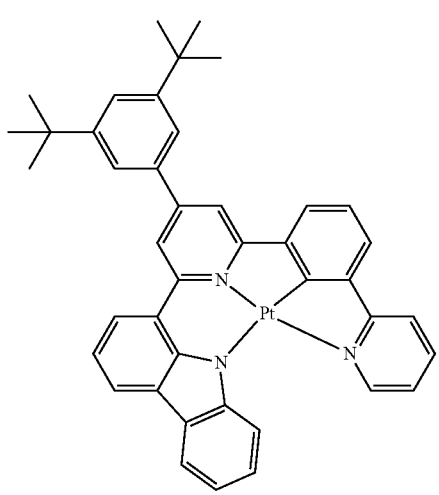
35
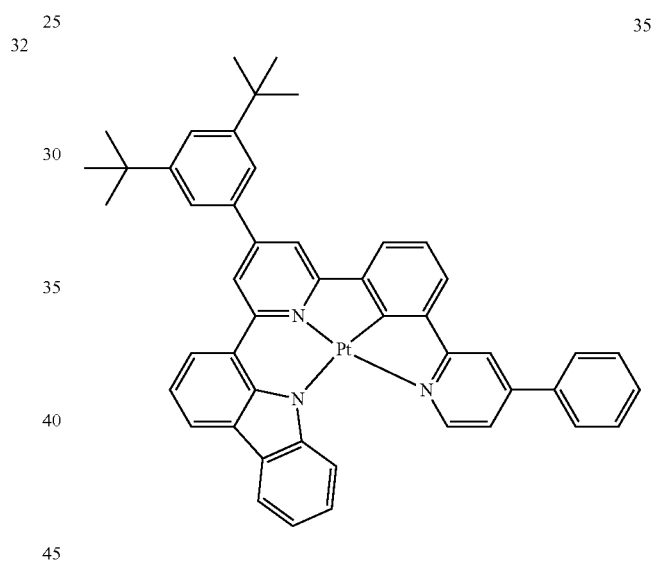
33
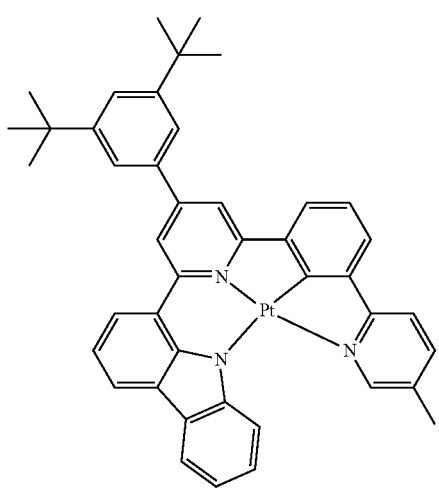
36
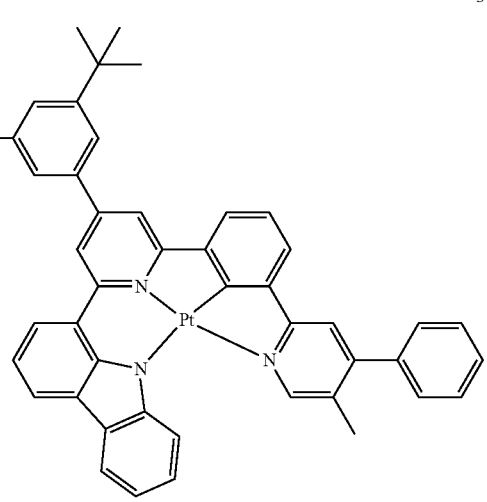

169
-continued
170
-continued
37
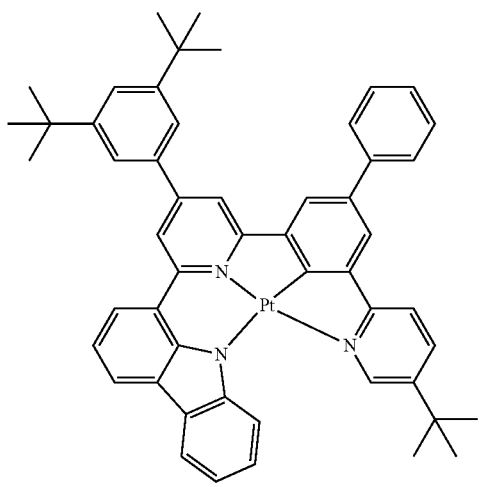
40
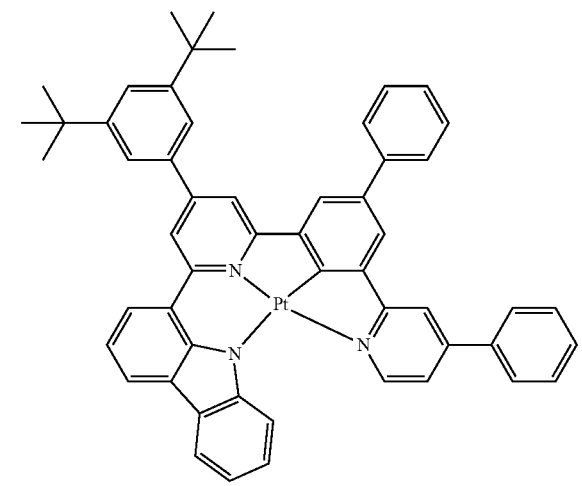
38
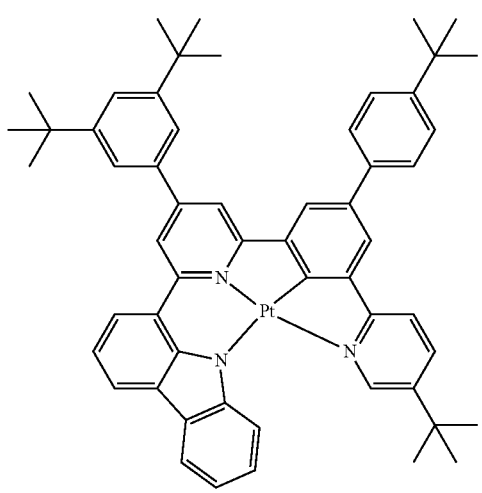
41
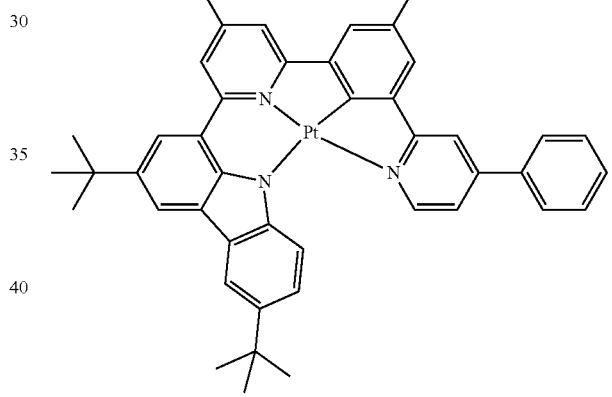
39
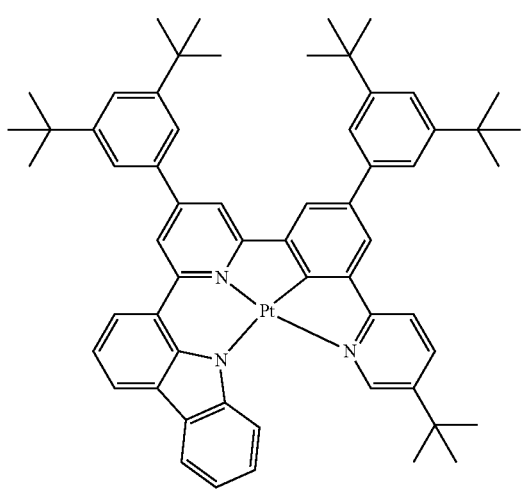
42
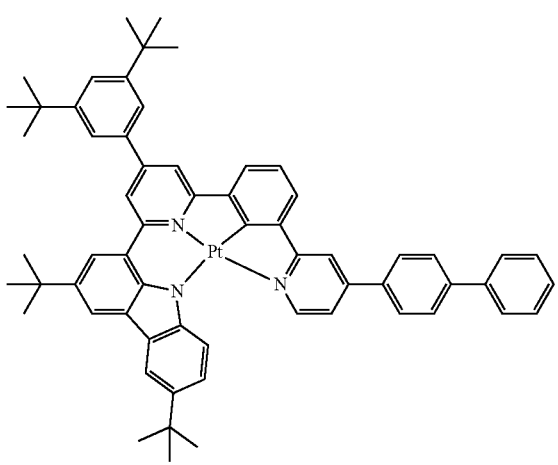

43
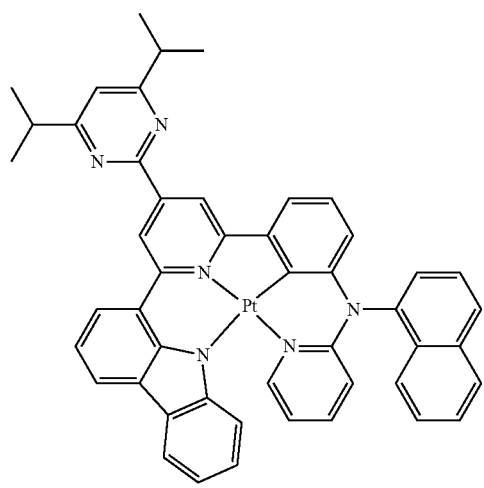
46
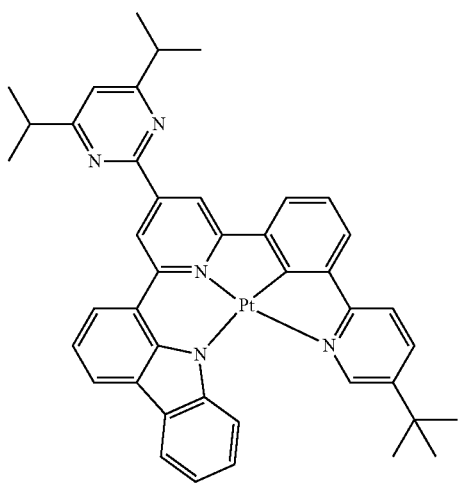
44
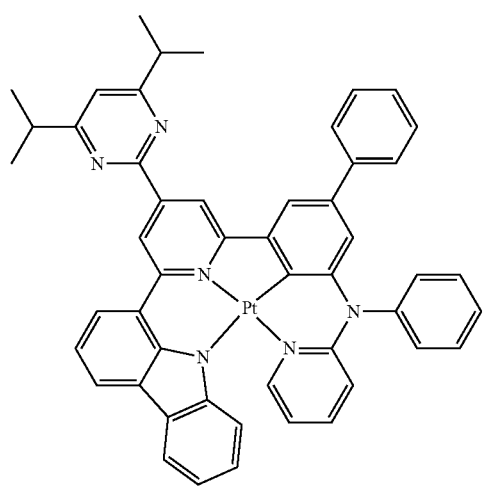
47
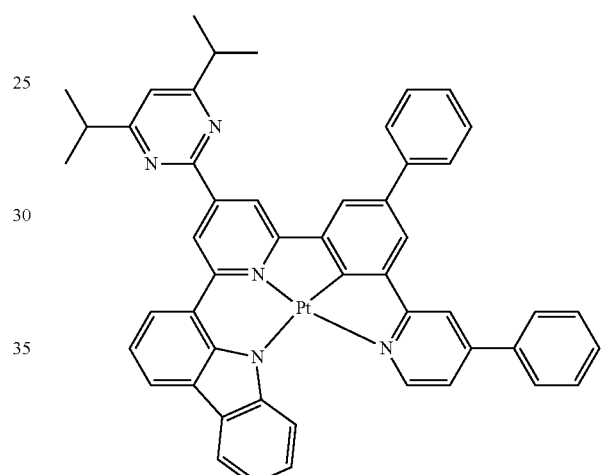
45
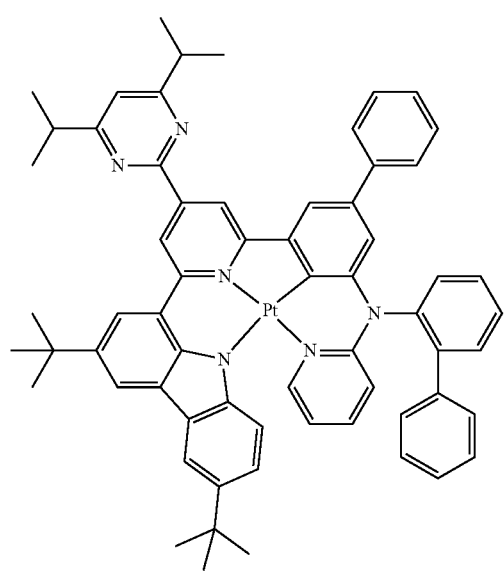
48
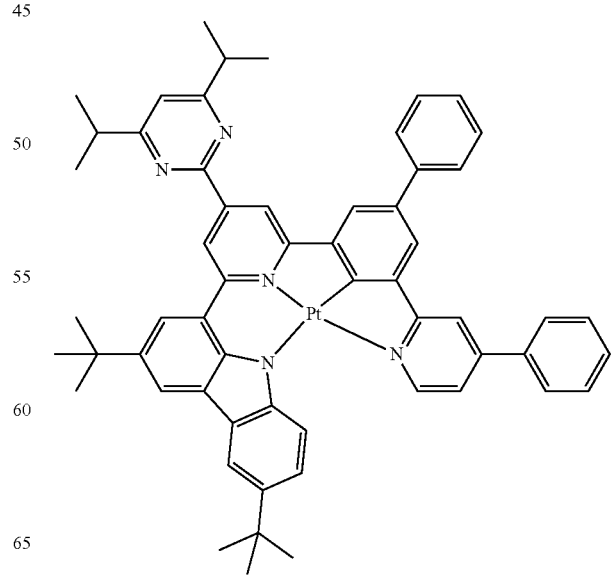

49
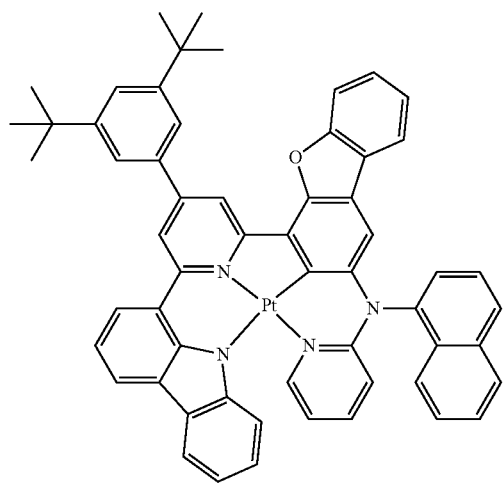
50
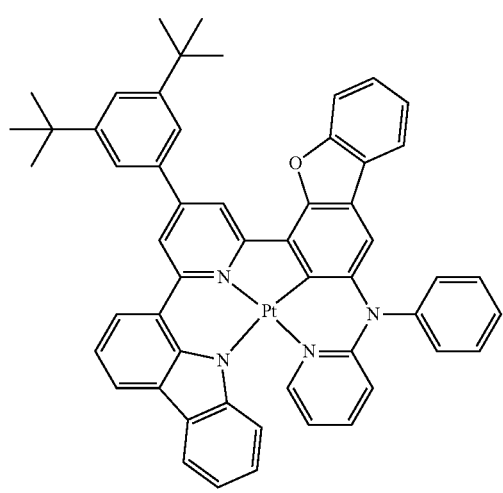
51
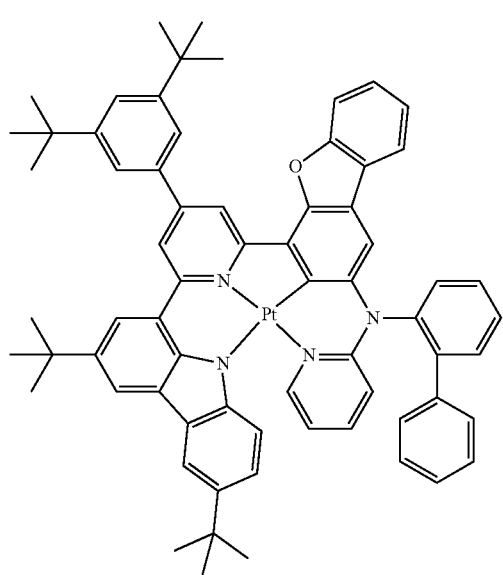
52
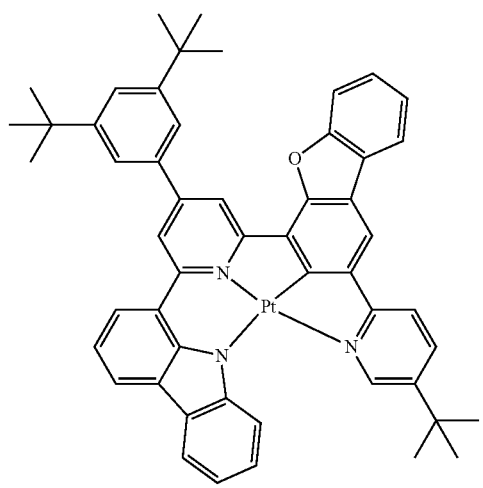
53
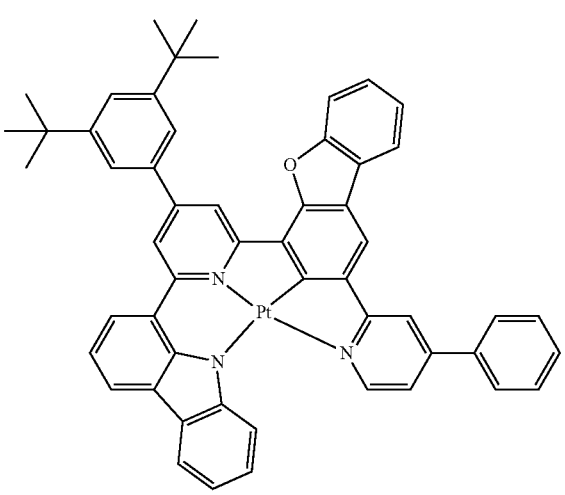
54
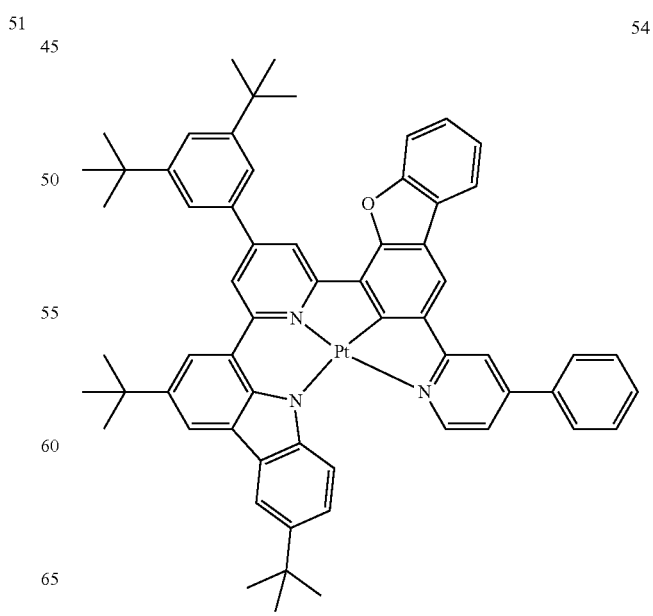

55
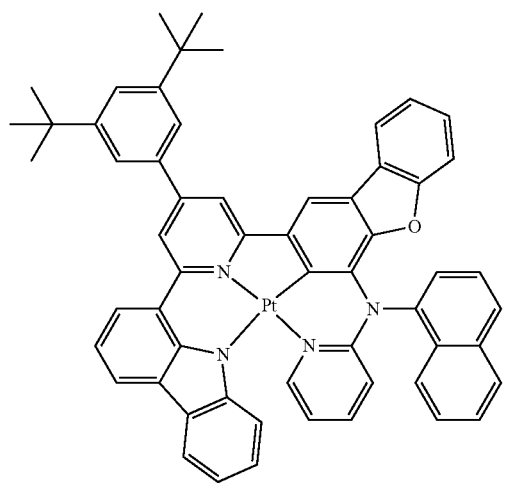
56
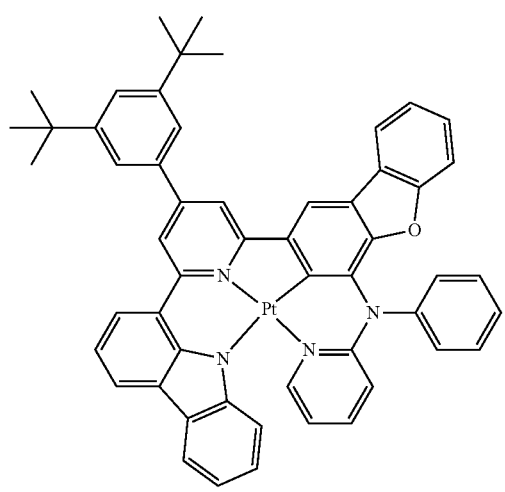
57
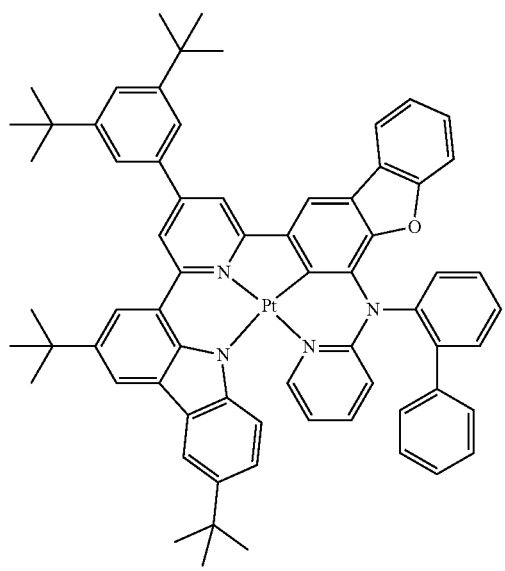
58
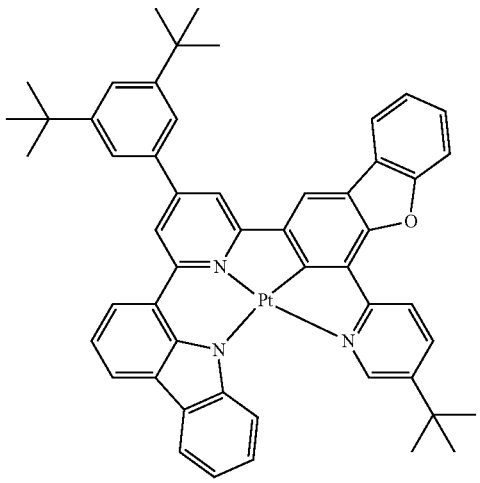
59
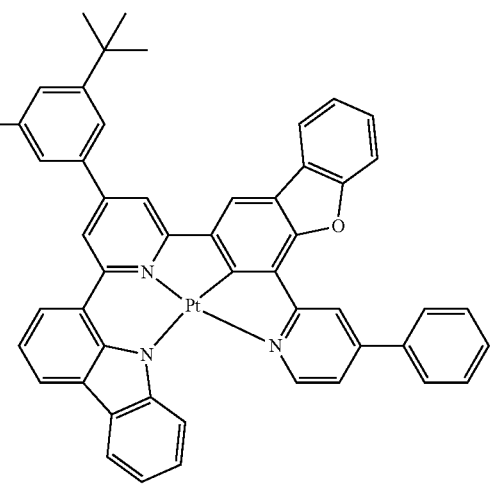
60
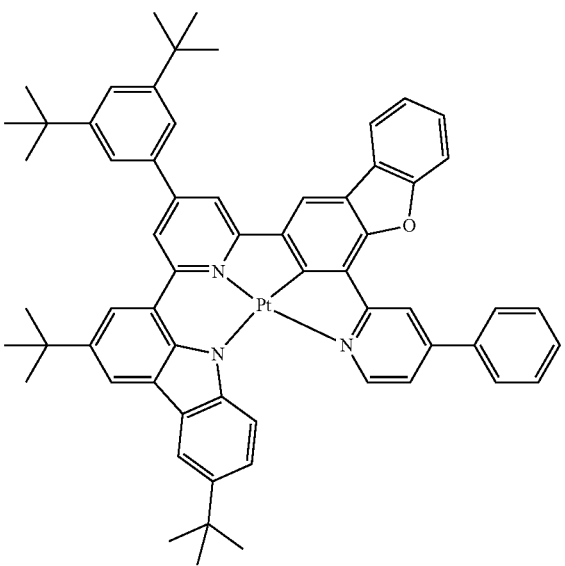

177
-continued
61
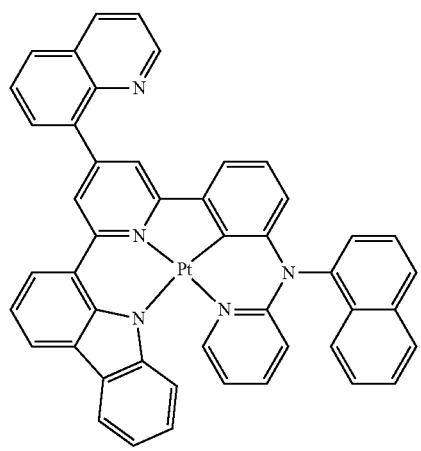
62
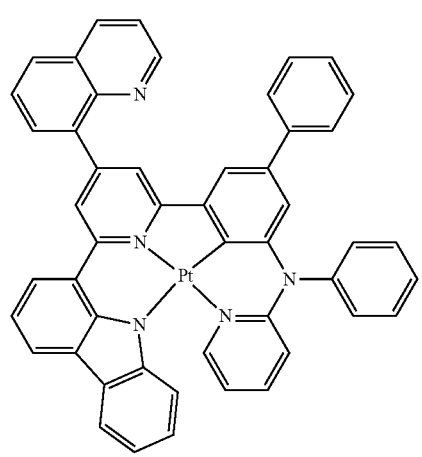
63
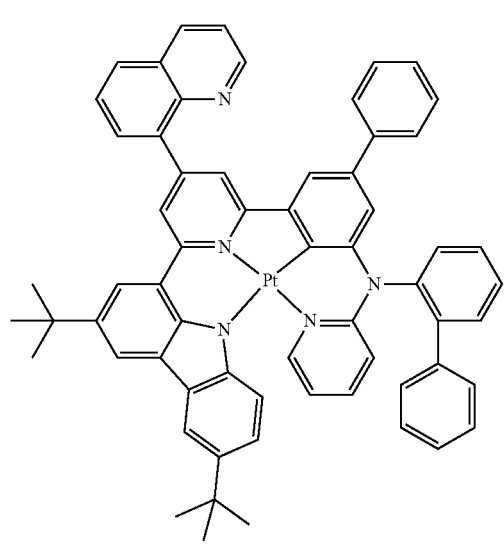
178
-continued
64
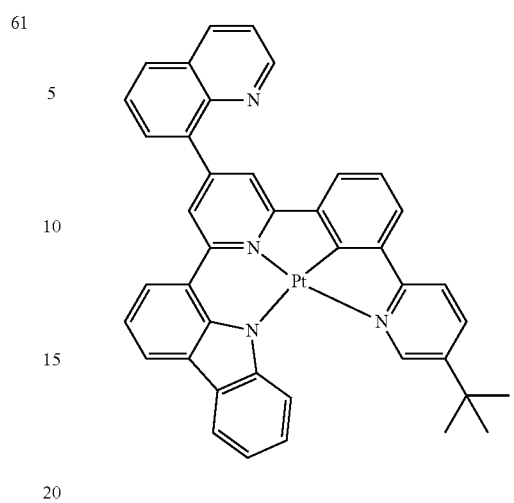
65
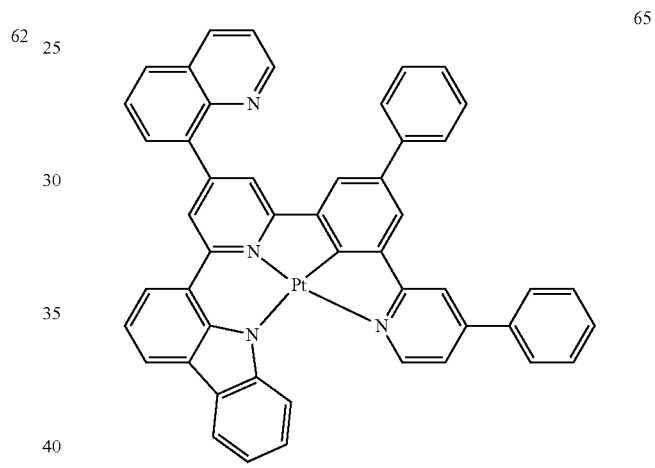
66
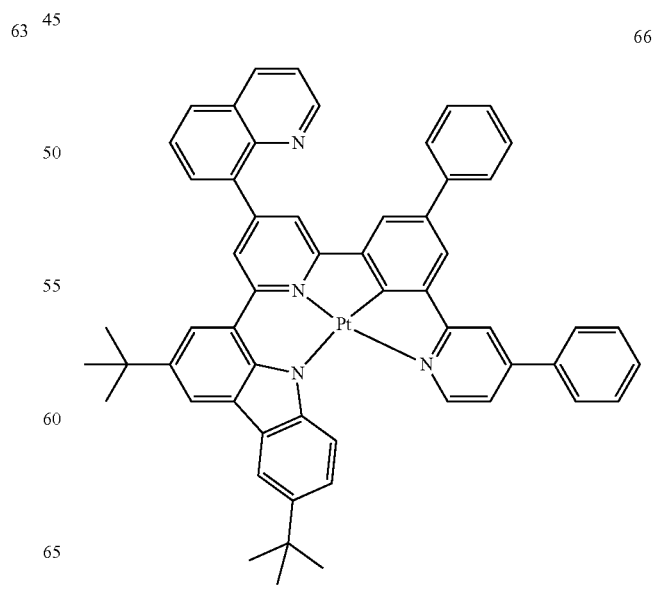

-continued
67
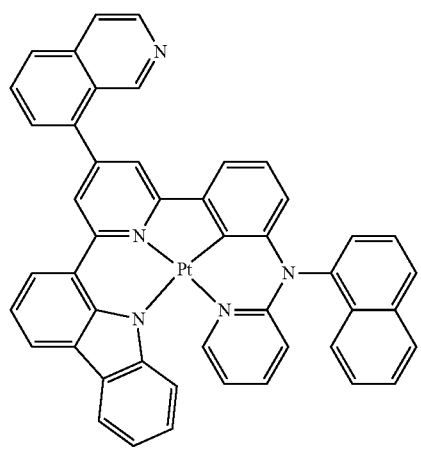
68
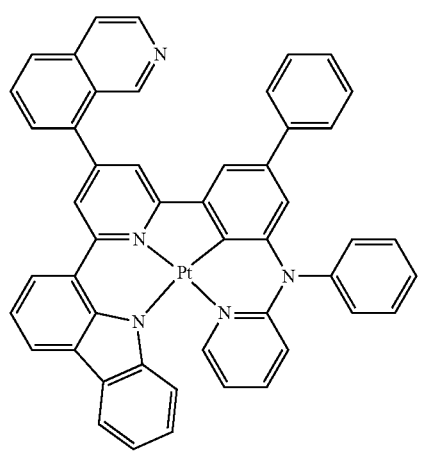
69
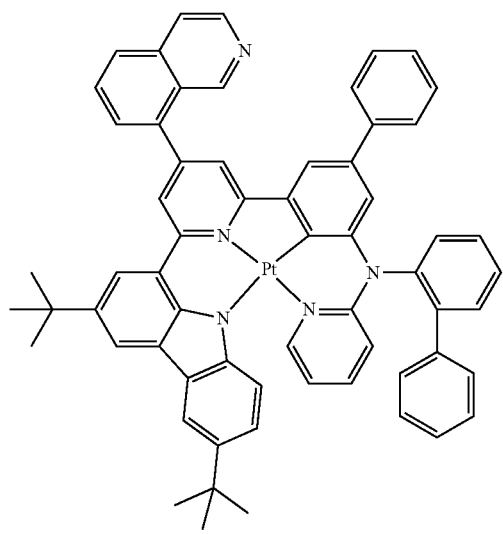
-continued
70
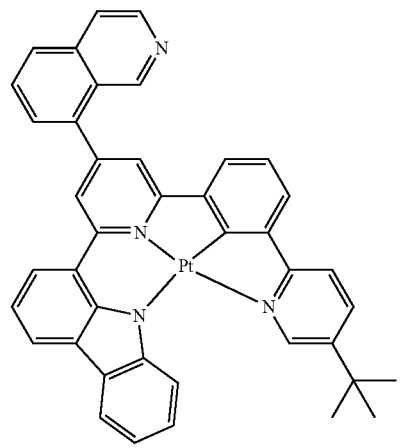
71
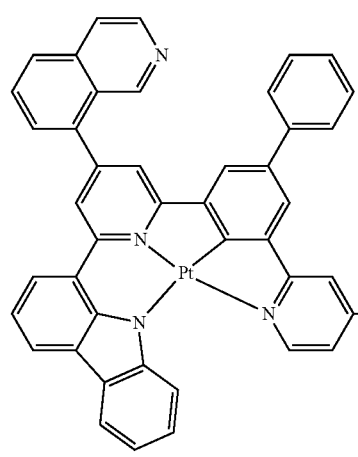
72
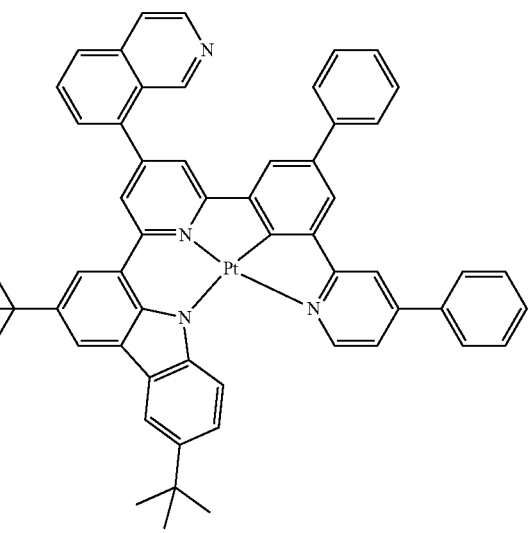

-continued
73
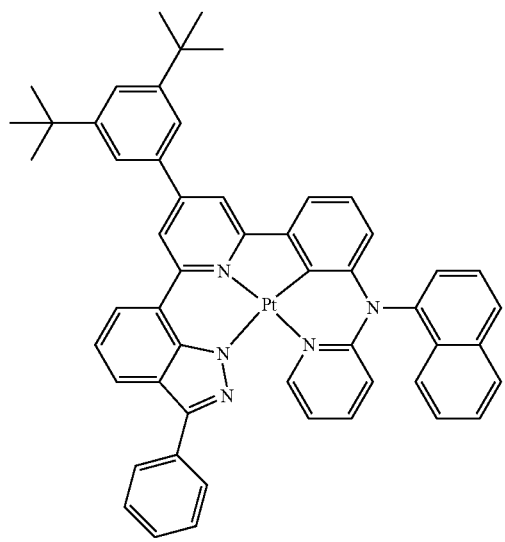
74
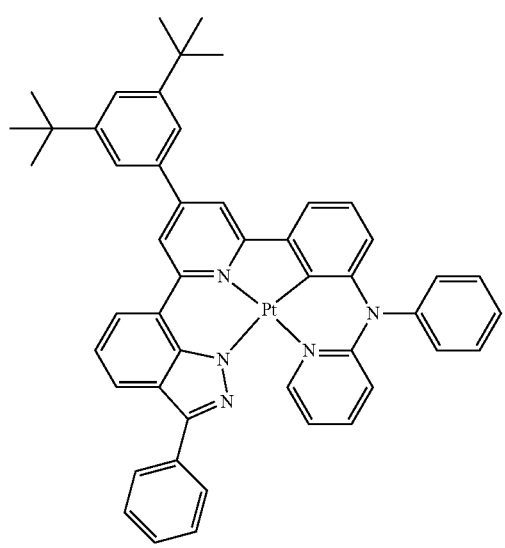
75
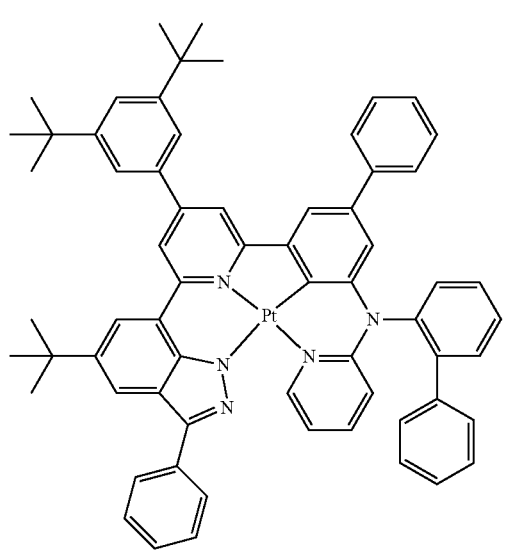
76
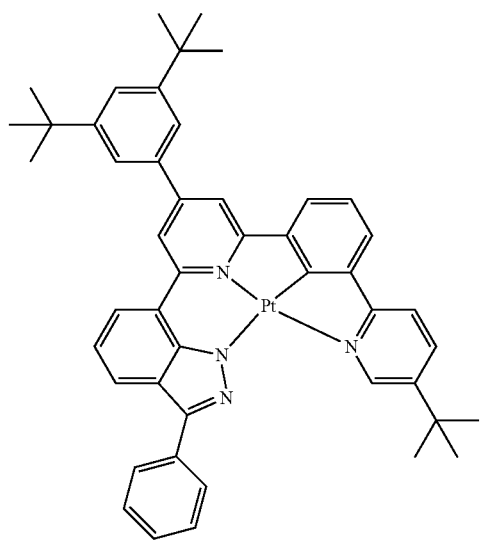
77
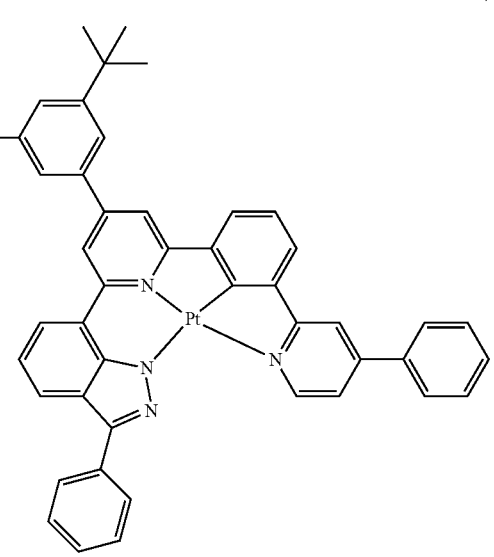
78
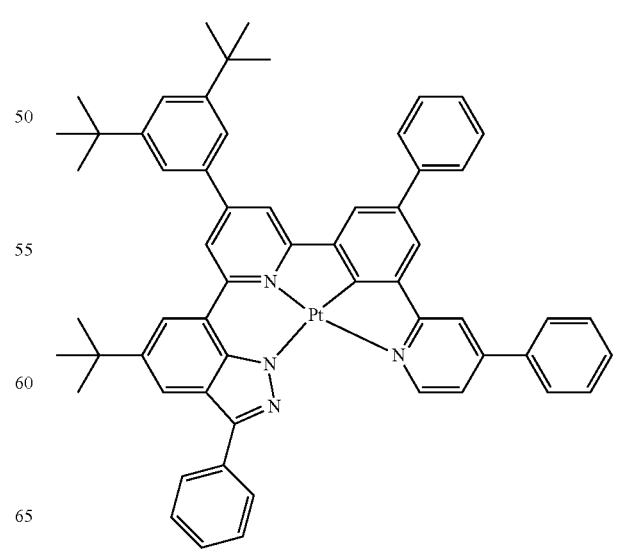

79
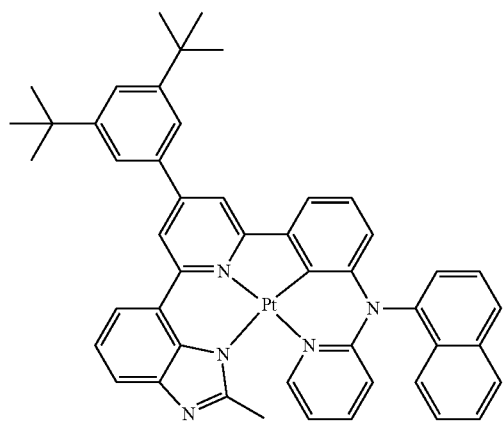
82
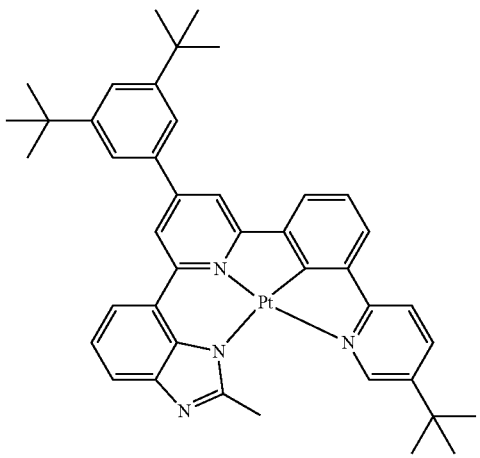
80
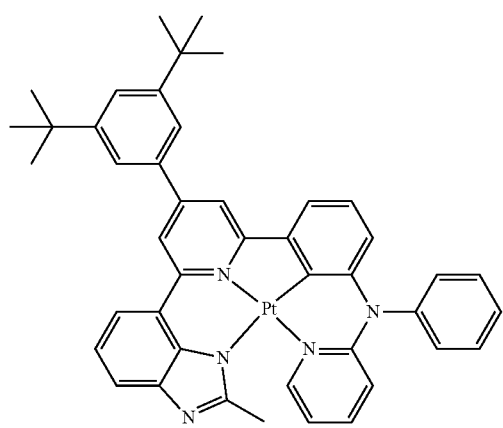
83
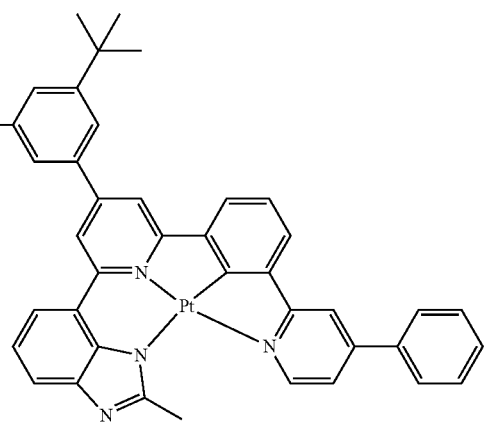
81
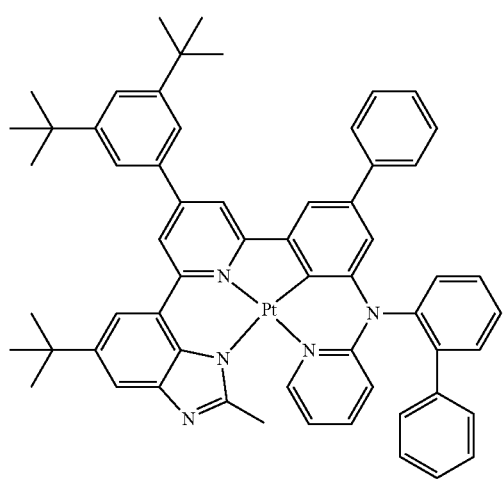
84
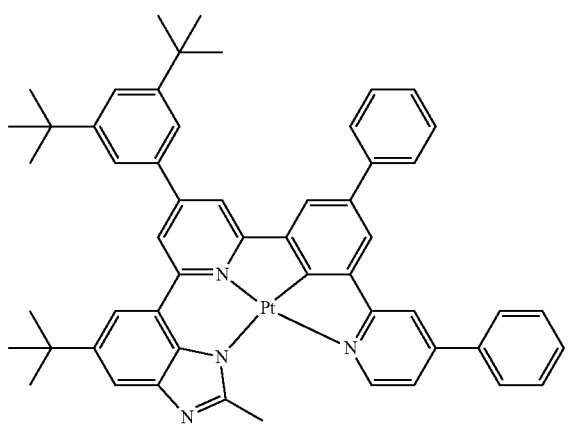

185
85
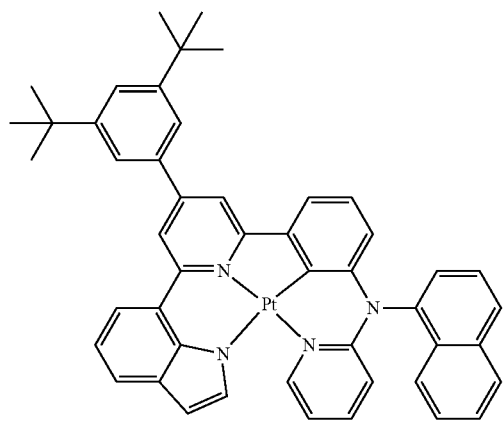
86
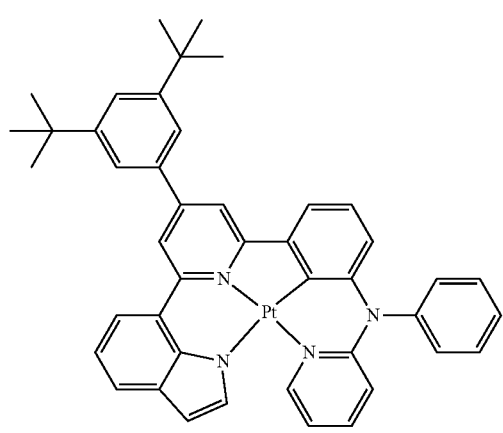
87
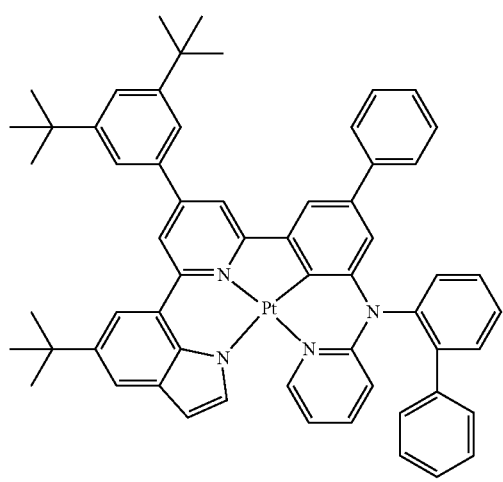
186
88
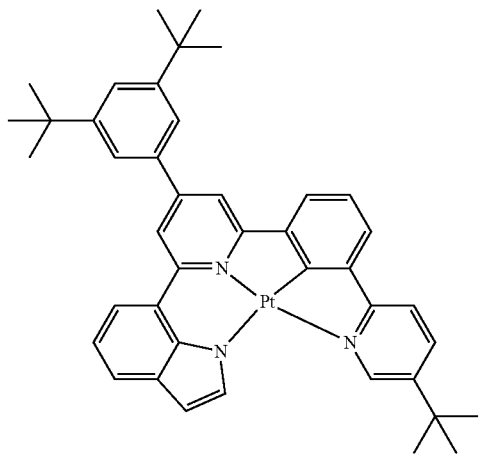
89
90

91
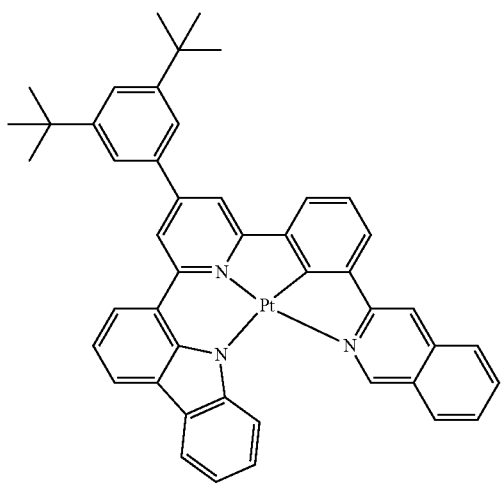
92
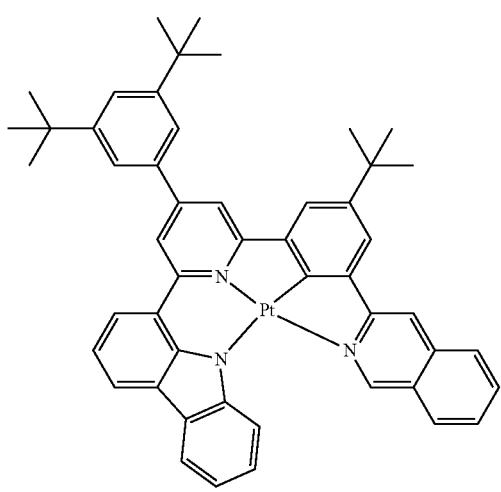
93
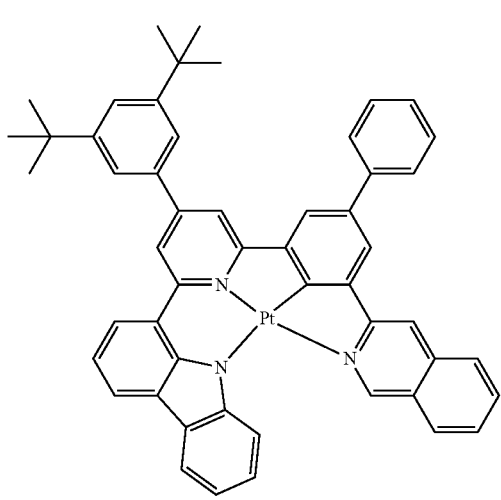
94
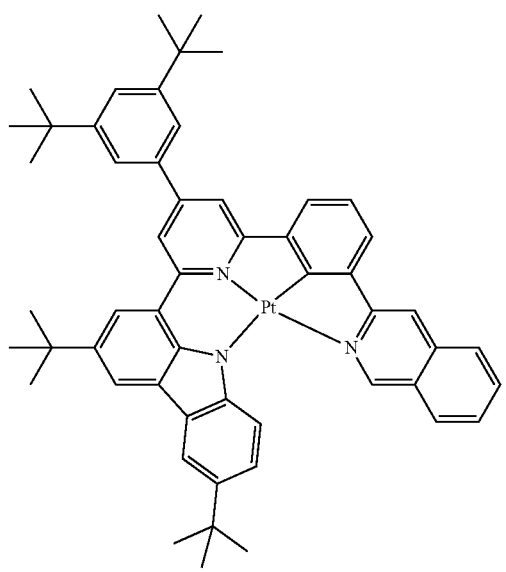
95
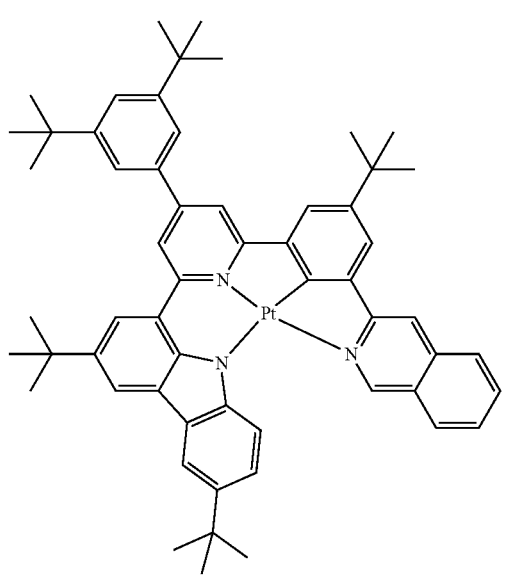

-continued
96
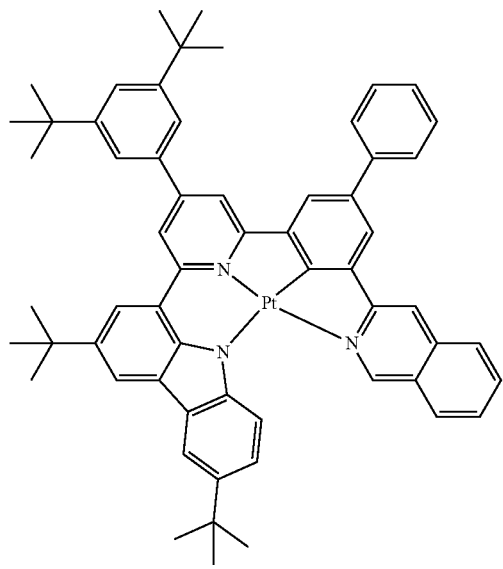
97
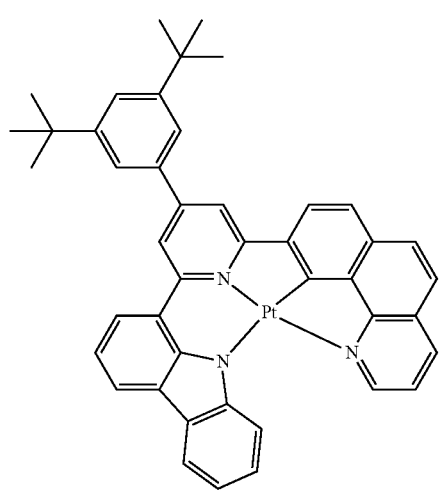
98
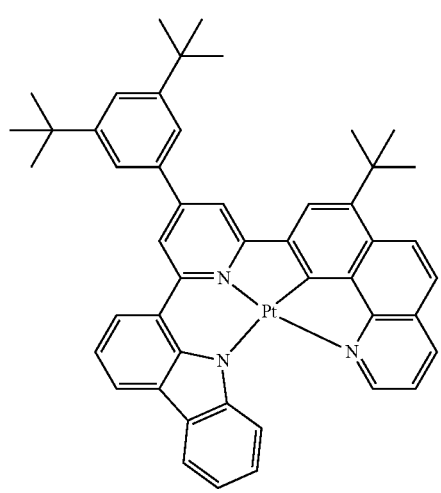
-continued
99
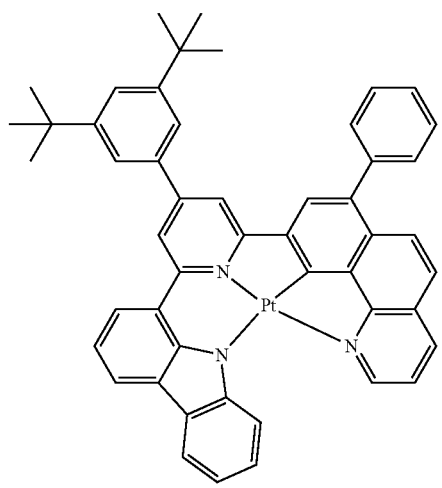
100
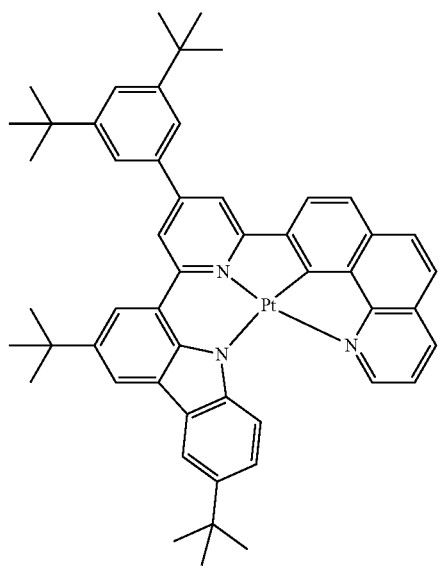
101
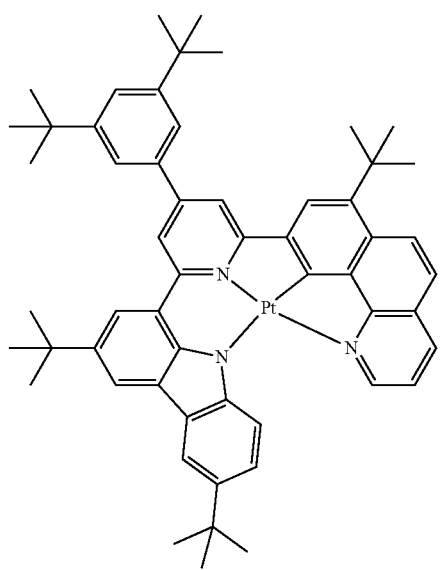

102
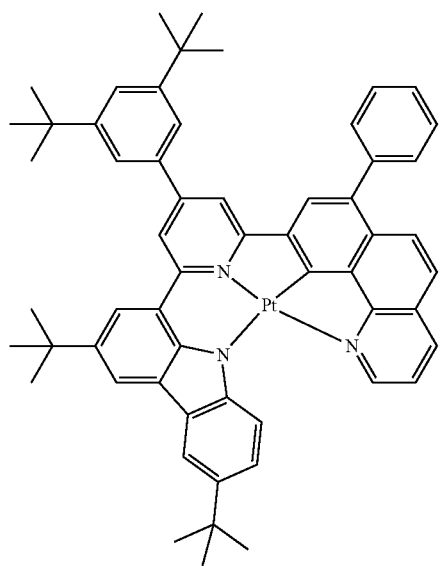
103
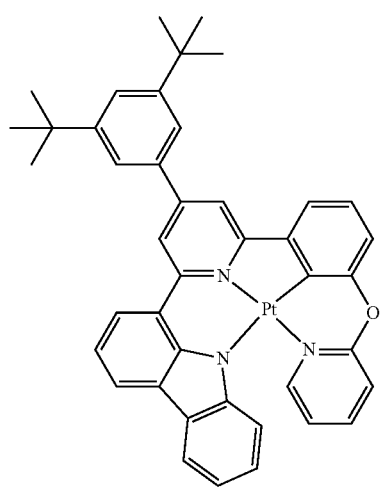
104
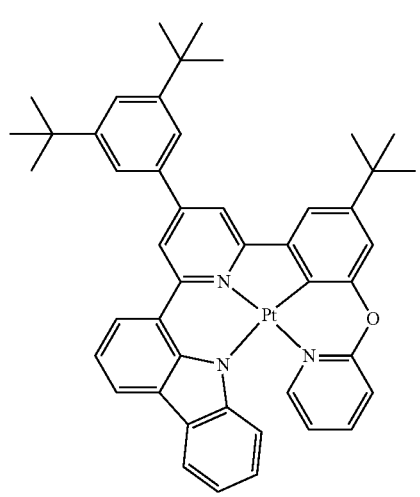
105
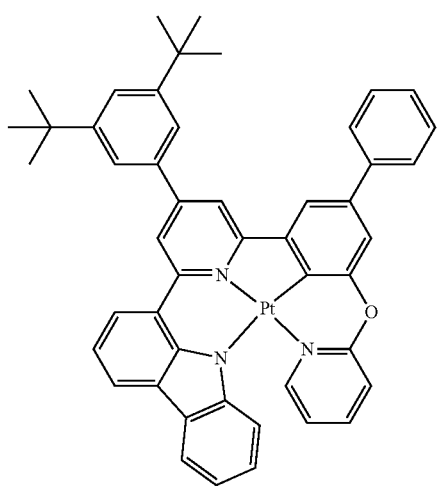
106
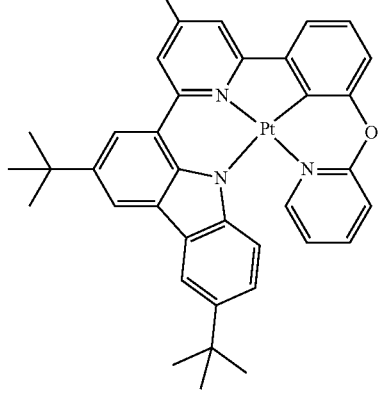
107
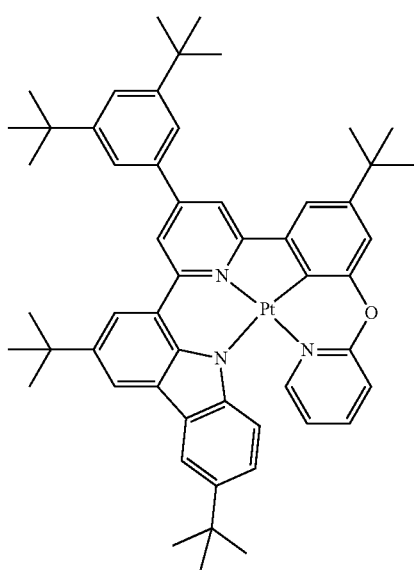

108
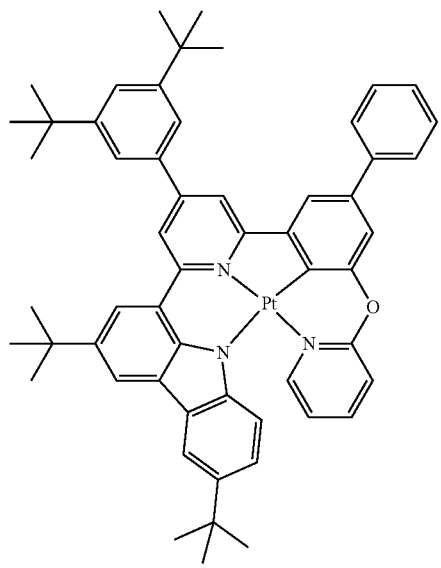
109
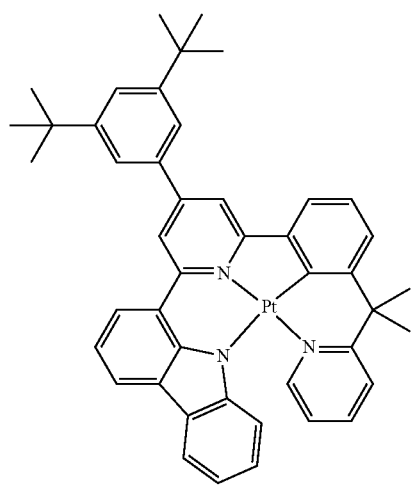
110
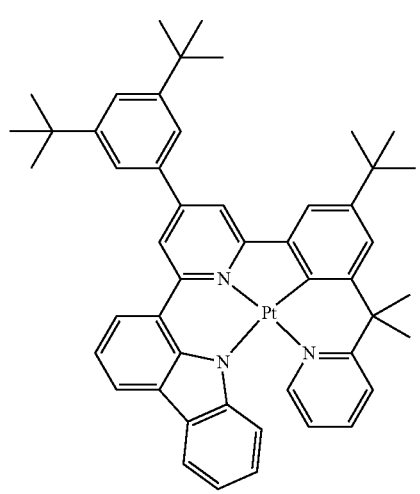
111
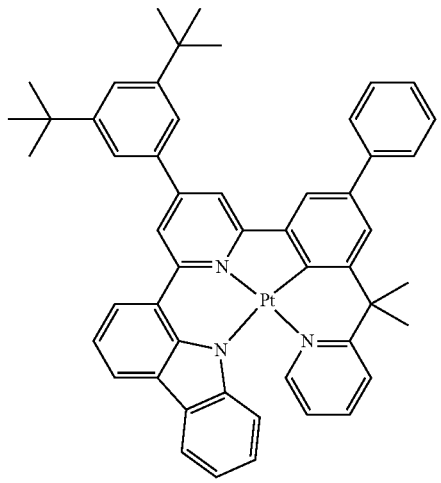
112
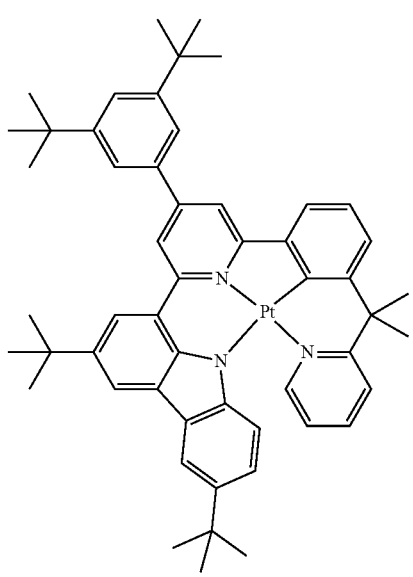
113
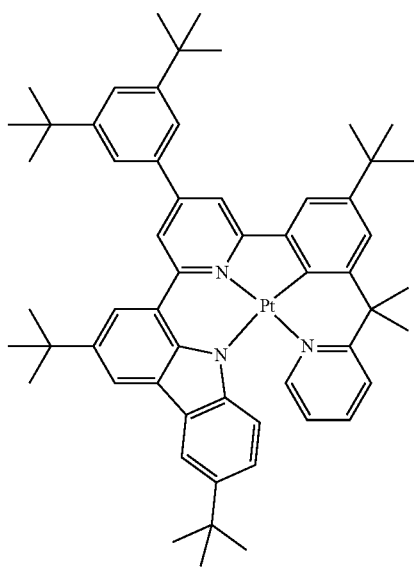

114
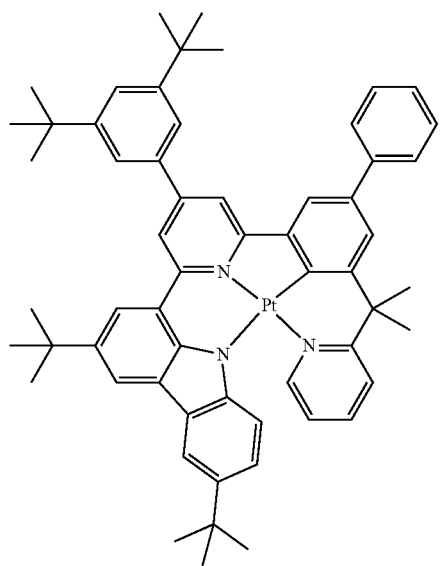
115
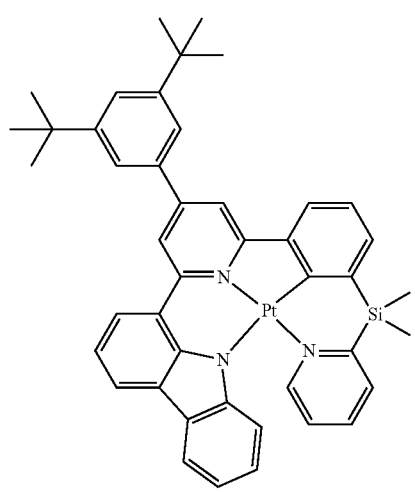
116
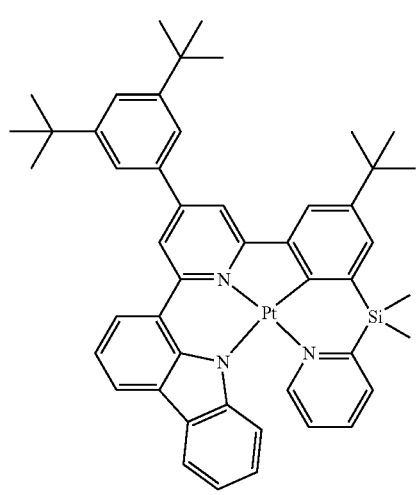
117
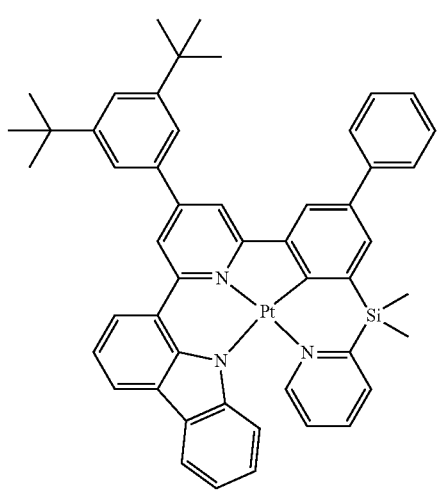
118
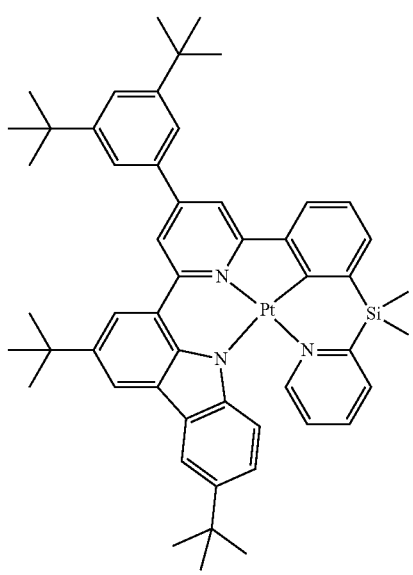
119
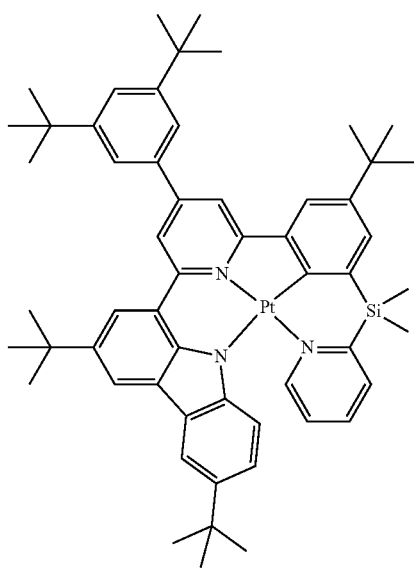

197
-continued
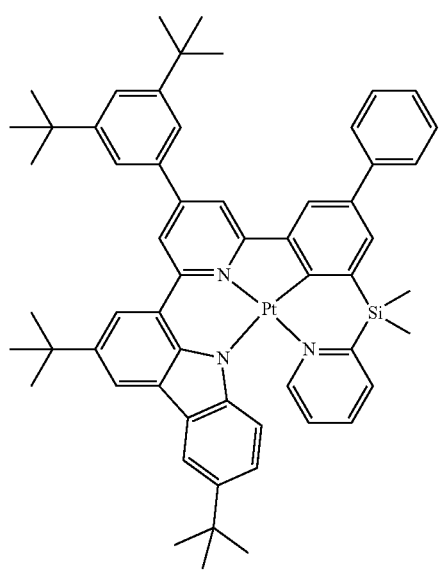
120
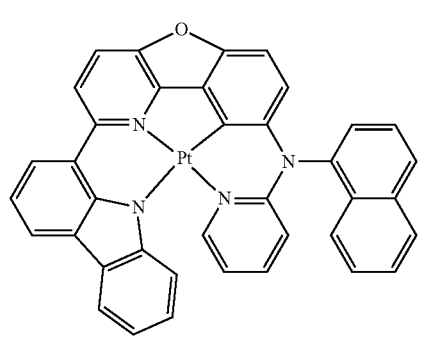
121
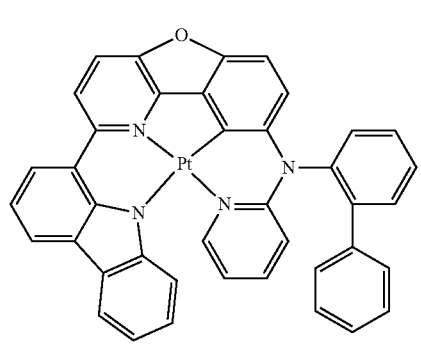
122
198
-continued
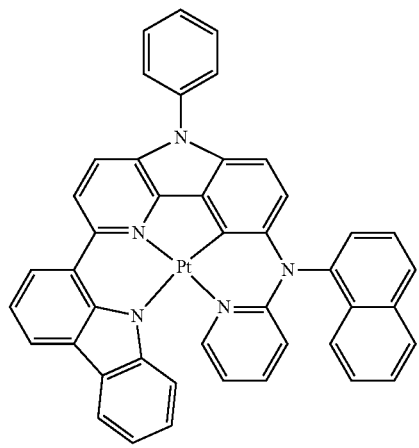
123
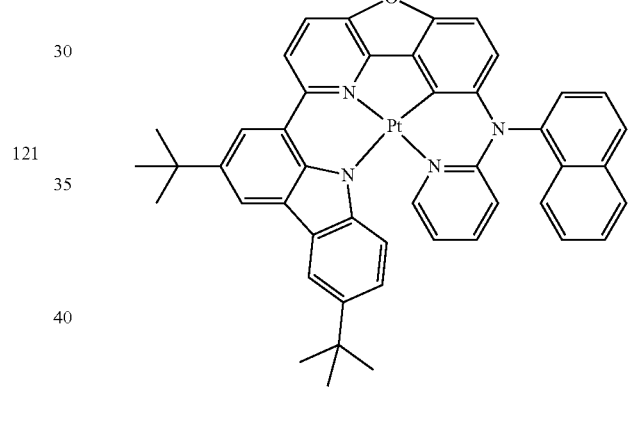
124
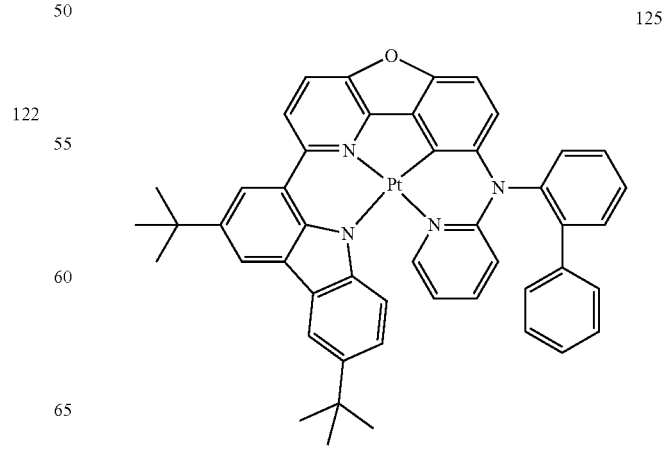
125

126
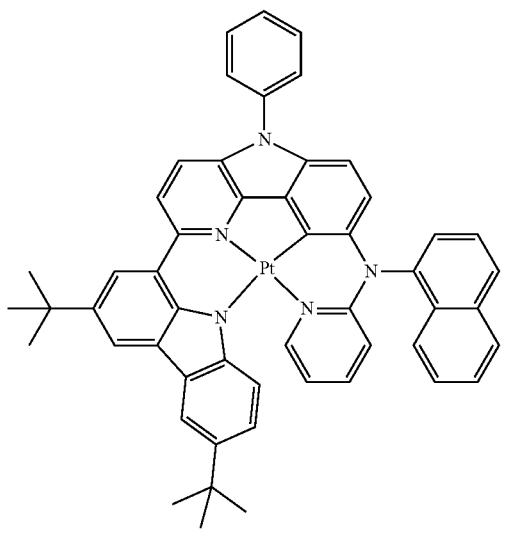

127
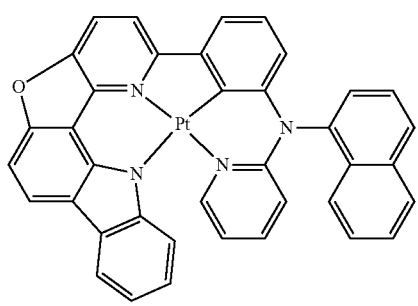

128
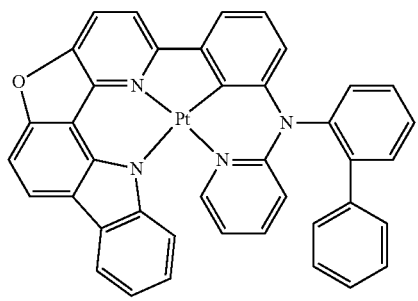

129
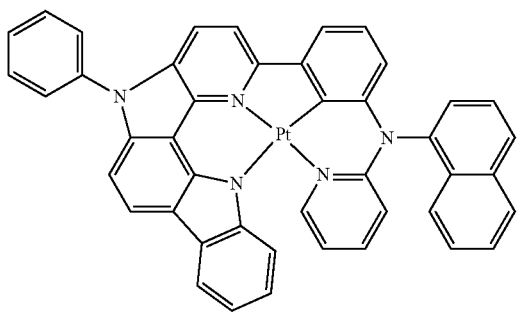

130
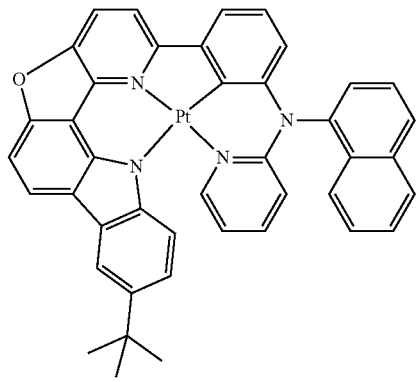

131
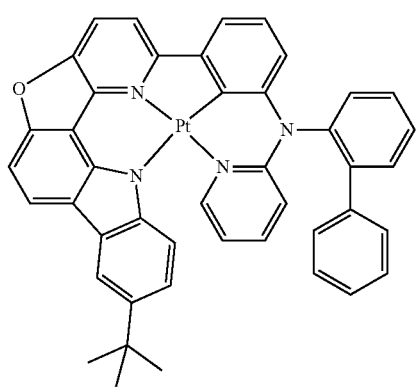

132
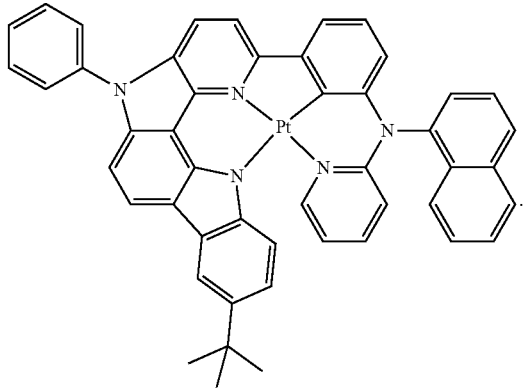

16. An organic light-emitting device comprising:
a first electrode;
a second electrode; and
an organic layer disposed between the first electrode and the second electrode, wherein the organic layer comprising an emission layer,
wherein the organic layer comprises at least one organometallic compound of claim 1.

17. The organic light-emitting device of claim 16, wherein the first electrode is an anode,
the second electrode is a cathode,
the organic layer further comprises a hole transport region disposed between the first electrode and the emission layer and an electron transport region disposed between the emission layer and the second electrode,
the hole transport region comprises a hole injection layer, a hole transport layer, an electron blocking layer, or any combination thereof, and the electron transport region comprises a hole blocking layer, an electron transport layer, an electron injection layer, or any combination thereof.

18. The organic light-emitting device of claim 16, wherein the emission layer comprises the organometallic compound.

19. The organic light-emitting device of claim 18, wherein the emission layer further comprises a host, and an amount of the host is larger than an amount of the organometallic compound.

20. A diagnosis composition comprising at least one organometallic compound of claim 1.

* * * * *